US010413175B2

(12) United States Patent
Yun et al.

(10) Patent No.: US 10,413,175 B2
(45) Date of Patent: *Sep. 17, 2019

(54) PROCESS, ARRANGEMENTS AND SYSTEMS FOR PROVIDING FREQUENCY DOMAIN IMAGING OF A SAMPLE

(71) Applicant: The General Hospital Corporation, Boston, MA (US)

(72) Inventors: Seok-Hyun Yun, Cambridge, MA (US); Johannes F. De Boer, Amstelveen (NL)

(73) Assignee: The General Hospital Corporation, Boson, MA (US)

( * ) Notice: Subject to any disclaimer, the term of this patent is extended or adjusted under 35 U.S.C. 154(b) by 524 days.

This patent is subject to a terminal disclaimer.

(21) Appl. No.: 15/176,938

(22) Filed: Jun. 8, 2016

(65) Prior Publication Data
US 2016/0367132 A1 Dec. 22, 2016

Related U.S. Application Data

(63) Continuation of application No. 13/465,580, filed on May 7, 2012, now Pat. No. 9,364,143, which is a (Continued)

(51) Int. Cl.
*A61B 6/00* (2006.01)
*A61B 3/10* (2006.01)
(Continued)

(52) U.S. Cl.
CPC ............ *A61B 3/102* (2013.01); *A61B 3/0025* (2013.01); *A61B 3/1233* (2013.01); *A61B 3/14* (2013.01);
(Continued)

(58) Field of Classification Search
None
See application file for complete search history.

(56) References Cited

U.S. PATENT DOCUMENTS

| 2,339,754 A | 1/1944 | Brace |
| 3,090,753 A | 5/1963 | Matuszak et al. |
| (Continued) | | |

FOREIGN PATENT DOCUMENTS

| CN | 1550203 | 12/2004 |
| DE | 4105221 | 9/1991 |
| (Continued) | | |

OTHER PUBLICATIONS

Extended European Search Report dated Feb. 17, 2017 for European Patent Application No. 16190822.3.
(Continued)

*Primary Examiner* — Joel F Brutus
(74) *Attorney, Agent, or Firm* — Quarles & Brady LLP

(57) ABSTRACT

Exemplary apparatus, arrangement and method can be provided for obtaining information associated with an anatomical structure or a sample using optical microscopy. For example, a light radiation can be separated into first light radiation(s) directed to an anatomical sample and second light radiation directed to a reference. A wavelength of the radiation can vary over time, and the wavelength can be shorter than approximately 1150 nm. An interference can be detected between third and fourth radiations associated with the first and second radiations and fourth radiation, respectively. At least one image corresponding to portion(s) of the sample can be generated using data associated with the interference. In addition, source(s) can be provided which can be configured to provide an electromagnetic radiation having a wavelength that varies over time. A period of a variation of the wavelength of the first electromagnetic radiation(s) can be shorter than 1 millisecond, and the wavelength can be shorter than approximately 1150 nm.

22 Claims, 12 Drawing Sheets

Related U.S. Application Data continuation of application No. 11/744,287, filed on May 4, 2007, now Pat. No. 8,175,685.

(60) Provisional application No. 60/799,511, filed on May 10, 2006.

(51) Int. Cl.

| | | |
|---|---|---|
| *A61B 5/00* | (2006.01) | |
| *G01N 21/45* | (2006.01) | |
| *G01N 21/47* | (2006.01) | |
| *A61B 3/00* | (2006.01) | |
| *A61B 3/12* | (2006.01) | |
| *A61B 3/14* | (2006.01) | |

(52) U.S. Cl.
CPC .......... *A61B 5/0059* (2013.01); *A61B 5/0066* (2013.01); *A61B 5/418* (2013.01); *G01N 21/45* (2013.01); *G01N 21/4795* (2013.01)

(56) References Cited

U.S. PATENT DOCUMENTS

| | | |
|---|---|---|
| 3,601,480 A | 8/1971 | Randall |
| 3,856,000 A | 12/1974 | Chikama |
| 3,872,407 A | 3/1975 | Hughes |
| 3,941,121 A | 3/1976 | Olinger |
| 3,973,219 A | 8/1976 | Tang et al. |
| 3,983,507 A | 9/1976 | Tang et al. |
| 4,030,827 A | 6/1977 | Delhaye et al. |
| 4,030,831 A | 6/1977 | Gowrinathan |
| 4,140,364 A | 2/1979 | Yamashita et al. |
| 4,141,362 A | 2/1979 | Wurster |
| 4,224,929 A | 9/1980 | Furihata |
| 4,295,738 A | 10/1981 | Meltz et al. |
| 4,300,816 A | 11/1981 | Snitzer et al. |
| 4,303,300 A | 12/1981 | Pressiat et al. |
| 4,428,643 A | 1/1984 | Kay |
| 4,479,499 A | 10/1984 | Alfano |
| 4,533,247 A | 8/1985 | Epworth |
| 4,585,349 A | 4/1986 | Gross et al. |
| 4,601,036 A | 7/1986 | Faxvog et al. |
| 4,607,622 A | 8/1986 | Fritch et al. |
| 4,631,498 A | 12/1986 | Cutler |
| 4,639,999 A | 2/1987 | Daniele |
| 4,650,327 A | 3/1987 | Ogi |
| 4,734,578 A | 3/1988 | Horikawa |
| 4,744,656 A | 5/1988 | Moran et al. |
| 4,751,706 A | 6/1988 | Rohde et al. |
| 4,763,977 A | 8/1988 | Kawasaki et al. |
| 4,770,492 A | 9/1988 | Levin et al. |
| 4,827,907 A | 5/1989 | Tashiro et al. |
| 4,834,111 A | 5/1989 | Khanna et al. |
| 4,868,834 A | 9/1989 | Fox et al. |
| 4,890,901 A | 1/1990 | Cross, Jr. |
| 4,892,406 A | 1/1990 | Waters |
| 4,905,169 A | 2/1990 | Buican et al. |
| 4,909,631 A | 3/1990 | Tan et al. |
| 4,925,302 A | 5/1990 | Cutler |
| 4,928,005 A | 5/1990 | Lefèvre et al. |
| 4,940,328 A | 7/1990 | Hartman |
| 4,965,441 A | 10/1990 | Picard |
| 4,965,599 A | 10/1990 | Roddy et al. |
| 4,966,589 A | 10/1990 | Kaufman |
| 4,984,888 A | 1/1991 | Tobias et al. |
| 4,993,834 A | 2/1991 | Carlhoff et al. |
| 4,998,972 A | 3/1991 | Chin et al. |
| 5,039,193 A | 8/1991 | Snow et al. |
| 5,040,889 A | 8/1991 | Keane |
| 5,045,936 A | 9/1991 | Lobb et al. |
| 5,046,501 A | 9/1991 | Crilly |
| 5,065,331 A | 11/1991 | Vachon et al. |
| 5,085,496 A | 2/1992 | Yoshida et al. |
| 5,120,953 A | 6/1992 | Harris |
| 5,121,983 A | 6/1992 | Lee |
| 5,127,730 A | 7/1992 | Brelje et al. |
| 5,177,488 A | 1/1993 | Wang et al. |
| 5,197,470 A | 3/1993 | Helfer et al. |
| 5,202,745 A | 4/1993 | Sorin et al. |
| 5,202,931 A | 4/1993 | Bacus et al. |
| 5,208,651 A | 5/1993 | Buican |
| 5,212,667 A | 5/1993 | Tomlinson et al. |
| 5,214,538 A | 5/1993 | Lobb |
| 5,217,456 A | 6/1993 | Narciso, Jr. |
| 5,228,001 A | 7/1993 | Birge et al. |
| 5,241,364 A | 8/1993 | Kimura et al. |
| 5,248,876 A | 9/1993 | Kerstens et al. |
| 5,250,186 A | 10/1993 | Dollinger et al. |
| 5,251,009 A | 10/1993 | Bruno |
| 5,262,644 A | 11/1993 | Maguire |
| 5,275,594 A | 1/1994 | Baker |
| 5,281,811 A | 1/1994 | Lewis |
| 5,283,795 A | 2/1994 | Fink |
| 5,291,885 A | 3/1994 | Taniji et al. |
| 5,293,872 A | 3/1994 | Alfano et al. |
| 5,293,873 A | 3/1994 | Fang |
| 5,302,025 A | 4/1994 | Kleinerman |
| 5,304,173 A | 4/1994 | Kittrell et al. |
| 5,304,810 A | 4/1994 | Amos |
| 5,305,759 A | 4/1994 | Kaneko et al. |
| 5,317,389 A | 5/1994 | Hochberg et al. |
| 5,318,024 A | 6/1994 | Kittrell et al. |
| 5,321,501 A | 6/1994 | Swanson et al. |
| 5,333,144 A | 7/1994 | Liedenbaum et al. |
| 5,348,003 A | 9/1994 | Caro |
| 5,353,790 A | 10/1994 | Jacques et al. |
| 5,383,467 A | 1/1995 | Auer et al. |
| 5,394,235 A | 2/1995 | Takeuchi et al. |
| 5,400,771 A | 3/1995 | Pirak et al. |
| 5,404,415 A | 4/1995 | Mori et al. |
| 5,411,016 A | 5/1995 | Kume et al. |
| 5,414,509 A | 5/1995 | Veligdan |
| 5,419,323 A | 5/1995 | Kittrell et al. |
| 5,424,827 A | 6/1995 | Horwitz et al. |
| 5,439,000 A | 8/1995 | Gunderson et al. |
| 5,441,053 A | 8/1995 | Lodder et al. |
| 5,450,203 A | 9/1995 | Penkethman |
| 5,454,807 A | 10/1995 | Lennox et al. |
| 5,459,325 A | 10/1995 | Hueton et al. |
| 5,459,570 A | 10/1995 | Swanson et al. |
| 5,465,147 A | 11/1995 | Swanson |
| 5,486,701 A | 1/1996 | Norton et al. |
| 5,491,524 A | 2/1996 | Hellmuth et al. |
| 5,491,552 A | 2/1996 | Kittrell |
| 5,522,004 A | 5/1996 | Djupsjobacka et al. |
| 5,526,338 A | 6/1996 | Hasman et al. |
| 5,555,087 A | 9/1996 | Miyagawa et al. |
| 5,562,100 A | 10/1996 | Kittrell et al. |
| 5,565,983 A | 10/1996 | Barnard et al. |
| 5,565,986 A | 10/1996 | Knüttel |
| 5,566,267 A | 10/1996 | Neuberger |
| 5,583,342 A | 12/1996 | Ichie |
| 5,590,660 A | 1/1997 | MacAulay et al. |
| 5,600,486 A | 2/1997 | Gal et al. |
| 5,601,087 A | 2/1997 | Richards-Kortum et al. |
| 5,621,830 A | 4/1997 | Lucey et al. |
| 5,623,336 A | 4/1997 | Raab et al. |
| 5,635,830 A | 6/1997 | Itoh |
| 5,649,924 A | 7/1997 | Everett et al. |
| 5,697,373 A | 12/1997 | Gunderson et al. |
| 5,698,397 A | 12/1997 | Zarling et al. |
| 5,701,155 A | 12/1997 | Welch et al. |
| 5,710,630 A | 1/1998 | Essenpreis et al. |
| 5,716,324 A | 2/1998 | Toida |
| 5,719,399 A | 2/1998 | Alfano et al. |
| 5,730,731 A | 3/1998 | Mollenauer et al. |
| 5,735,276 A | 4/1998 | Lemelson |
| 5,740,808 A | 4/1998 | Panescu et al. |
| 5,748,318 A | 5/1998 | Maris et al. |
| 5,748,598 A | 5/1998 | Swanson et al. |
| 5,752,518 A | 5/1998 | McGee et al. |
| 5,784,352 A | 7/1998 | Swanson et al. |
| 5,785,651 A | 7/1998 | Kuhn et al. |
| 5,795,295 A | 8/1998 | Hellmuth et al. |

(56) References Cited

U.S. PATENT DOCUMENTS

| | | |
|---|---|---|
| 5,801,826 A | 9/1998 | Williams |
| 5,801,831 A | 9/1998 | Sargoytchev et al. |
| 5,803,082 A | 9/1998 | Stapleton et al. |
| 5,807,261 A | 9/1998 | Benaron et al. |
| 5,810,719 A | 9/1998 | Toida |
| 5,817,144 A | 10/1998 | Gregory |
| 5,836,877 A | 11/1998 | Zavislan et al. |
| 5,840,023 A | 11/1998 | Oraevsky et al. |
| 5,840,031 A | 11/1998 | Crowley |
| 5,840,075 A | 11/1998 | Mueller et al. |
| 5,842,995 A | 12/1998 | Mahadevan-Jansen et al. |
| 5,843,000 A | 12/1998 | Nishioka et al. |
| 5,843,052 A | 12/1998 | Benja-Athon |
| 5,847,827 A | 12/1998 | Fercher |
| 5,862,273 A | 1/1999 | Pelletier |
| 5,865,754 A | 2/1999 | Sevick-Muraca et al. |
| 5,867,268 A | 2/1999 | Gelikonov et al. |
| 5,871,449 A | 2/1999 | Brown |
| 5,872,879 A | 2/1999 | Hamm |
| 5,877,856 A | 3/1999 | Fercher |
| 5,887,009 A | 3/1999 | Mandella et al. |
| 5,892,583 A | 4/1999 | Li |
| 5,910,839 A | 6/1999 | Erskine et al. |
| 5,912,764 A | 6/1999 | Togino |
| 5,920,373 A | 7/1999 | Bille |
| 5,920,390 A | 7/1999 | Farahi et al. |
| 5,921,926 A | 7/1999 | Rolland et al. |
| 5,926,592 A | 7/1999 | De Boer et al. |
| 5,949,929 A | 9/1999 | Hamm |
| 5,951,482 A | 9/1999 | Winston et al. |
| 5,955,737 A | 9/1999 | Hallidy et al. |
| 5,956,355 A | 9/1999 | Swanson et al. |
| 5,968,064 A | 10/1999 | Selmon et al. |
| 5,975,697 A | 11/1999 | Podoleanu et al. |
| 5,983,125 A | 11/1999 | Alfano et al. |
| 5,987,346 A | 11/1999 | Benaron et al. |
| 5,991,697 A | 11/1999 | Nelson et al. |
| 5,994,690 A | 11/1999 | Kulkarni et al. |
| 5,995,223 A | 11/1999 | Power |
| 6,002,480 A | 12/1999 | Izatt et al. |
| 6,004,314 A | 12/1999 | Wei et al. |
| 6,006,128 A | 12/1999 | Izatt et al. |
| 6,007,996 A | 12/1999 | McNamara et al. |
| 6,010,449 A | 1/2000 | Selmon et al. |
| 6,014,214 A | 1/2000 | Li |
| 6,016,197 A | 1/2000 | Krivoshlykov |
| 6,020,963 A | 2/2000 | Dimarzio et al. |
| 6,025,956 A | 2/2000 | Nagano et al. |
| 6,033,721 A | 3/2000 | Nassuphis |
| 6,037,579 A | 3/2000 | Chan et al. |
| 6,044,288 A | 3/2000 | Wake et al. |
| 6,045,511 A | 4/2000 | Ott et al. |
| 6,048,742 A | 4/2000 | Weyburne et al. |
| 6,052,186 A | 4/2000 | Tsai |
| 6,053,613 A | 4/2000 | Wei et al. |
| 6,069,698 A | 5/2000 | Ozawa et al. |
| 6,078,047 A | 6/2000 | Mittleman et al. |
| 6,091,496 A | 7/2000 | Hill |
| 6,091,984 A | 7/2000 | Perelman et al. |
| 6,094,274 A | 7/2000 | Yokoi |
| 6,107,048 A | 8/2000 | Goldenring et al. |
| 6,111,645 A | 8/2000 | Tearney et al. |
| 6,117,128 A | 9/2000 | Gregory |
| 6,120,516 A | 9/2000 | Selmon et al. |
| 6,134,003 A | 10/2000 | Tearney et al. |
| 6,134,010 A | 10/2000 | Zavislan |
| 6,134,033 A | 10/2000 | Bergano et al. |
| 6,141,577 A | 10/2000 | Rolland et al. |
| 6,151,522 A | 11/2000 | Alfano et al. |
| 6,159,445 A | 12/2000 | Klaveness et al. |
| 6,160,826 A | 12/2000 | Swanson et al. |
| 6,161,031 A | 12/2000 | Hochman et al. |
| 6,166,373 A | 12/2000 | Mao |
| 6,174,291 B1 | 1/2001 | McMahon et al. |
| 6,175,669 B1 | 1/2001 | Colston et al. |
| 6,185,271 B1 | 2/2001 | Kinsinger |
| 6,191,862 B1 | 2/2001 | Swanson et al. |
| 6,193,676 B1 | 2/2001 | Winston et al. |
| 6,198,956 B1 | 3/2001 | Dunne |
| 6,201,989 B1 | 3/2001 | Whitehead et al. |
| 6,208,415 B1 | 3/2001 | De Boer et al. |
| 6,208,887 B1 | 3/2001 | Clarke |
| 6,245,026 B1 | 6/2001 | Campbell et al. |
| 6,249,349 B1 | 6/2001 | Lauer |
| 6,249,381 B1 | 6/2001 | Suganuma |
| 6,249,630 B1 | 6/2001 | Stock et al. |
| 6,263,234 B1 | 7/2001 | Engelhardt et al. |
| 6,264,610 B1 | 7/2001 | Zhu |
| 6,272,268 B1 | 8/2001 | Miller et al. |
| 6,272,376 B1 | 8/2001 | Marcu et al. |
| 6,274,871 B1 | 8/2001 | Dukor et al. |
| 6,282,011 B1 | 8/2001 | Tearney et al. |
| 6,297,018 B1 | 10/2001 | French et al. |
| 6,301,048 B1 | 10/2001 | Cao et al. |
| 6,308,092 B1 | 10/2001 | Hoyns |
| 6,324,419 B1 | 11/2001 | Guzelsu et al. |
| 6,341,036 B1 | 1/2002 | Tearney et al. |
| 6,353,693 B1 | 3/2002 | Kano et al. |
| 6,359,692 B1 | 3/2002 | Groot |
| 6,374,128 B1 | 4/2002 | Toida et al. |
| 6,377,349 B1 | 4/2002 | Fercher |
| 6,384,915 B1 | 5/2002 | Everett et al. |
| 6,393,312 B1 | 5/2002 | Hoyns |
| 6,394,964 B1 | 5/2002 | Sievert, Jr. et al. |
| 6,396,941 B1 | 5/2002 | Bacus et al. |
| 6,421,164 B2 | 7/2002 | Tearney et al. |
| 6,437,867 B2 | 8/2002 | Zeylikovich et al. |
| 6,441,892 B2 | 8/2002 | Xiao et al. |
| 6,441,959 B1 | 8/2002 | Yang et al. |
| 6,445,485 B1 | 9/2002 | Frigo et al. |
| 6,445,939 B1 | 9/2002 | Swanson et al. |
| 6,445,944 B1 | 9/2002 | Ostrovsky |
| 6,459,487 B1 | 10/2002 | Chen et al. |
| 6,463,313 B1 | 10/2002 | Winston et al. |
| 6,469,846 B2 | 10/2002 | Ebizuka et al. |
| 6,475,159 B1 | 11/2002 | Casscells et al. |
| 6,475,210 B1 | 11/2002 | Phelps et al. |
| 6,477,403 B1 | 11/2002 | Eguchi et al. |
| 6,485,413 B1 | 11/2002 | Boppart et al. |
| 6,485,482 B1 | 11/2002 | Belef |
| 6,501,551 B1 | 12/2002 | Tearney et al. |
| 6,501,878 B2 | 12/2002 | Hughes et al. |
| 6,516,014 B1 | 2/2003 | Sellin et al. |
| 6,517,532 B1 | 2/2003 | Altshuler et al. |
| 6,538,817 B1 | 3/2003 | Farmer et al. |
| 6,540,391 B2 | 4/2003 | Lanzetta et al. |
| 6,549,801 B1 | 4/2003 | Chen et al. |
| 6,552,796 B2 | 4/2003 | Magnin et al. |
| 6,556,305 B1 | 4/2003 | Aziz et al. |
| 6,556,853 B1 | 4/2003 | Cabib et al. |
| 6,558,324 B1 | 5/2003 | Von Behren et al. |
| 6,560,259 B1 | 5/2003 | Hwang et al. |
| 6,564,087 B1 | 5/2003 | Pitris et al. |
| 6,564,089 B2 | 5/2003 | Izatt et al. |
| 6,567,585 B2 | 5/2003 | De Boer et al. |
| 6,593,101 B2 | 7/2003 | Richards-Kortum et al. |
| 6,611,833 B1 | 8/2003 | Johnson et al. |
| 6,615,071 B1 | 9/2003 | Casscells, III et al. |
| 6,622,732 B2 | 9/2003 | Constantz |
| 6,654,127 B2 | 11/2003 | Everett et al. |
| 6,657,730 B2 | 12/2003 | Pfau et al. |
| 6,658,278 B2 | 12/2003 | Gruhl |
| 6,680,780 B1 | 1/2004 | Fee |
| 6,685,885 B2 | 2/2004 | Nolte et al. |
| 6,687,007 B1 | 2/2004 | Meigs |
| 6,687,010 B1 | 2/2004 | Horii et al. |
| 6,687,036 B2 | 2/2004 | Riza |
| 6,692,430 B2 | 2/2004 | Adler |
| 6,701,181 B2 | 3/2004 | Tang et al. |
| 6,721,094 B1 | 4/2004 | Sinclair et al. |
| 6,725,073 B1 | 4/2004 | Motamedi et al. |
| 6,738,144 B1 | 5/2004 | Dogariu et al. |
| 6,741,355 B2 | 5/2004 | Drabarek |
| 6,741,884 B1 | 5/2004 | Freeman et al. |

(56) References Cited

U.S. PATENT DOCUMENTS

| | | |
|---|---|---|
| 6,757,467 B1 | 6/2004 | Rogers |
| 6,790,175 B1 | 9/2004 | Furusawa et al. |
| 6,806,963 B1 | 10/2004 | Wälti et al. |
| 6,816,743 B2 | 11/2004 | Moreno et al. |
| 6,831,781 B2 | 12/2004 | Tearney et al. |
| 6,839,496 B1 | 1/2005 | Mills et al. |
| 6,882,432 B2 | 4/2005 | Deck |
| 6,900,899 B2 | 5/2005 | Nevis |
| 6,903,820 B2 | 6/2005 | Wang |
| 6,909,105 B1 | 6/2005 | Heintzmann et al. |
| 6,949,072 B2 | 9/2005 | Furnish et al. |
| 6,961,123 B1 | 11/2005 | Wang et al. |
| 6,980,299 B1 | 12/2005 | de Boer |
| 6,996,549 B2 | 2/2006 | Zhang et al. |
| 7,006,231 B2 | 2/2006 | Ostrovsky et al. |
| 7,006,232 B2 | 2/2006 | Rollins et al. |
| 7,019,838 B2 | 3/2006 | Izatt et al. |
| 7,027,633 B2 | 4/2006 | Foran et al. |
| 7,061,622 B2 | 6/2006 | Rollins et al. |
| 7,072,047 B2 | 7/2006 | Westphal et al. |
| 7,075,658 B2 | 7/2006 | Izatt et al. |
| 7,099,358 B1 | 8/2006 | Chong et al. |
| 7,113,288 B2 | 9/2006 | Fercher |
| 7,113,625 B2 | 9/2006 | Watson et al. |
| 7,130,320 B2 | 10/2006 | Tobiason et al. |
| 7,139,598 B2 | 11/2006 | Hull et al. |
| 7,142,835 B2 | 11/2006 | Paulus |
| 7,148,970 B2 | 12/2006 | De Boer |
| 7,177,027 B2 | 2/2007 | Hirasawa et al. |
| 7,190,464 B2 | 3/2007 | Alphonse |
| 7,230,708 B2 | 6/2007 | Lapotko et al. |
| 7,231,243 B2 | 6/2007 | Tearney et al. |
| 7,236,637 B2 | 6/2007 | Sirohey et al. |
| 7,242,480 B2 | 7/2007 | Alphonse |
| 7,267,494 B2 | 9/2007 | Deng et al. |
| 7,272,252 B2 | 9/2007 | De La Torre-Bueno et al. |
| 7,304,798 B2 | 12/2007 | Izumi et al. |
| 7,310,150 B2 | 12/2007 | Tearney et al. |
| 7,330,270 B2 | 2/2008 | O'Hara et al. |
| 7,336,366 B2 | 2/2008 | Choma et al. |
| 7,342,659 B2 | 3/2008 | Horn et al. |
| 7,355,716 B2 | 4/2008 | De Boer et al. |
| 7,355,721 B2 | 4/2008 | Quadling et al. |
| 7,359,062 B2 | 4/2008 | Chen et al. |
| 7,365,858 B2 | 4/2008 | Fang-Yen et al. |
| 7,366,376 B2 | 4/2008 | Shishkov et al. |
| 7,382,809 B2 | 6/2008 | Chong et al. |
| 7,391,520 B2 | 6/2008 | Zhou et al. |
| 7,458,683 B2 | 12/2008 | Chernyak et al. |
| 7,530,948 B2 | 5/2009 | Seibel et al. |
| 7,539,530 B2 | 5/2009 | Caplan et al. |
| 7,609,391 B2 | 10/2009 | Betzig |
| 7,630,083 B2 | 12/2009 | de Boer et al. |
| 7,643,152 B2 | 1/2010 | de Boer et al. |
| 7,643,153 B2 | 1/2010 | de Boer et al. |
| 7,646,905 B2 | 1/2010 | Guittet et al. |
| 7,649,160 B2 | 1/2010 | Colomb et al. |
| 7,664,300 B2 | 2/2010 | Lange et al. |
| 7,733,497 B2 | 6/2010 | Yun et al. |
| 7,782,464 B2 | 8/2010 | Mujat et al. |
| 7,799,558 B1 | 9/2010 | Dultz |
| 7,805,034 B2 | 9/2010 | Kato et al. |
| 7,911,621 B2 | 3/2011 | Motaghiannezam et al. |
| 7,969,578 B2 | 6/2011 | Yun et al. |
| 7,973,936 B2 | 7/2011 | Dantus |
| 2001/0020126 A1 | 9/2001 | Khoury |
| 2001/0036002 A1 | 11/2001 | Tearney et al. |
| 2001/0047137 A1 | 11/2001 | Moreno et al. |
| 2001/0055462 A1 | 12/2001 | Seibel |
| 2002/0016533 A1 | 2/2002 | Marchitto et al. |
| 2002/0024015 A1 | 2/2002 | Hoffmann et al. |
| 2002/0037252 A1 | 3/2002 | Toida et al. |
| 2002/0048025 A1 | 4/2002 | Takaoka |
| 2002/0048026 A1 | 4/2002 | Isshiki et al. |
| 2002/0052547 A1 | 5/2002 | Toida |
| 2002/0057431 A1 | 5/2002 | Fateley et al. |
| 2002/0064341 A1 | 5/2002 | Fauver et al. |
| 2002/0076152 A1 | 6/2002 | Hughes et al. |
| 2002/0085209 A1 | 7/2002 | Mittleman et al. |
| 2002/0086347 A1 | 7/2002 | Johnson et al. |
| 2002/0091322 A1 | 7/2002 | Chaiken et al. |
| 2002/0093662 A1 | 7/2002 | Chen et al. |
| 2002/0109851 A1 | 8/2002 | Deck |
| 2002/0113965 A1 | 8/2002 | Yun |
| 2002/0122182 A1 | 9/2002 | Everett et al. |
| 2002/0122246 A1 | 9/2002 | Tearney et al. |
| 2002/0140942 A1 | 10/2002 | Fee et al. |
| 2002/0158211 A1 | 10/2002 | Gillispie |
| 2002/0161357 A1 | 10/2002 | Rox et al. |
| 2002/0163622 A1 | 11/2002 | Magnin et al. |
| 2002/0166946 A1 | 11/2002 | Iizuka et al. |
| 2002/0168158 A1 | 11/2002 | Furusawa et al. |
| 2002/0172485 A1 | 11/2002 | Keaton et al. |
| 2002/0183623 A1 | 12/2002 | Tang et al. |
| 2002/0188204 A1 | 12/2002 | McNamara et al. |
| 2002/0196446 A1 | 12/2002 | Roth et al. |
| 2002/0198457 A1 | 12/2002 | Tearney et al. |
| 2003/0001071 A1 | 1/2003 | Mandella et al. |
| 2003/0013973 A1 | 1/2003 | Georgakoudi et al. |
| 2003/0023153 A1 | 1/2003 | Izatt et al. |
| 2003/0025917 A1 | 2/2003 | Suhami |
| 2003/0026735 A1 | 2/2003 | Nolte et al. |
| 2003/0028114 A1 | 2/2003 | Casscells, III et al. |
| 2003/0030816 A1 | 2/2003 | Eom et al. |
| 2003/0043381 A1 | 3/2003 | Fercher |
| 2003/0053673 A1 | 3/2003 | Dewaele et al. |
| 2003/0067607 A1 | 4/2003 | Wolleschensky et al. |
| 2003/0082105 A1 | 5/2003 | Fischman et al. |
| 2003/0097048 A1 | 5/2003 | Ryan et al. |
| 2003/0108911 A1 | 6/2003 | Klimant et al. |
| 2003/0120137 A1 | 6/2003 | Pawluczyk et al. |
| 2003/0135101 A1 | 7/2003 | Webler |
| 2003/0137669 A1 | 7/2003 | Rollins et al. |
| 2003/0164952 A1 | 9/2003 | Deichmann et al. |
| 2003/0165263 A1 | 9/2003 | Hamer et al. |
| 2003/0171691 A1 | 9/2003 | Casscells, III et al. |
| 2003/0174339 A1 | 9/2003 | Feldchtein et al. |
| 2003/0199769 A1 | 10/2003 | Podoleanu et al. |
| 2003/0216719 A1 | 11/2003 | Debenedictis et al. |
| 2003/0218756 A1 | 11/2003 | Chen et al. |
| 2003/0220749 A1 | 11/2003 | Chen et al. |
| 2003/0236443 A1 | 12/2003 | Cespedes et al. |
| 2004/0002650 A1 | 1/2004 | Mandrusov et al. |
| 2004/0039252 A1 | 2/2004 | Koch |
| 2004/0039298 A1 | 2/2004 | Abreu |
| 2004/0054268 A1 | 3/2004 | Esenaliev et al. |
| 2004/0072200 A1 | 4/2004 | Rigler et al. |
| 2004/0075841 A1 | 4/2004 | Van Neste et al. |
| 2004/0076940 A1 | 4/2004 | Alexander et al. |
| 2004/0077949 A1 | 4/2004 | Blofgett et al. |
| 2004/0085540 A1 | 5/2004 | Lapotko et al. |
| 2004/0086245 A1 | 5/2004 | Farroni et al. |
| 2004/0095464 A1 | 5/2004 | Miyagi et al. |
| 2004/0100631 A1 | 5/2004 | Bashkansky et al. |
| 2004/0100681 A1 | 5/2004 | Bjarklev et al. |
| 2004/0110206 A1 | 6/2004 | Wong et al. |
| 2004/0126048 A1 | 7/2004 | Dave et al. |
| 2004/0126120 A1 | 7/2004 | Cohen et al. |
| 2004/0133191 A1 | 7/2004 | Momiuchi et al. |
| 2004/0150829 A1 | 8/2004 | Koch et al. |
| 2004/0150830 A1 | 8/2004 | Chan |
| 2004/0152989 A1 | 8/2004 | Puttappa et al. |
| 2004/0165184 A1 | 8/2004 | Mizuno |
| 2004/0166593 A1 | 8/2004 | Nolte et al. |
| 2004/0189999 A1 | 9/2004 | De Groot et al. |
| 2004/0204651 A1 | 10/2004 | Freeman et al. |
| 2004/0212808 A1 | 10/2004 | Okawa et al. |
| 2004/0239938 A1 | 12/2004 | Izatt et al. |
| 2004/0246490 A1 | 12/2004 | Wang |
| 2004/0246583 A1 | 12/2004 | Mueller et al. |
| 2004/0247268 A1 | 12/2004 | Ishihara et al. |
| 2004/0254474 A1 | 12/2004 | Seibel et al. |
| 2004/0258106 A1 | 12/2004 | Araujo et al. |
| 2004/0263843 A1 | 12/2004 | Knopp et al. |

(56) References Cited

U.S. PATENT DOCUMENTS

| | | |
|---|---|---|
| 2005/0004453 A1 | 1/2005 | Tearney et al. |
| 2005/0018133 A1 | 1/2005 | Huang et al. |
| 2005/0018200 A1 | 1/2005 | Guillermo et al. |
| 2005/0018201 A1* | 1/2005 | de Boer ............... A61B 5/0059 356/479 |
| 2005/0035295 A1 | 2/2005 | Bouma et al. |
| 2005/0036150 A1 | 2/2005 | Izatt et al. |
| 2005/0046837 A1 | 3/2005 | Izumi et al. |
| 2005/0057680 A1 | 3/2005 | Agan |
| 2005/0057756 A1 | 3/2005 | Fang-Yen et al. |
| 2005/0059894 A1 | 3/2005 | Zeng et al. |
| 2005/0065421 A1 | 3/2005 | Burckhardt et al. |
| 2005/0075547 A1 | 4/2005 | Wang |
| 2005/0083534 A1 | 4/2005 | Riza et al. |
| 2005/0119567 A1 | 6/2005 | Choi et al. |
| 2005/0128488 A1 | 6/2005 | Yelin et al. |
| 2005/0165303 A1 | 7/2005 | Kleen et al. |
| 2005/0171438 A1 | 8/2005 | Chen et al. |
| 2005/0190372 A1 | 9/2005 | Dogariu et al. |
| 2005/0197530 A1 | 9/2005 | Daniel et al. |
| 2005/0221270 A1 | 10/2005 | Connelly et al. |
| 2005/0254059 A1 | 11/2005 | Alphonse |
| 2005/0254061 A1 | 11/2005 | Alphonse et al. |
| 2006/0020172 A1 | 1/2006 | Luerssen et al. |
| 2006/0033923 A1 | 2/2006 | Hirasawa et al. |
| 2006/0039004 A1 | 2/2006 | De Boer et al. |
| 2006/0093276 A1 | 5/2006 | Bouma et al. |
| 2006/0103850 A1 | 5/2006 | Alphonse et al. |
| 2006/0106375 A1 | 5/2006 | Werneth et al. |
| 2006/0146339 A1 | 7/2006 | Fujita et al. |
| 2006/0155193 A1 | 7/2006 | Leonardi et al. |
| 2006/0164639 A1 | 7/2006 | Horn et al. |
| 2006/0167363 A1 | 7/2006 | Bernstein et al. |
| 2006/0171503 A1 | 8/2006 | O'Hara et al. |
| 2006/0184048 A1 | 8/2006 | Saadat et al. |
| 2006/0189928 A1 | 8/2006 | Camus et al. |
| 2006/0193352 A1 | 8/2006 | Chong et al. |
| 2006/0224053 A1 | 10/2006 | Black et al. |
| 2006/0244973 A1 | 11/2006 | Yun et al. |
| 2006/0279742 A1 | 12/2006 | Tearney |
| 2007/0002435 A1 | 1/2007 | Ye et al. |
| 2007/0019208 A1 | 1/2007 | Toida et al. |
| 2007/0024860 A1 | 2/2007 | Tobiason et al. |
| 2007/0035743 A1 | 2/2007 | Vakoc et al. |
| 2007/0038040 A1 | 2/2007 | Cense et al. |
| 2007/0048818 A1 | 3/2007 | Rosen et al. |
| 2007/0070496 A1 | 3/2007 | Gweon et al. |
| 2007/0076217 A1 | 4/2007 | Baker et al. |
| 2007/0086013 A1 | 4/2007 | De Lega et al. |
| 2007/0086017 A1 | 4/2007 | Buckland et al. |
| 2007/0091317 A1 | 4/2007 | Freischlad et al. |
| 2007/0133002 A1 | 6/2007 | Wax et al. |
| 2007/0188855 A1 | 8/2007 | Milen et al. |
| 2007/0203404 A1 | 8/2007 | Zysk et al. |
| 2007/0208255 A1 | 9/2007 | Czaniera et al. |
| 2007/0223006 A1 | 9/2007 | Tearney et al. |
| 2007/0233056 A1 | 10/2007 | Yun |
| 2007/0233396 A1 | 10/2007 | Tearney et al. |
| 2007/0236700 A1 | 10/2007 | Yun et al. |
| 2007/0253901 A1 | 11/2007 | Deng et al. |
| 2007/0258094 A1 | 11/2007 | Izatt et al. |
| 2007/0291277 A1 | 12/2007 | Everett et al. |
| 2008/0002197 A1 | 1/2008 | Sun et al. |
| 2008/0007734 A1 | 1/2008 | Park et al. |
| 2008/0021275 A1 | 1/2008 | Tearney et al. |
| 2008/0049220 A1 | 2/2008 | Izzia et al. |
| 2008/0070323 A1 | 3/2008 | Hess et al. |
| 2008/0094613 A1 | 4/2008 | de Boer et al. |
| 2008/0094637 A1 | 4/2008 | de Boer et al. |
| 2008/0097225 A1 | 4/2008 | Milen et al. |
| 2008/0097709 A1 | 4/2008 | de Boer et al. |
| 2008/0100837 A1 | 5/2008 | de Boer et al. |
| 2008/0139906 A1 | 6/2008 | Bussek et al. |
| 2008/0152353 A1 | 6/2008 | de Boer et al. |
| 2008/0154090 A1 | 6/2008 | Hashimshony |
| 2008/0192236 A1 | 8/2008 | Smith et al. |
| 2008/0201081 A1 | 8/2008 | Reid |
| 2008/0204762 A1 | 8/2008 | Izatt et al. |
| 2008/0218696 A1 | 9/2008 | Mir |
| 2008/0228086 A1 | 9/2008 | Ilegbusi |
| 2008/0234560 A1 | 9/2008 | Nomoto et al. |
| 2008/0265130 A1 | 10/2008 | Colomb et al. |
| 2008/0308730 A1 | 12/2008 | Vizi et al. |
| 2009/0005691 A1 | 1/2009 | Huang |
| 2009/0011948 A1 | 1/2009 | Uniu et al. |
| 2009/0044799 A1 | 2/2009 | Bangsaruntip et al. |
| 2009/0051923 A1 | 2/2009 | Andres et al. |
| 2009/0131801 A1 | 5/2009 | Suter et al. |
| 2009/0192358 A1 | 7/2009 | Yun |
| 2009/0196477 A1 | 8/2009 | Cense et al. |
| 2009/0209834 A1 | 8/2009 | Fine |
| 2009/0273777 A1 | 11/2009 | Yun et al. |
| 2009/0281390 A1 | 11/2009 | Qiunjun et al. |
| 2009/0290156 A1 | 11/2009 | Popescu et al. |
| 2009/0305309 A1 | 12/2009 | Chien et al. |
| 2009/0323056 A1 | 12/2009 | Yun et al. |
| 2010/0002241 A1 | 1/2010 | Hirose |
| 2010/0086251 A1 | 4/2010 | Xu et al. |
| 2010/0094576 A1 | 4/2010 | de Boer et al. |
| 2010/0150467 A1 | 6/2010 | Zhao et al. |
| 2010/0261995 A1 | 10/2010 | Mckenna et al. |
| 2011/0028967 A1 | 2/2011 | Rollins et al. |
| 2011/0160681 A1 | 6/2011 | Dacey, Jr. et al. |
| 2011/0218403 A1 | 9/2011 | Tearney et al. |

FOREIGN PATENT DOCUMENTS

| | | |
|---|---|---|
| DE | 4309056 | 9/1994 |
| DE | 19542955 | 5/1997 |
| DE | 10351319 | 6/2005 |
| DE | 102005034443 | 2/2007 |
| EP | 0110201 | 6/1984 |
| EP | 0251062 | 1/1988 |
| EP | 0617286 | 2/1994 |
| EP | 0590268 | 4/1994 |
| EP | 0728440 | 8/1996 |
| EP | 0933096 | 8/1999 |
| EP | 1324051 | 7/2003 |
| EP | 1426799 | 6/2004 |
| FR | 2738343 | 8/1995 |
| GB | 1257778 | 12/1971 |
| GB | 2030313 | 4/1980 |
| GB | 2209221 | 5/1989 |
| GB | 2298054 | 8/1996 |
| JP | 6073405 | 4/1985 |
| JP | 62-188001 | 6/1989 |
| JP | 04-056907 | 2/1992 |
| JP | 20040056907 | 2/1992 |
| JP | 4135550 | 5/1992 |
| JP | 4135551 | 5/1992 |
| JP | 5509417 | 11/1993 |
| JP | H8-136345 | 5/1996 |
| JP | H08-160129 | 6/1996 |
| JP | 9-230248 | 9/1997 |
| JP | 10-213485 | 8/1998 |
| JP | 10-267631 | 10/1998 |
| JP | 10-267830 | 10/1998 |
| JP | 2259617 | 10/1999 |
| JP | 2000-023978 | 1/2000 |
| JP | 2000-046729 | 2/2000 |
| JP | 2000-121961 | 4/2000 |
| JP | 2000-504234 | 4/2000 |
| JP | 2000-126116 | 5/2000 |
| JP | 2001-4447 | 1/2001 |
| JP | 2001-500026 | 1/2001 |
| JP | 2001-174404 | 6/2001 |
| JP | 2001-174744 | 6/2001 |
| JP | 2001-508340 | 6/2001 |
| JP | 2007-539336 | 6/2001 |
| JP | 2001-212086 | 8/2001 |
| JP | 2008-533712 | 8/2001 |
| JP | 2001-264246 | 9/2001 |
| JP | 2001-525580 | 12/2001 |
| JP | 2002-503134 | 1/2002 |

(56) References Cited

FOREIGN PATENT DOCUMENTS

| | | |
|---|---|---|
| JP | 2002-035005 | 2/2002 |
| JP | 2002-205434 | 2/2002 |
| JP | 2002-095663 | 4/2002 |
| JP | 2002-113017 | 4/2002 |
| JP | 2002-148185 | 5/2002 |
| JP | 2002-516586 | 6/2002 |
| JP | 2002-214128 | 7/2002 |
| JP | 2002214127 | 7/2002 |
| JP | 2003-014585 | 1/2003 |
| JP | 2003-504627 | 2/2003 |
| JP | 200300356659 | 2/2003 |
| JP | 2003-512085 | 4/2003 |
| JP | 2003-513278 | 4/2003 |
| JP | 2003-516531 | 5/2003 |
| JP | 2004-028970 | 1/2004 |
| JP | 2004-037165 | 2/2004 |
| JP | 2004-057652 | 2/2004 |
| JP | 2004-514920 | 5/2004 |
| JP | 2004-258144 | 9/2004 |
| JP | 2004-317437 | 11/2004 |
| JP | 2005-062850 | 3/2005 |
| JP | 2005-110208 | 4/2005 |
| JP | 2005-156540 | 6/2005 |
| JP | 2005-516187 | 6/2005 |
| JP | 2005-195485 | 7/2005 |
| JP | 2005-241872 | 9/2005 |
| JP | 2006-237359 | 9/2006 |
| JP | 2007-075403 | 3/2007 |
| JP | 2007-524455 | 8/2007 |
| JP | 2007271761 | 10/2007 |
| JP | 2003-102672 | 4/2012 |
| RU | 2149464 | 5/2000 |
| RU | 2213421 | 9/2003 |
| RU | 2255426 | 6/2005 |
| WO | 7900841 | 10/1979 |
| WO | 9201966 | 2/1992 |
| WO | 9216865 | 10/1992 |
| WO | 9219930 | 11/1992 |
| WO | 9303672 | 3/1993 |
| WO | 9216865 | 10/1993 |
| WO | 9533971 | 12/1995 |
| WO | 1996-02184 | 2/1996 |
| WO | 1996-04839 | 2/1996 |
| WO | 2298054 | 8/1996 |
| WO | 9628212 | 9/1996 |
| WO | 9732182 | 9/1997 |
| WO | 9800057 | 1/1998 |
| WO | 9801074 | 1/1998 |
| WO | 9814132 | 4/1998 |
| WO | 9835203 | 8/1998 |
| WO | 9838907 | 9/1998 |
| WO | 9846123 | 10/1998 |
| WO | 9848838 | 11/1998 |
| WO | 1998048846 | 11/1998 |
| WO | 9905487 | 2/1999 |
| WO | 1999044089 | 2/1999 |
| WO | 99-28856 | 6/1999 |
| WO | 9944089 | 9/1999 |
| WO | 1999-45338 | 10/1999 |
| WO | 9957507 | 11/1999 |
| WO | 2000-42906 | 7/2000 |
| WO | 2000-43730 | 7/2000 |
| WO | 0058766 | 10/2000 |
| WO | 2001-04828 | 1/2001 |
| WO | 0101111 | 1/2001 |
| WO | 0108579 | 2/2001 |
| WO | 2001027679 | 4/2001 |
| WO | 2001-033215 | 5/2001 |
| WO | 0138820 | 5/2001 |
| WO | 2001-42735 | 6/2001 |
| WO | 0142735 | 6/2001 |
| WO | 2001-82786 | 11/2001 |
| WO | 2002-037075 | 5/2002 |
| WO | 0236015 | 5/2002 |
| WO | 0238040 | 5/2002 |
| WO | 02236015 | 5/2002 |
| WO | 20020037075 | 5/2002 |
| WO | 2002-045572 | 6/2002 |
| WO | 2002-068853 | 6/2002 |
| WO | 0254027 | 7/2002 |
| WO | 2002053050 | 7/2002 |
| WO | 2002-083003 | 10/2002 |
| WO | 2002084263 | 10/2002 |
| WO | 2003-003903 | 1/2003 |
| WO | 2003-012405 | 2/2003 |
| WO | 20030013624 | 2/2003 |
| WO | 03020119 | 3/2003 |
| WO | 03052478 | 6/2003 |
| WO | 2003046495 | 6/2003 |
| WO | 2003046636 | 6/2003 |
| WO | 03062802 | 7/2003 |
| WO | 2003062802 | 7/2003 |
| WO | 20030053226 | 7/2003 |
| WO | 03-088826 | 10/2003 |
| WO | 2003105678 | 12/2003 |
| WO | 2004034869 | 4/2004 |
| WO | 2004-037068 | 5/2004 |
| WO | 2004-043251 | 5/2004 |
| WO | 2004057266 | 7/2004 |
| WO | 20040066824 | 8/2004 |
| WO | 2004-073501 | 9/2004 |
| WO | 2004088361 | 10/2004 |
| WO | 2004-100789 | 11/2004 |
| WO | 04105598 | 12/2004 |
| WO | 20050000115 | 1/2005 |
| WO | 2005-045362 | 5/2005 |
| WO | 2005-047813 | 5/2005 |
| WO | 2005047813 | 5/2005 |
| WO | 2005054780 | 6/2005 |
| WO | 2005082225 | 9/2005 |
| WO | 20050082225 | 9/2005 |
| WO | 2006004743 | 1/2006 |
| WO | 2006-020605 | 2/2006 |
| WO | 2006014392 | 2/2006 |
| WO | 2006039091 | 4/2006 |
| WO | 20060038876 | 4/2006 |
| WO | 2006-050320 | 5/2006 |
| WO | 2006-058187 | 6/2006 |
| WO | 2006059109 | 6/2006 |
| WO | 2006124860 | 11/2006 |
| WO | 2006-131859 | 12/2006 |
| WO | 2006130797 | 12/2006 |
| WO | 2007-030835 | 3/2007 |
| WO | 2007028531 | 3/2007 |
| WO | 2007038787 | 4/2007 |
| WO | 207083138 | 7/2007 |
| WO | 2007084995 | 7/2007 |
| WO | 2009-033064 | 3/2009 |
| WO | 20090153929 | 12/2009 |
| WO | 2011-055376 | 5/2011 |

OTHER PUBLICATIONS

Hariri, Lida P. et al. "Endoscopic Optical Coherence Tomography and Laser-Induced Fluorescence Spectroscopy in a Murine Colon Cancer Model", Laser in Surgery and Medicine, vol. 38, 2006, pp. 305-313.
PCT International Search Report and Written Opinion for Application No. PCT/US2006/031905 dated May 3, 2007.
PCT International Search Report and Written Opinion for Application No. PCT/US2007/060481 dated May 23, 2007.
PCT International Search Report and Written Opinion for Application No. PCT/US2007/060717 dated May 24, 2007.
PCT International Search Report and Written Opinion for Application No. PCT/US2007/060319 dated Jun. 6, 2007.
D. Yelin et al., "Three-dimensional imaging using spectral encoding heterodyne interferometry", Optics Letters, Jul. 15, 2005, vol. 30, No. 14, pp. 1794-1796.
Akiba, Masahiro et al. "En-face optical coherence imaging for three-dimensional microscopy", SPIE, 2002, pp. 8-15.
Office Action dated Aug. 10, 2007 for U.S. Appl. No. 10/997,789.

(56) References Cited

OTHER PUBLICATIONS

Office Action dated Feb. 2, 2007 for U.S. Appl. No. 11/174,425.
PCT International Search Report and Written Opinion for Application No. PCT/US2007/060657 dated Aug. 13, 2007.
Lewis, Neil E. et al., "Applications of Fourier Transform Infrared Imaging Microscopy in Neurotoxicity", Annals New York Academy of Sciences, pp. 234-246.
Joo, Chulmin et al., Spectral-domain optical coherence phase microscopy for quantitative phase-contrast imaging, Optics Letters, Aug. 15, 2005, vol. 30, No. 16, pp. 2131-2133.
Guo, Bujin et al., "Laser-based mid-infrared reflectance imaging of biological tissues", Optics Express, Jan. 12, 2004, vol. 12, No. 1, pp. 208-219.
Office Action dated Mar. 28, 2007 for U.S. Appl. No. 11/241,907.
Office Action dated May 23, 2007 for U.S. Appl. No. 10/406,751.
Office Action dated May 23, 2007 for U.S. Appl. No. 10/551,735.
PCT International Search Report and Written Opinion for Application No. PCT/US2007/061815 dated Aug. 2, 2007.
Sir Randall, John et al., "Brillouin scattering in systems of biological significance", Phil. Trans. R. Soc. Lond. A 293, 1979, pp. 341-348.
Takagi, Yasunari, "Application of a microscope to Brillouin scattering spectroscopy", Review of Scientific Instruments, No. 12, Dec. 1992, pp. 5552-5555.
Lees, S. et al., "Studies of Compact Hard Tissues and Collagen by Means of Brillouin Light Scattering", Connective Tissue Research, 1990, vol. 24, pp. 187-205.
Berovic, N. "Observation of Brillion scattering from single muscle fibers", European Biophysics Journal, 1989, vol. 17, pp. 69-74.
PCT International Search Report and Written Opinion for Application No. PCT/US2007/062465 dated Aug. 8, 2007.
Pyhtila John W. et al., "Rapid, depth-resolved light scattering measurements using Fourier domain, angle-resolved low coherence interferometry", Optics Society of America, 2004.
Pyhtila John W. et al., "Determining nuclear morphology using an improved angle-resolved low coherence interferometry system", Optics Express, Dec. 15, 2003, vol. 11, No. 25, pp. 3473-3484.
Desjardins A.E., et al., "Speckle reduction in OCT using massively-parallel detection and frequency-domain ranging", Optics Express, May 15, 2006, vol. 14, No. 11, pp. 4736-4745.
Nadkarni, Seemantini K., et al., "Measurement of fibrous cap thickness in atherosclerotic plaques by spatiotemporal analysis of laser speckle images", Journal of Biomedical Optics, vol. 11 Mar./Apr. 2006, pp. 021006-1-021006-8.
PCT International Search Report and Written Opinion for Application No. PCT/US2007/066017 dated Aug. 30, 2007.
Yamanari M. et al., "Polarization sensitive Fourier domain optical coherence tomography with continuous polarization modulation", Proc. of SPIE, vol. 6079, 2006.
Zhang Jun et al., "Full range polarization-sensitive Fourier domain optical coherence tomography", Optics Express, Nov. 29, 2004, vol. 12, No. 24, pp. 6033-6039.
European Patent Office Search report for Application No. 01991092. 6-2305 dated Jan. 12, 2006.
PCT International Search Report and Written Opinion for Application No. PCT/US2007/060670 dated Sep. 21, 2007.
J. M. Schmitt et al., "Speckle in Optical Coherence Tomography: An Overview", SPIE vol. 3726, pp. 450-461.
Fujimoto et al., "High Resolution in Vivo Intra-Arterial Imaging with Official Coherence Tomogrpahy," Official Journal of the British Cardiac Society, vol. 82, pp. 128-133 Heart, 1999.
D. Huang et al., "Optical Coherence Tomography," Science, vol. 254, pp. 1178-1181, Nov. 1991.
Tearney et al., "High-Speed Phase—and Group Delay Scanning with a Grating Based Phase Control Delay Line," Optics Letters, vol. 22, pp. 1811-1813, Dec. 1997.
Rollins, et al., "In Vivo Video Rate Optical Coherence Tomography," Optices Express, vol. 3, pp. 219-229, Sep. 1998.
Saxer, et al., "High Speed Fiber-Based Polarization-Sensitive Optical Coherence Tomography of in Vivo Human Skin," Optical Society of America, vol. 25, pp. 1355-1357, Sep. 2000.
Oscar Eduardo Martinez, "3000 Times Grating Compress or with Positive Group Velocity Dispersion," IEEE, vol. QE-23, pp. 59-64, Jan. 1987.
Kulkarni, et al., "Image Enhancement in Optical Coherence Tomography Using Deconvolution," Electronics Letters, vol. 33, pp. 1365-1367, Jul. 1997.
Bashkansky, et al., "Signal Processing for Improving Field Cross-Correlation Function in Optical Coherence Tomography," Optics & Photonics News, vol. 9, pp. 8137-8138, May 1998.
Yung et al., "Phase-Domain Processing of Optical Coherence Tomography Images," Journal of Biomedical Optics, vol. 4, pp. 125-136, Jan. 1999.
Tearney, et al., "In Vivo Endoscopic Optical Biopsy with Optical Coherence Tomography," Science, vol. 276, Jun. 1997.
W. Drexler et al., "In Vivo Ultrahigh-Resolution Optical Coherence Tomography," Optics Letters vol. 24, pp. 1221-1223, Sep. 1999.
Nicusor V. Iftimia et al., "A Portable, Low Coherence Interferometry Based Instrument for Fine Needle Aspiration Biopsy Guidance," Accepted to Review of Scientific Instruments, 2005.
Abbas, G.L., V.W.S. Chan et al., "Local-Oscillator Excess-Noise Suppression for Homodyne and Heterodyne-Detection," Optics Letters, vol. 8, pp. 419-421, Aug. 1983 issue.
Agrawal, G.P., "Population Pulsations and Nondegenerate 4-Wave Mixing in Semiconductor-Lasers and Amplifiers," Journal of the Optical Society of America B-Optical Physics, vol. 5, pp. 147-159, Jan. 1998.
Andretzky, P. et al., "Optical Coherence Tomography by Spectral Radar: Improvement of Signal-to-Noise Ratio," The International Society for Optical Engineering, USA, vol. 3915, 2000.
Ballif, J. et al., "Rapid and Scalable Scans at 21 m/s in optical Low-Coherence Reflectometry," Optics Letters, vol. 22, pp. 757-759, Jun. 1997.
Barfuss H. et al., "Modified Optical Frequency-Domain Reflectometry with High-Spatial-Resolution for Components of Integrated Optic Systems," Journal of Lightwave Technology, vol. 7, pp. 3-10, Jan. 1989.
Beaud, P. et al., "Optical Reflectometry with Micrometer Resolution for the Investigation of Integrated Optical-Devices," Leee Journal of Quantum Electronics, vol. 25, pp. 755-759, Apr. 1989.
Bouma, Brett et al., "Power-Efficient Nonreciprocal Interferometer and Linear-Scanning Fiber-Optic Catheter for Optical Coherence Tomography," Optics Letters, vol. 24, pp. 531-533, Apr. 1999.
Brinkmeyer, E. et al., "Efficient Algorithm for Non-Equidistant Interpolation of Sampled Data," Electronics Letters, vol. 28, p. 693, Mar. 1992.
Brinkmeyer, E. et al., "High-Resolution OCDR in Dispersive Wave-Guides," Electronics Letters, vol. 26, pp. 413-414, Mar. 1990.
Chinn, S.R. et al., "Optical Coherence Tomography Using a Frequency-Tunable Optical Source," Optics Letters, vol. 22, pp. 340-342, Mar. 1997.
Danielson, B.L. et al., "Absolute Optical Ranging Using Low Coherence Interferometry," Applied Optics, vol.30, p. 2975, Jul. 1991.
Dorrer, C. et al., "Spectral Resolution and Sampling Issues in Fourier-Transform Spectral Interferometry," Journal of the Optical Society of America B-Optical Physics, vol. 17, pp. 1795-1802, Oct. 2000.
Dudley, J.M. et al., "Cross-Correlation Frequency Resolved Optical Gating Analysis of Broadband Continuum Generation in Photonic Crystal Fiber: Simulations and Experiments," Optics Express, vol. 10, p. 1215, Oct. 2002.
Eickhoff, W. et al., "Optical Frequency-Domain Reflectometry in Single-Mode Fiber," Applied Physics Letters, vol. 39, pp. 693-695, 1981.
Fercher, Adolf"Optical Coherence Tomography," Journal of Biomedical Optics, vol. 1, pp. 157-173, Apr. 1996.
Ferreira, L.A. et al., "Polarization-Insensitive Fiberoptic White-Light Interferometry," Optics Communications, vol. 114, pp. 386-392, Feb. 1995.

(56) References Cited

OTHER PUBLICATIONS

Fujii, Yohji, "High-Isolation Polarization-Independent Optical Circulator", *Journal of Lightwave Technology*, vol. 9, pp. 1239-1243, Oct. 1991.
Glance, B., "Polarization Independent Coherent Optical Receiver," *Journal of Lightwave Technology*, vol. LT-5, p. 274, Feb. 1987.
Glombitza, U., "Coherent Frequency-Domain Reflectometry for Characterization of Single-Mode Integrated-Optical Wave-Guides," *Journal of Lightwave Technology*, vol. 11, pp. 1377-1384, Aug. 1993.
Golubovic, B. et al., "Optical Frequency-Domain Reflectometry Using Rapid Wavelength Tuning of a Cr4+:Forsterite Laser," *Optics Letters*, vol. 11, pp. 1704-1706, Nov. 1997.
Haberland, U. H. P. et al., "Chirp Optical Coherence Tomography of Layered Scattering Media," *Journal of Biomedical Optics*, vol. 3, pp. 259-266, Jul. 1998.
Hammer, Daniel X. et al., "Spectrally Resolved White-Light Interferometry for Measurement of Ocular Dispersion," *Journal of the Optical Society of America A—Optics Image Science and Vision*, vol. 16, pp. 2092-2102, Sep. 1999.
Harvey, K. C. et al., "External-Cavity Diode-Laser Using a Grazing-Incidence Diffraction Grating," *Optics Letters*, vol. 16, pp. 910-912, Jun. 1991.
Hausler, Gerd et al., "'Coherence Radar' and 'Spectral Radar' New Tools for Dermatological Diagnosis," *Journal of Biomedical Optics*, vol. 3, pp. 21-31, Jan. 1998.
Hee, Michael R. et al., "Polarization-Sensitive Low-Coherence Reflectometer for Birefringence Characterization and Ranging," *Journal of the Optical Society of America B (Optical Physics)*, vol. 9, p. 903-908, Jun. 1992.
Hotate Kazuo et al., "Optical Coherence Domain Reflectometry by Synthesis of Coherence Function," *Journal of Lightwave Technology*, vol. 11, pp. 1701-1710, Oct. 1993.
Inoue, Kyo et al., "Nearly Degenerate 4-Wave-Mixing in a Traveling-Wave Semiconductor-Laser Amplifier," *Applied Physics Letters*, vol. 51, pp. 1051-1053, 1987.
Ivanov, A. P. et al., "New Method for High-Range Resolution Measurements of Light Scattering in Optically Dense Inhomogeneous Media," *Optics Letters*, vol. 1, pp. 226-228, Dec. 1977.
Ivanov, A. P. et al., "Interferometric Study of the Spatial Structure of a Light-Scattering Medium," *Journal of Applied Spectroscopy*, vol. 28, pp. 518-525, 1978.
Kazovsky, L. G. et al., "Heterodyne Detection Through Rain, Snow, and Turbid Media: Effective Receiver Size at Optical Through Millimeter Wavelenghths," *Applied Optics*, vol. 22, pp. 706-710, Mar. 1983.
Kersey, A. D. et al., "Adaptive Polarization Diversity Receiver Configuration for Coherent Optical Fiber Communications," *Electronics Letters*, vol. 25, pp. 275-277, Feb. 1989.
Kohlhaas, Andreas et al., "High-Resolution OCDR for Testing Integrated-Optical Waveguides: Dispersion-Corrupted Experimental Data Corrected by a Numerical Algorithm," *Journal of Lightwave Technology*, vol. 9, pp. 1493-1502, Nov. 1991.
Larkin, Kieran G., "Efficient Nonlinear Algorithm for Envelope Detection in White Light Interferometry," *Journal of the Optical Society of America A—Optics Image Science and Vision*, vol. 13, pp. 832-843, Apr. 1996.
Leitgeb, R. et al., "Spectral measurement of Absorption by Spectroscopic Frequency-Domain Optical Coherence Tomography," *Optics Letters*, vol. 25, pp. 820-822, Jun. 2000.
Lexer, F. et al., "Wavelength-Tuning Interferometry of Intraocular Distances," *Applied Optics*,vol. 36, pp. 6548-6553, Sep. 1997.
Mitsui, Takahisa, "Dynamic Range of Optical Reflectometry with Spectral Interferometry," *Japanese Journal of Applied Physics Part 1—Regular Papers Short Notes & Review Papers*, vol. 38, pp. 6133-6137, 1999.
Naganuma, Kazunori et al., "Group-Delay Measurement Using the Fourier-Transform of an Interferometric Cross-Correlation Generated by White Light," *Optics Letters*, vol. 15, pp. 393-395, Apr. 1990.
Okoshi,Takanori, "Polarization-State Control Schemes for Heterodyne or Homodyne Optical Fiber Communications," *Journal of Lightwave Technology*, vol. LT-3, pp. 1232-1237, Dec. 1995.
Passy, R. et al., "Experimental and Theoretical Investigations of Coherent OFDR with Semiconductor-Laser Sources," *Journal of Lightwave Technology*, vol. 12, pp. 1622-1630, Sep. 1994.
Podoleanu, Adrian G., "Unbalanced Versus Balanced Operation in an Optical Coherence Tomography System," *Applied Optics*, vol. 39, pp. 173-182, Jan. 2000.
Price, J. H. V. et al., "Tunable, Femtosecond Pulse Source Operating in the Range 1.06-1.33 mu m Based on an Yb3+-doped Holey Fiber Amplifier," *Journal of the Optical Society of America B-Optical Physics*, vol. 19, pp. 1286-1294, Jun. 2002.
Schmitt, J. M. et al, "Measurement of Optical-Properties of Biological Tissues By Low-Coherence Reflectometry," *Applied Optics*, vol. 32, pp. 6032-6042, Oct. 1993.
Silberberg, Y. et al., "Passive-Mode Locking of a Semiconductor Diode-Laser," *Optics Letters*, vol. 9, pp. 507-509, Nov. 1984.
Smith, L. Montgomery et al., "Absolute Displacement Measurements Using Modulation of the Spectrum of White-Light in a Michelson Interferometer," *Applied Optics*, vol. 28, pp. 3339-3342, Aug. 1989.
Sonnenschein, C. M. et al., "Signal-To-Noise Relationships for Coaxial Systems that Heterodyne Backscatter from Atmosphere," *Applied Optics*, vol. 10, pp. 1600-1604, Jul. 1971.
Sorin, W. V. et al., "Measurement of Rayleigh Backscattering at 1.55 mu m with 32 mu m Spatial Resolution," *IEEE Photonics Technology Letters*, vol. 4, pp. 374-376, Apr. 1992.
Sorin, W. V. et al., "A Simple Intensity Noise-Reduction Technique for Optical Low-Coherence Reflectometry," *IEEE Photonics Technology Letters*, vol. 4, pp. 1404-1406, Dec. 1992.
Swanson, E. A. et al., "High-Speed Optical Coherence Domain Reflectometry," *Optics Letters*, vol. 17, pp. 151-153, Jan. 1992.
Takada, K. et al., "High-Resolution OFDR with Incorporated Fiberoptic Frequency Encoder," *IEEE Photonics Technology Letters*, vol. 4, pp. 1069-1072, Sep. 1992.
Takada, Kazumasa et al., "Narrow-Band light Source with Acoustooptic Tunable Filter for Optical Low-Coherence Reflectometry," *IEEE Photonics Technology Letters*, vol. 8, pp. 658-660, May 1996.
Takada, Kazumasa et al., "New Measurement System for Fault Location in Optical Wave-Guide Devices Based on an Interometric-Technique," *Applied Optics*, vol. 26, pp. 1603-1606, May 1987.
Tateda, Mitsuhiro et al., "Interferometric Method for Chromatic Dispersion Measurement in a Single-Mode Optical Fiber," *IEEE Journal of Quantum Electronics*, vol. 17, pp. 404-407, Mar. 1981.
Toide, M. et al., "Two-Dimensional Coherent Detection Imaging in Multiple Scattering Media Based the Directional Resolution Capability of the Optical Heterodyne Method," *Applied Physics B (Photophysics and Laser Chemistry)*, vol. B52, pp. 391-394, 1991.
Trutna, W. R. et al., "Continuously Tuned External-Cavity Semiconductor-Laser," *Journal of Lightwave Technology*, vol. 11, pp. 1279-1286, Aug. 1993.
Uttam, Deepak et al., "Precision Time Domain Reflectometry in Optical Fiber Systems Using a Frequency Modulated Continuous Wave Ranging Technique," *Journal of Lightwave Technology*, vol. 3, pp. 971-977, Oct. 1985.
Von Der Weid, J. P. et al., "On the Characterization of Optical Fiber Network Components with Optical Frequency Domain Reflectometry," *Journal of Lightwave Technology*, vol. 15, pp. 1131-1141, Jul. 1997.
Wysocki, P.F. et al., "Broad-Spectrum, Wavelength-Swept, Erbium-Doped Fiber Laser at 1.55-Mu-M," *Optics Letters*, vol. 15, pp. 879-881, Aug. 1990.
Youngquist, Robert C. et al., "Optical Coherence-Domain Reflectometry—A New Optical Evaluation Technique," *Optics Letters*, vol. 12, pp. 158-160, Mar. 1987.
Yun, S. H. et al., "Wavelength-Swept Fiber Laser with Frequency Shifted Feedback and Resonantly Swept Intra-Cavity Acoustooptic in Tunable Filter," *IEEE Journal of Selected Topics in Quantum Electronics*, vol. 3, pp. 1087-1096, Aug. 1997.
Yun, S. H. et al., "Interrogation of Fiber Grating Sensor Arrays with a Wavelength-Swept Fiber Laser," *Optics Letters*, vol. 23, pp. 843-845, Jun. 1998.

(56) References Cited

OTHER PUBLICATIONS

Yung, K. M., "Phase-Domain Processing of Optical Coherence Tomography Images," *Journal of Biomedical Optics*, vol. 4, pp. 125-136, Jan. 1999.

Zhou, Xiao-Qun et al., "Extended-Range FMCW Reflectometry Using an optical Loop with a Frequency Shifter," *IEEE Photonics Technology Letters*, vol. 8, pp. 248-250, Feb. 1996.

Zorabedian, Paul et al., "Tuning Fidelity of Acoustooptically Controlled External Cavity Semiconductor-Lasers," *Journal of Lightwave Technology*, vol. 13, pp. 62-66, Jan. 1995.

Victor S. Y. Lin et al., "A Porous Silicon-Based Optical Interferometric Biosensor," *Science Magazine*, vol. 278, pp. 840-843, Oct. 31, 1997.

De Boer, Johannes F. et al., "Review of Polarization Sensitive Optical Coherence Tomography and Stokes Vector Determination," *Journal of Biomedical Optics*, vol. 7, No. 3, Jul. 2002, pp. 359-371.

Jiao, Shuliang et al., "Depth-Resolved Two-Dimensional Stokes Vectors of Backscattered Light and Mueller Matrices of Biological Tissue Measured with Optical Coherence Tomography," *Applied Optics*, vol. 39, No. 34, Dec. 1, 2000, pp. 6318-6324.

Park, B. Hyle et al., "In Vivo Burn Depth Determination by High-Speed Fiber-Based Polarization Sensitive Optical Coherence Tomography," *Journal of Biomedical Optics*, vol. 6 No. 4, Oct. 2001, pp. 474-479.

Roth, Jonathan E. et al., "Simplified Method for Polarization-Sensitive Optical Coherence Tomography," *Optics Letters*, vol. 26, No. 14, Jul. 15, 2001, pp. 1069-1071.

Hitzenberger, Christopher K. et al., "Measurement and Imaging of Birefringence and Optic Axis Orientation by Phase Resolved Polarization Sensitive Optical Coherence Tomography," *Optics Express*, vol. 9, No. 13, Dec. 17, 2001, pp. 780-790.

Wang, Xueding et al., "Propagation of Polarized Light in Birefringent Turbid Media: Time-Resolved Simulations," Optical Imaging Laboratory, Biomedical Engineering Program, Texas A&M University.

Wong, Brian J.F. et al., "Optical Coherence Tomography of the Rat Cochlea," *Journal of Biomedical Optics*, vol. 5, No. 4, Oct. 2000, pp. 367-370.

Yao, Gang et al., "Propagation of Polarized Light in Turbid Media: Simulated Animation Sequences," *Optics Express*, vol. 7, No. 5, Aug. 28, 2000, pp. 198-203.

Wang, Xiao-Jun et al., "Characterization of Dentin and Enamel by Use of Optical Coherence Tomography," *Applied Optics*, vol. 38, No. 10, Apr. 1, 1999, pp. 2092-2096.

De Boer, Johannes F. et al., "Determination of the Depth-Resolved Stokes Parameters of Light Backscattered from Turbid Media by Use of Polarization-Sensitive Optical Coherence Tomography," *Optics Letters*, No. 5, Mar. 1, 1999, pp. 300-302.

Ducros, Mathieu G. et al., "Polarization Sensitive Optical Coherence Tomography of the Rabbit Eye," *IEEE Journal of Selected Topics in Quantum Electronics*, vol. 5, No. 4, Jul./Aug. 1999, pp. 1159-1167.

Groner, Warren et al., "Orthogonal Polarization Spectral Imaging: A New Method for Study of the Microcirculation," *Nature Medicine Inc.*, vol. 5 No. 10, Oct. 1999, pp. 1209-1213.

De Boer, Johannes F. et al., "Polarization Effects in Optical Coherence Tomography of Various Viological Tissues," *IEEE Journal of Selected Topics in Quantum Electronics*, vol. 5, No. 4, Jul./Aug. 1999, pp. 1200-1204.

Yao, Gang et al., "Two-Dimensional Depth-Resolved Mueller Matrix Characterization of Biological Tissue by Optical Coherence Tomography," *Optics Letters*, Apr. 15, 1999, vol. 24, No. 8, pp. 537-539.

Lu, Shih-Yau et al., "Homogeneous and Inhomogeneous Jones Matrices," *J. Opt. Soc. Am. A.*, vol. 11, No. 2, Feb. 1994, pp. 766-773.

Bickel, S. William et al., "Stokes Vectors, Mueller Matrices, and Polarized Scattered Light," *Am. J. Phys.*, vol. 53, No. 5, May 1985 pp. 468-478.

Bréhonnet, F. Le Roy et al., "Optical Media and Target Characterization by Mueller Matrix Decomposition," *J. Phys. D: Appl. Phys.* 29, 1996, pp. 34-38.

Cameron, Brent D. et al., "Measurement and Calculation of the Two-Dimensional Backscattering Mueller Matrix of a Turbid Medium," *Optics Letters*, vol. 23, No. 7, Apr. 1, 1998, pp. 485-487.

De Boer, Johannes F. et al., "Two-Dimensional Birefringence Imaging in Biological Tissue by Polarization-Sensitive Optical Coherence Tomography," *Optics Letters*, vol. 22, No. 12, Jun. 15, 1997, pp. 934-936.

De Boer, Johannes F. et al., "Imaging Thermally Damaged Tissue by Polarization Sensitive Optical Coherence Tomography," *Optics Express*, vol. 3, No. 6, Sep. 14, 1998, pp. 212-218.

Everett, M.J. et al., "Birefringence Characterization of Biological Tissue by Use of Optical Coherence Tomography," *Optics Letters*, vol. 23, No. 3, Feb. 1, 1998, pp. 228-230.

Hee, Michael R. et al., "Polarization-Sensitive Low-Coherence Reflectometer for Birefringence Characterization and Ranging," *J. Opt. Soc. Am. B.*, vol. 9, No. 6, Jun. 1992, pp. 903-908.

Barakat, Richard, "Statistics of the Stokes Parameters," *J. Opt. Soc. Am. B.*, vol. 4, No. 7, Jul. 1987, pp. 1256-1263.

Schmitt, J.M. et al., "Cross-Polarized Backscatter in Optical Coherence Tomography of Biological Tissue," *Optics Letters*, vol. 23, No. 13, Jul. 1, 1998, pp. 1060-1062.

Schoenenberger, Klaus et al., "Mapping of Birefringence and Thermal Damage in Tissue by use of Polarization-Sensitive Optical Coherence Tomography," *Applied Optics*, vol. 37, No. 25, Sep. 1, 1998, pp. 6026-6036.

Pierce, Mark C. et al., "Simultaneous Intensity, Birefringence, and Flow Measurements with High-Speed Fiber-Based Optical Coherence Tomography," *Optics Letters*, vol. 27, No. 17, Sep. 1, 2002, pp. 1534-1536.

De Boer, Johannes F. et al., "Review of Polarization Sensitive Optical Coherence Tomography and Stokes Vector Determination," *Journal of Biomedical Optics*, Jul. 2002, vol. 7, No. 3, pp. 359-371.

Fried, Daniel et al., "Imaging Caries Lesions and Lesion Progression with Polarization Sensitive Optical Coherence Tomography," *Journal of Biomedical Optics*, vol. 7, No. 4, Oct. 2002, pp. 618-627.

Jiao, Shuliang et al., "Two-Dimensional Depth-Resolved Mueller Matrix of Biological Tissue Measured with Double-Beam Polarization-Sensitive Optical Coherence Tomography," *Optics Letters*, vol. 27, No. 2, Jan. 15, 2002, pp. 101-103.

Jiao, Shuliang et al., "Jones-Matrix Imaging of Biological Tissues with Quadruple-Channel Optical Coherence Tomography," *Journal of Biomedical Optics*, vol. 7, No. 3, Jul. 2002, pp. 350-358.

Kuranov, R.V. et al., "Complementary Use of Cross-Polarization and Standard OCT for Differential Diagnosis of Pathological Tissues," *Optics Express*, vol. 10, No. 15, Jul. 29, 2002, pp. 707-713.

Cense, Barry et al., "In Vivo Depth-Resolved Birefringence Measurements of the Human Retinal Nerve Fiber Layer by Polarization-Sensitive Optical Coherence Tomography," *Optics Letters*, vol. 27, No. 18, Sep. 15, 2002, pp. 1610-1612.

Ren, Hongwu et al., "Phase-Resolved Functional Optical Coherence Tomography: Simultaneous Imaging of In Situ Tissue Structure, Blood Flow Velocity, Standard Deviation, Birefringence, and Stokes Vectors in Human Skin," *Optics Letters*, vol. 27, No. 19, Oct. 1, 2002, pp. 1702-1704.

Tripathi, Renu et al., "Spectral Shaping for Non-Gaussian Source Spectra in Optical Coherence Tomography," *Optics Letters*, vol. 27, No. 6, Mar. 15, 2002, pp. 406-408.

Yasuno, Y. et al., "Birefringence Imaging of Human Skin by Polarization-Sensitive Spectral Interferometric Optical Coherence Tomography," *Optics Letters*, vol. 27, No. 20, Oct. 15, 2002 pp. 1803-1805.

White, Brian R. et al., "In Vivo Dynamic Human Retinal Blood Flow Imaging Using Ultra-High-Speed Spectral Domain Optical Doppler Tomography," *Optics Express*, vol. 11, No. 25, Dec. 15, 2003, pp. 3490-3497.

De Boer, Johannes F. et al., "Improved Signal-to-Noise Ratio in Spectral-Domain Compared with Time-Domain Optical Coherence Tomography," *Optics Letters*, vol. 28, No. 21, Nov. 1, 2003, pp. 2067-2069.

(56) References Cited

OTHER PUBLICATIONS

Jiao, Shuliang et al., "Optical-Fiber-Based Mueller Optical Coherence Tomography," *Optics Letters*, vol. 28, No. 14, Jul. 15, 2003, pp. 1206-1208.
Jiao, Shuliang et al., "Contrast Mechanisms in Polarization-Sensitive Mueller-Matrix Optical Coherence Tomography and Application in Burn Imaging," *Applied Optics*, vol. 42, No. 25, Sep. 1, 2003, pp. 5191-5197.
Moreau, Julien et al., "Full-Field Birefringence Imaging by Theraml-Light Polarization-Sensitive Optical Coherence Tomography. I. Theory," *Applied Optics*, vol. 42, No. 19, Jul. 1, 2003, pp. 3800-3810.
Moreau, Julien et al., "Full-Field Birefringence Imaging by Thermal-Light Polarization-Sensitive Optical Coherence Tomography. II. Instruments and Results," *Applied Optics*, vol. 42, No. 19, Jul. 1, 2003, pp. 3811-3818.
Morgan, Stephen P. et al., "Surface-Reflection Elimination in Polarization Imaging of Superficial Tissue," *Optics Letters*, vol. 28, No. 2, Jan. 15, 2003, pp. 114-116.
Oh, Jung-Taek et al., "Polarization-Sensitive Optical Coherence Tomography for Photoelasticity Testing of Glass/Epoxy Composites," *Optics Express*, vol. 11, No. 14, Jul. 14, 2003, pp. 1669-1676.
Park, B. Hyle et al., "Real-Time Multi-Functional Optical Coherence Tomography," *Optics Express*, vol. 11, No. 7, Apr. 7, 2003, pp. 782-793.
Shribak, Michael et al., "Techniques for Fast and Sensitive Measurements of Two-Dimensional Birefringence Distributions," *Applied Optics*, vol. 42, No. 16, Jun. 1, 2003, pp. 3009-3017.
Somervell, A.R.D. et al., "Direct Measurement of Fringe Amplitude and Phase Using a Heterodyne Interferometer Operating in Broadband Light," *Elsevier, Optics Communications*, Oct. 2003.
Stiffer, D. et al., "Polarisation-Sensitive Optical Coherence Tomography for Material Characterisation and Strain-Field Mapping," Applied Physics A 76, Materials Science & Processing, Jan. 2003, pp. 947-951.
Dave, Digant P. et al., "Polarization-Maintaining Fiber-Based Optical Low-Coherence Reflectometer for Characterization and Ranging of Birefringence," *Optics Letters*, vol. 28, No. 19, Oct. 1, 2003, pp. 1775-1777.
Yang, Ying et al., "Observations of Birefringence in Tissues from Optic-Fibre-Based Optical Coherence Tomography," *Measurement Science and Technology*, Nov. 2002, pp. 41-46.
Yun, S.H. et al., "High-Speed Optical Frequency-Domain Imaging," *Optics Express*, vol. 11, No. 22, Nov. 3, 2003, pp. 2953-2963.
Yun, S.H. et al., "High-Speed Spectral-Domain Optical Coherence Tomography at 1.3 μm Wavelength," *Optics Express*, vol. 11, No. 26, Dec. 29, 2003, pp. 3598-3604.
Zhang, Jun et al., "Determination of Birefringence and Absolute Optic Axis Orientation Using Polarization-Sensitive Optical Coherence Tomography with PM Fibers," *Optics Express*, vol. 11, No. 24, Dec. 1, 2003, pp. 3262-3270.
Pircher, Michael et al., "Three Dimensional Polarization Sensitive OCT of Human Skin in Vivo," 2004, *Optical Society of America*.
Götzinger, Erich et al., "Measurement and Imaging of Birefringent Properties of the Human Cornea with Phase-Resolved, Polarization-Sensitive Optical Coherence Tomography," *Journal of Biomedical Optics*, vol. 9, No. 1, Jan./Feb. 2004, pp. 94-102.
Guo, Shuguang et al., "Depth-Resolved Birefringence and Differential Optical Axis Orientation Measurements with Finer-based Polarization-Sensitive Optical Coherence Tomography," *Optics Letters*, vol. 29, No. 17, Sep. 1, 2004, pp. 2025-2027.
Huang, Xiang-Run et al.,"Variation of Peripapillary Retinal Nerve Fiber Layer Birefringence in Normal Human Subjects," *Investigative Ophthalmology & Visual Science*, vol. 45, No. 9, Sep. 2004, pp. 3073-3080.
Matcher, Stephen J. et al., "The Collagen Structure of Bovine Intervertebral Disc Studed Using Polarization-Sensitive Optical Coherence Tomography," *Physics in Medicine and Biology*, 2004, pp. 1295-1306.

Nassif, Nader et al., "In Vivo Human Retinal Imaging by Ultrahigh-Speed Spectral Domain Optical Coherence Tomography," *Optics Letters*, vol. 29, No. 5, Mar. 1, 2004, pp. 480-482.
Nassif, N.A. et al., "In Vivo High-Resolution Video-Rate Spectral-Domain Optical Coherence Tomography of the Human Retina and Optic Nerve," *Optics Express*, vol. 12, No. 3, Feb. 9, 2004, pp. 367-376.
Park, B. Hyle et al., Comment on "Optical-Fiber-Based Mueller Optical Coherence Tomography," *Optics Letters*, vol. 29, No. 24, Dec. 15, 2004, pp. 2873-2874.
Park, B. Hyle et al., "Jones Matrix Analysis for a Polarization-Sensitive Optical Coherence Tomography System Using Fiber-Optic Components," *Optics Letters*, vol. 29, No. 21, Nov. 1, 2004, pp. 2512-2514.
Pierce, Mark C. et al., "Collagen Denaturation can be Quantified in Burned Human Skin Using Polarization-Sensitive Optical Coherence Tomography," *Elsevier, Burns*, 2004, pp. 511-517.
Pierce, Mark C. et al., "Advances in Optical Coherence Tomography Imaging for Dermatology," *The Society for Investigative Dermatology, Inc.* 2004, pp. 458-463.
Pierce, Mark C. et al., "Birefringence Measurements in Human Skin Using Polarization-Sensitive Optical Coherence Tomography," *Journal of Biomedical Optics*, vol. 9, No. 2, Mar./Apr. 2004, pp. 287-291.
Cense, Barry et al., "In Vivo Birefringence and Thickness Measurements of the Human Retinal Nerve Fiber Layer Using Polarization-Sensitive Optical Coherence Tomography," *Journal of Biomedical Optics*, vol. 9, No. 1, Jan./Feb. 2004, pp. 121-125.
Pircher, Michael et al., "Imaging of Polarization Properties of Human Retina in Vivo with Phase Resolved Transversal PS-OCT," *Optics Express*, vol. 12, No. 24, Nov. 29, 2004 pp. 5940-5951.
Pircher, Michael et al., "Transversal Phase Resolved Polarization Sensitive Optical Coherence Tomography," *Physics in Medicine & Biology*, 2004, pp. 1257-1263.
Srinivas, Shyam M. et al., "Determination of Burn Depth by Polarization-Sensitive Optical Coherence Tomography," *Journal of Biomedical Optics*, vol. 9, No. 1, Jan./Feb. 2004, pp. 207-212.
Strasswimmer, John et al., "Polarization-Sensitive Optical Coherence Tomography of Invasive Basel Cell Carcinoma," *Journal of Biomedical Optics*, vol. 9, No. 2, Mar./Apr. 2004, pp. 292-298.
Todorovič, Miloš et al., "Determination of Local Polarization Properties of Biological Samples in the Presence of Diattenuation by use of Mueller Optical Coherence Tomography," *Optics Letters*, vol. 29, No. 20, Oct. 15, 2004, pp. 2402-2404.
Yasuno, Yoshiaki et al., "Polarization-Sensitive Complex Fourier Domain Optical Coherence Tomography for Jones Matrix Imaging of Biological Samples," Applied Physics Letters, vol. 85, No. 15, Oct. 11, 2004, pp. 3023-3025.
Acioli, L. H., M. Ulman, et al. (1991). "Femtosecond Temporal Encoding in Barium-Titanate." *Optics Letters* 16(24): 1984-1986.
Aigouy, L., A. Lahrech, et al. (1999). "Polarization effects in apertureless scanning near-field optical microscopy: an experimental study." *Optics Letters* 24(4): 187-189.
Akiba, M., K. P. Chan, et al. (2003). "Full-field optical coherence tomography by two-dimensional heterodyne detection with a pair of CCD cameras." *Optics Letters* 28(10): 816-818.
Akkin, T., D. P. Dave, et al. (2004). "Detection of neural activity using phase-sensitive optical low-coherence reflectometry." *Optics Express* 12(11): 2377-2386.
Akkin, T., D. P. Dave, et al. (2003). "Surface analysis using phase sensitive optical low coherence reflectometry." *Lasers in Surgery and Medicine*: 4-4.
Akkin, T., D. P. Dave, et al. (2003). "Imaging tissue response to electrical and photothermal stimulation with nanometer sensitivity." *Lasers in Surgery and Medicine* 33(4): 219-225.
Akkin, T., T. E. Milner, et al. (2002). "Phase-sensitive measurement of birefringence change as an indication of neural functionality and diseases." *Lasers in Surgery and Medicine*: 6-6.
Andretzky, P., Lindner, M.W., Herrmann, J.M., Schultz, A., Konzog, M., Kieswetter, F., Haeusler, G. (1999). "Optical coherence tomography by 'spectral radar': Dynamic range estimation and in vivo measurements of skin." *Proceedings of SPIE—The International Society for Optical Engineering* 3567: pp. 78-87.

(56) References Cited

OTHER PUBLICATIONS

Antcliff, R. J., T. J. ffytche, et al. (2000). "Optical coherence tomography of melanocytoma." *American Journal of Ophthalmology* 130(6): 845-7.

Antcliff, R. J., M. R. Stanford, et al. (2000). "Comparison between optical coherence tomography and fundus fluorescein angiography for the detection of cystoid macular edema in patients with uveitis." *Ophthalmology* 107(3): 593-9.

Anvari, B., T. E. Milner, et al. (1995). "Selective Cooling of Biological Tissues—Application for Thermally Mediated Therapeutic Procedures." *Physics in Medicine and Biology* 40(2): 241-252.

Anvari, B., B. S. Tanenbaum, et al. (1995). "A Theoretical-Study of the Thermal Response of Skin to Cryogen Spray Cooling and Pulsed-Laser Irradiation—Implications for Treatment of Port-Wine Stain Birthmarks." *Physics in Medicine and Biology* 40(9): 1451-1465.

Arend, O., M. Ruffer, et al. (2000). "Macular circulation in patients with diabetes mellitus with and without arterial hypertension." *British Journal of Ophthalmology* 84(12): 1392-1396.

Arimoto, H. and Y. Ohtsuka (1997). "Measurements of the complex degree of spectral coherence by use of a wave-front-folded interferometer." *Optics Letters* 22(13): 958-960.

Azzolini, C., F. Patelli, et al. (2001). "Correlation between coherence tomography data and biomicroscopic interpretation of idiopathic macular hole." *American Journal of Ophthalmology* 132(3): 348-55.

Baba, T., K. Ohno-Matsui, et al. (2002). "Optical coherence tomography of choroidal neovascularization in high myopia." *Acta Ophthalmoloqica Scandinavica* 80(1): 82-7.

Bail, M. A. H., Gerd; Herrmann, Juergen M.; Lindner, Michael W.; Ringler, R. (1996). "Optical coherence tomography with the "spectral radar": fast optical analysis in volume scatterers by short-coherence interferometry." *Proc. SPIE*, 2925: p. 298-303.

Baney, D. M. and W. V. Sorin (1993). "Extended-Range Optical Low-Coherence Reflectometry Using a Recirculating Delay Technique." *Ieee Photonics Technology Letters* 5(9): 1109-1112.

Baney, D. M., B. Szafraniec, et al. (2002). "Coherent optical spectrum analyzer." *Ieee Photonics Technology Letters* 14(3): 355-357.

Barakat, R. (1981). "Bilinear Constraints between Elements of the 4by4 Mueller-Jones Transfer-Matrix of Polarization Theory." *Optics Communications* 38(3): 159-161.

Barakat, R. (1993). "Analytic Proofs of the Arago-Fresnel Laws for the Interference of Polarized-Light." *Journal of the Optical Society of America a—Optics Image Science and Vision* 10(1): 180-185.

Barbastathis, G. and D. J. Brady (1999). "Multidimensional tomographic imaging using volume holography." *Proceedings of the Ieee* 87(12): 2098-2120.

Bardal, S., A. Kamal, et al. (1992). "Photoinduced Birefringence in Optical Fibers—a Comparative-Study of Low-Birefringence and High-Birefringence Birefringence Fibers." *Optics Letters* 17(6): 411-413.

Barsky, S. H., S. Rosen, et al. (1980). "Nature and Evolution of Port Wine Stains—Computer-Assisted Study." *Journal of Investigative Dermatology* 74(3): 154-157.

Barton, J. K., J. A. Izatt, et al. (1999). "Three-dimensional reconstruction of blood vessels from in vivo color Doppler optical coherence tomography images." *Dermatology* 198(4): 355-361.

Barton, J. K., A. Rollins, et al. (2001). "Photothermal coagulation of blood vessels: a comparison of high-speed optical coherence tomography and numerical modelling." *Physics in Medicine and Biology* 46.

Barton, J. K., A. J. Welch, et al. (1998). "Investigating pulsed dye laser-blood vessel interaction with color Doppler optical coherence tomography." *Optics Express* 3.

Bashkansky, M., M. D. Duncan, et al. (1997). "Subsurface defect detection in ceramics by high-speed high-resolution optical coherent tomography." *Optics Letters* 22 (1): 61-63.

Bashkansky, M. and J. Reintjes (2000). "Statistics and reduction of speckle in optical coherence tomography." *Optics Letters* 25(8): 545-547.

Baumgartner, A., S. Dichtl, et al. (2000). "Polarization-sensitive optical coherence tomography of dental structures." *Caries Research* 34(1): 59-69.

Baumgartner, A., C. K. Hitzenberger, et al. (2000). "Resolution-improved dual-beam and standard optical coherence tomography: a comparison." *Graefes Archive for Clinical and Experimental Ophthalmology* 238(5): 385-392.

Baumgartner, A., C. K. Hitzenberger, et al. (1998). "Signal and resolution enhancements in dual beam optical coherence tomography of the human eye." *Journal of Biomedical Optics* 3(1): 45-54.

Beaurepaire, E., P. Gleyzes, et at. (1998). *Optical coherence microscopy for the in-depth study of biological structures: System based on a parallel detection scheme*, Proceedings of SPIE—The International Society for Optical Engineering.

Beaurepaire, E., L. Moreaux, et al. (1999). "Combined scanning optical coherence and two-photon-excited fluorescence microscopy." *Optics Letters* 24(14): 969-971.

Bechara, F. G., T. Gambichler, et al. (2004). "Histomorphologic correlation with routine histology and optical coherence tomography." *Skin Research and Technology* 10 (3): 169-173.

Bechmann, M., M. J. Thiel, et al. (2000). "Central corneal thickness determined with optical coherence tomography in various types of glaucoma. [see comments]." *British Journal of Ophthalmology* 84(11): 1233-7.

Bek, T. and M. Kandi (2000). "Quantitative anomaloscopy and optical coherence tomography scanning in central serous chorioretinopathy." *Acta Ophthalmologica Scandinavica* 78(6): 632-7.

Benoit, A. M., K. Naoun, et al. (2001). "Linear dichroism of the retinal nerve layer expressed with Mueller matrices." *Applied Optics* 40(4): 565-569.

Bicout, D., C. Brosseau, et al. (1994). "Depolarization of Multiply Scattered Waves by Spherical Diffusers—Influence of the Size Parameter." *Physical Review* E 49(2): 1767-1770.

Blanchot, L., M. Lebec, et al. (1997). *Low-coherence in depth microscopy for biological tissues imaging: Design of a real time control system.* Proceedings of SPIE—The International Society for Optical Engineering.

Blumenthal, E. Z. and R. N. Weinreb (2001). "Assessment of the retinal nerve fiber layer in clinical trials of glaucoma neuroprotection. [Review] [36 refs]." *Survey of Ophthalmology* 45(Suppl 3): S305-12; discussion S332-4.

Blumenthal, E. Z., J. M. Williams, et al. "Reproducibility of nerve fiber layer thickness measurements by use of optical coherence tomography." *Ophthalmology* 107(12): 2278-82.

Boppart, S. A., B. E. Bouma, et al. (1996). "Imaging developing neural morphology using optical coherence tomography." *Journal of Neuroscience Methods* 70.

Boppart, S. A., B. E. Bouma, et al. (1997)."Forward-imaging instruments for optical coherence tomography." *Optics Letters* 22.

Boppart, S. A., B. E. Bouma, et al. (1998). "Intraoperative assessment of microsurgery with three-dimensional optical coherence tomography." *Radiology* 208: 81-86.

Boppart, S. A., J. Herrmann, et al. (1999). "High-resolution optical coherence tomography-guided laser ablation of surgical tissue." *Journal of Surgical Research* 82(2): 275-84.

Bouma, B. E. and J. G. Fujimoto (1996). "Compact Kerr-lens mode-locked resonators." *Optics Letters* 21. 134-136.

Bouma, B. E., L. E. Nelson, et al. (1998). "Optical coherence tomographic imaging of human tissue at 1.55 mu m and 1.81 mu m using Er and Tm-doped fiber sources." *Journal of Biomedical Optics* 3. 76-79.

Bouma, B. E., M. Ramaswamy-Paye, et al. (1997). "Compact resonator designs for mode-locked solid-state lasers." *Applied Physics B (Lasers and Optics)* B65. 213-220.

Bouma, B. E. and G. J. Tearney (2002)."Clinical imaging with optical coherence tomography." *Academic Radiology* 9(8): 942-953.

(56) References Cited

OTHER PUBLICATIONS

Bouma, B. E., G. J. Tearney, et al. (1996). "Self-phase-modulated Kerr-lens mode-locked Cr:forsterite laser source for optical coherence tomography." *Optics Letters* 21(22): 1839.
Bouma, B. E., G. J. Tearney, et al. (2000). "High-resolution imaging of the human esophagus and stomach in vivo using optical coherence tomography." *Gastrointestinal Endoscopy* 51(4): 467-474.
Bouma, B. E., G. J. Tearney, et al. (2003). "Evaluation of intracoronary stenting by intravascular optical coherence tomography." *Heart* 89(3): 317-320.
Bourquin, S., V. Monterosso, et al. (2000). "Video-rate optical low-coherence reflectometry based on a linear smart detector array." *Optics Letters* 25(2): 102-104.
Bourquin, S., P. Seitz, et al. (2001). "Optical coherence topography based on a two-dimensional smart detector array." *Optics Letters* 26(8): 512-514.
Bouzid, A., M. A. G. Abushagur, et al. (1995). "Fiber-optic four-detector polarimeter." *Optics Communications* 118(3-4):329-334.
Bowd, C., R. N. Weinreb, et al. (2000). "The retinal nerve fiber layer thickness in ocular hypertensive, normal, and glaucomatous eyes with optical coherence tomography." *Archives of Ophthalmology* 118(1): 22-6.
Bowd, C., L. M. Zangwill, et al. (2001). "Detecting early glaucoma by assessment of retinal nerve fiber thickness and visual function." *Investigative Ophthalmology & Visual Science* 42(9): 1993-2003.
Bowd, C., L. M. Zangwill, et al. (2002). "Imaging of the optic disc and retinal nerve fiber layer: the effects of age, optic disc area, refractive error, and gender." *Journal of the Optical Society of America, A, Optics, Image Science, & Vision* 19(1): 197-207.
Brand, S., J. M. Poneros, et al. (2000). "Optical coherence tomography in the gastrointestinal tract." *Endoscopy* 32(10): 796-803.
Brezinski, M. E. and J. G. Fujimoto (1999). "Optical coherence tomography: high-resolution imaging in nontransparent tissue." *IEEE Journal of Selected Topics in Quantum Electronics* 5(4): 1185-1192.
Brezinski, M. E., G. J. Tearney, et al. (1996). "Imaging of coronary artery microstructure (in vitro) with optical coherence tomography." *American Journal of Cardiology* 77 (1): 92-93.
Brezinski, M. E., G. J. Tearney, et al. (1996). "Optical coherence tomography for optical biopsy—Properties and demonstration of vascular pathology." *Circulation* 93(6): 1206-1213.
Brezinski, M. E., G. J. Tearney, et al. (1997). "Assessing atherosclerotic plaque morphology: Comparison of optical coherence tomography and high frequency intravascular ultrasound." *Heart* 77(5): 397-403.
Brink, H. B. K. and G. J. Vanblokland (1988). "Birefringence of the Human Foveal Area Assessed Invivo with Mueller-Matrix Ellipsometry." *Journal of the Optical Society of America a—Optics Image Science and Vision* 5(1): 49-57.
Brosseau, C. and D. Bicout (1994). "Entropy Production in Multiple-Scattering of Light by a Spatially Random Medium." *Physical Review E* 50(6): 4997-5005.
Burgoyne, C. F., D. E. Mercante, et al. (2002). "Change detection in regional and volumetric disc parameters using longitudinal confocal scanning laser tomography." *Ophthalmology* 109(3): 455-66.
Candido, R. and T. J. Allen (2002). "Haemodynamics in microvascular complications in type 1 diabetes." *Diabetes-Metabolism Research and Reviews* 18(4): 286-304.
Cense, B., T. C. Chen, et al. (2004). "Thickness and birefringence of healthy retinal nerve fiber layer tissue measured with polarization-sensitive optical coherence tomography." *Investigative Ophthalmology & Visual Science* 45(8): 2606-2612.
Cense, B., N. Nassif, et al. (2004). "Ultrahigh-Resolution High-Speed Retinal Imaging Using Spectral-Domain Optical Coherence Tomography." *Optics Express* 12(11): 2435-2447.
Chance, B., J. S. Leigh, et al. (1988). "Comparison of Time-Resolved and Time-Unresolved Measurements of Deoxyhemoglobin in Brain." *Proceedings of the National Academy of Sciences of the United States of America* 85(14): 4971-4975.

Chang, E. P., D. A. Keedy, et al. (1974). "Ultrastructures of Rabbit Corneal Stroma—Mapping of Optical and Morphological Anisotropies." *Biochimica Et Biophysica Acta* 343(3): 615-626.
Chartier, T., A. Hideur, et al. (2001). "Measurement of the elliptical birefringence of single-mode optical fibers." *Applied Optics* 40(30): 5343-5353.
Chauhan, B. C., J. W. Blanchard, et al. "Technique for Detecting Serial Topographic Changes in the Optic Disc and Peripapillary Retina Using Scanning Laser Topographic Tomograph." *Invest Ophthalmol Vis Sci* 41: 775-782.
Chen, Z. P., T. E. Milner, et al. (1997). "Optical Doppler tomographic imaging of fluid flow velocity in highly scattering media." *Optics Letters* 22(1): 64-66.
Chen, Z. P., T. E. Milner, et al. (1997). "Noninvasive imaging of in vivo blood flow velocity using optical Doppler tomography." *Optics Letters* 22(14): 1119-1121.
Chen, Z. P., Y. H. Zhao, et al. (1999). "Optical Doppler tomography." *Ieee Journal of Selected Topics in Quantum Electronics* 5(4): 1134-1142.
Cheong, W. F., S. A. Prahl, et al. (1990). "A Review of the Optical-Properties of Biological Tissues." *Ieee Journal of Quantum Electronics* 26(12): 2166-2185.
Chernikov, S. V., Y. Zhu, et al. (1997). "Supercontinuum self-Q-switched ytterbium fiber laser." *Optics Letters* 22(5): 298-300.
Cho, S. H., B. E. Bouma, et al. (1999). "Low-repetition-rate high-peak-power Kerr-lens mode-locked Ti:AI/sub 2/0/sub 3/ laser with a multiple-pass cavity." *Optics Letters* 24(6): 417-419.
Choma, M. A., M. V. Sarunic, et al. (2003). "Sensitivity advantage of swept source and Fourier domain optical coherence tomography." *Optics Express* 11(18): 2183-2189.
Choma, M. A., C. H. Yang, et al. (2003). "Instantaneous quadrature low-coherence with interferometry with 3 x 3 fiber-optic couplers." *Optics Letters* 28(22): 2162-2164.
Choplin, N. T. and D. C. Lundy (2001). "The sensitivity and specificity of scanning laser polarimetry in the detection of glaucoma in a clinical setting." *Ophthalmology* 108 (5): 899-904.
Christens Barry, W. A., W. J. Green, et al. (1996). "Spatial mapping of polarized light transmission in the central rabbit cornea." *Experimental Eye Research* 62(6): 651-662.
Chvapil, M., D. P. Speer, et al. (1984). "Identification of the depth of burn injury by collagen stainability." *Plastic & Reconstructive Surgery* 73(3): 438-41.
Cioffi, G. A. (2001). "Three common of assumptions about ocular blood flow and glaucoma." *Survey of Ophthalmology* 45: S325-S331.
Coleman, A. L. (1999). "Glaucoma." *Lancet* 354(9192): 1803-10.
Collaborative Normal-Tension Glaucoma Study Group (1998). "Comparison of Glaucomatous Progression Between Untreated Patients With Normal Tension Glaucoma and Patients with Therapeutically Reduced Intraocular Pressures." *Am J Ophthalmol* 126: 487-97.
Collaborative Normal-Tension Glaucoma Study Group (1998). "The effectiveness of intraocular pressure reduction in the treatment of normal-tension glaucoma." *Am J Ophthalmol* 126: 498-505.
Collaborative Normal-Tension Glaucoma Study Group (2001). "Natural History of Normal-Tension Glaucoma." *Ophthalmology* 108: 247-253.
Colston, B. W., M. J. Everett, et al. (1998). "Imaging of hard- and soft-tissue structure in the oral cavity by optical coherence tomography." *Applied Optics* 37(16): 3582-3585.
Colston, B. W., U. S. Sathyam, et al. (1998). "Dental OCT." *Optics Express* 3(6): 230-238.
Congdon, N. G., D. S. Friedman, et al. (2003). "Important causes of visual impairment in the world today." *Jama—Journal of the American Medical Association* 290(15): 2057-2060.
Cregan, R. F., B. J. Mangan, et al. (1999). "Single-mode photonic band gap guidance of light in air." *Science* 285(5433):1537-1539.
DalMolin, M., A. Galtarossa, et al. (1997). "Experimental investigation of linear polarization in high-birefringence single-mode fibers." *Applied Optics* 36(12): 2526-2528.
Danielson, B. L. and C. D. Whittenberg (1987). "Guided-Wave Reflectometry with Micrometer Resolution." *Applied Optics* 26(14): 2836-2842.

(56) References Cited

OTHER PUBLICATIONS

Dave, D. P. and T. E. Milner (2000). "Doppler-angle measurement in highly scattering media." *Optics Letters* 25(20): 1523-1525.

De Boer, J. F., T. E. Milner, et al. (1998). *Two dimensional birefringence imaging in biological tissue using phase and polarization sensitive optical coherence tomography.* Trends in Optics and Photonics (TOPS): Advances in Optical Imaging and Photon Migration, Orlando, USA, Optical Society of America, Washington, DC 1998.

De Boer, J. F., C. E. Saxer, et al. (2001). "Stable carrier generation and phase-resolved digital data processing in optical coherence tomography." *Applied Optics* 40(31): 5787-5790.

Degroot, P. and L. Deck (1993). "3-Dimensional Imaging by Sub-Nyquist Sampling of White-Light Interferograms." *Optics Letters* 18(17): 1462-1464.

Denk, W., J. H. Strickler, et al. (1990). "2-Photon Laser Scanning Fluorescence Microscopy." *Science* 248(4951): 73-76.

Descour, M. R., A. H. O. Karkkainen, et al. (2002). "Toward the development of miniaturized Imaging systems for detection of pre-cancer." *Ieee Journal of Quantum Electronics* 38(2): 122-130.

Dettwiller, L. (1997). "Polarization state interference: A general investigation." *Pure and Applied Optics* 6(1): 41-53.

DiCarlo, C. D., W. P. Roach, et al. (1999). "Comparison of optical coherence tomography imaging of cataracts with histopathology." *Journal of Biomedical Optics* 4.

Ding, Z., Y. Zhao, et al. (2002). "Real-time phase-resolved optical coherence tomography and optical Doppler tomography." *Optics Express* 10(5): 236-245.

Dobrin, P. B. (1996). "Effect of histologic preparation on the cross-sectional area of arterial rings." *Journal of Surgical Research* 61(2):413-5.

Donohue, D. J., B. J. Stoyanov, et al. (1995). "Numerical Modeling of the Corneas Lamellar Structure and Birefringence Properties." *Journal of the Optical Society of America a—Optics Image Science and Vision* 12(7): 1425-1438.

Doornbos, R. M. P., R. Lang, et al. (1999). "The determination of in vivo human tissue optical properties and absolute chromophore concentrations using spatially resolved steady-state diffuse reflectance spectroscopy." *Physics in Medicine and Biology* 44(4): 967-981.

Drexler, W., A. Baumgartner, et al. (1997). "Biometric investigation of changes in the anterior eye segment during accommodation." *Vision Research* 37(19): 2789-2800.

Drexler, W., A. Baumgartner, et al. (1997). "Submicrometer precision biometry of the anterior segment of the human eye." *Investigative Ophthalmology & Visual Science* 38(7): 1304-1313.

Drexler, W., A. Baumgartner, et al. (1998). "Dual beam optical coherence tomography: signal identification for ophthalmologic diagnosis." *Journal of Biomedical Optics* 3 (1): 55-65.

Drexler, W., O. Findl, et al. (1998). "Partial coherence interferometry: A novel approach to biometry in cataract surgery." *American Journal of Ophthalmology* 126(4): 524-534.

Drexler, W., O. Findl, et al. (1997). "Clinical feasibility of dual beam optical coherence topography and tomography for ophthalmologic diagnosis." *Investigative Ophthalmology & Visual Science* 38(4): 1038-1038.

Drexler, W., C. K. Hitzenberger, et al. "Investigation of dispersion effects in ocular media by multiple wavelength partial coherence interferometry." *Experimental Eye Research* 66(1): 25-33.

Drexler, W., C. K. Hitzenberger, et al. (1996). "(Sub)micrometer precision biometry of the human eye by optical coherence tomography and topography." *Investigative Ophthalmology & Visual Science* 37(3): 4374-4374.

Drexler, W., C. K. Hitzenberger, et aI. (1995). "Measurement of the Thickness of Fundus Layers by Partial Coherence Tomography." *Optical Engineering* 34(3): 701-710.

Drexler, W., U. Morgner, et al. (2001). "8 Ultrahigh-resolution ophthalmic optical coherence tomography." *Nature Medicine* 7(4): 502-507.

Drexler, W., U. Morgner, et al. (2001). "Ultrahigh-resolution ophthalmic optical coherence tomography. [erratum appears in Nat Med May 2001;7(5):636.]." *Nature Medicine* 7(4): 502-7.

Drexler, W., H. Sattmann, et al. (2003). "Enhanced visualization of macular pathology with the use of ultrahigh-resolution optical coherence tomography." *Archives of Ophthalmology* 121(5): 695-706.

Drexler, W., D. Stamper, et al. (2001). "Correlation of collagen organization with polarization sensitive imaging of in vitro cartilage: implications for osteoarthritis." *Journal of Rheumatology* 28(6): 1311-8.

Droog, E. J., W. Steenbergen, et al. (2001). "Measurement of depth of burns by laser Doppler perfusion imaging." *Burns* 27(6): 561-8.

Dubois, A., K. Grieve, et al. (2004). "Ultrahigh-resolution full-field optical coherence tomography." *Applied Optics* 43(14): 2874-2883.

Dubois, A., L. Vabre, et al. (2002). "High-resolution full-field optical coherence tomography with a Linnik microscope." *Applied Optics* 41(4): 805-812.

Ducros, M., M. Laubscher, et al. (2002). "Parallel optical coherence tomography in scattering samples using a two-dimensional smart-pixel detector array." *Optics Communications* 202(1-3): 29-35.

Ducros, M. G., J. D. Marsack, et al. (2001). "Primate retina imaging with polarization-sensitive optical coherence tomography." *Journal of the Optical Society of America a—Optics Image Science and Vision* 18(12): 2945-2956.

Duncan, A., J. H. Meek, et al. (1995). "Optical Pathlength Measurements on Adult Head, Calf and Forearm and the Head of the Newborn-Infant Using Phase-Resolved Optical Spectroscopy." *Physics in Medicine and Biology* 40(2): 295-304.

Eigensee, A., G. Haeusler, et al. (1996). "New method of short-coherence interferometry in human skin (in vivo) and in solid volume scatterers." *Proceedings of SPIE—The International Society for Optical Engineering* 2925: 169-178.

Eisenbeiss, W., J. Marotz, et al. (1999). "Reflection-optical multispectral imaging method for objective determination of burn depth." *Burns* 25(8): 697-704.

Elbaum, M., M. King, et al. (1972). "Wavelength-Diversity Technique for Reduction of Speckle Size." *Journal of the Optical Society of America* 62(5): 732-&.

Ervin, J. C., H. G. Lemij, et al. (2002). "Clinician change detection viewing longitudinal stereophotographs compared to confocal scanning laser tomography in the LSU Experimental Glaucoma (LEG) Study." *Ophthalmology* 109(3): 467-81.

Essenpreis, M., C. E. Elwell, et al. (1993). "Spectral Dependence of Temporal Point Spread Functions in Human Tissues." *Applied Optics* 32(4): 418-425.

Eun, H. C. (1995). "Evaluation of skin blood flow by laser Doppler flowmetry. [Review] [151 refs]." *Clinics in Dermatology* 13(4): 337-47.

Evans, J. A., J. M. Poneros, et al. (2004). "Application of a histopathologic scoring system to optical coherence tomography (OCT) images to identify high-grade dysplasia in Barrett's esophagus." *Gastroenterology* 126(4): A51-A51.

Feldchtein, F. I., G. V. Gelikonov, et al. "In vivo OCT imaging of hard and soft tissue of the oral cavity." *Optics Express* 3(6): 239-250.

Feldchtein, F. I., G. V. Gelikonov, et al. (1998). "Endoscopic applications of optical coherence tomography." *Optics Express* 3(6): 257-270.

Fercher, A. F., W. Drexler, et al. (1997). "Optical ocular tomography." *Neuro-Ophthalmology* 18(2): 39-49.

Fercher, A. F., W. Drexler, et al. (1994). *Measurement of optical distances by optical spectrum modulation.* Proceedings of SPIE—The International Society for Optical Engineering.

Fercher, A. F., W. Drexler, et al. (2003). "Optical coherence tomography—principles and applications." *Reports on Progress in Physics* 66(2): 239-303.

Fercher, A. F., C. Hitzenberger, et al. (1991). "Measurement of Intraocular Optical Distances Using Partially Coherent Laser-Light." *Journal of Modern Optics* 38(7): 1327-1333.

Fercher, A. F., C. K. Hitzenberger, et al. (1996). *Ocular partial coherence interferometry,* Proceedings of SPIE—The International Society for Optical Engineering.

(56) References Cited

OTHER PUBLICATIONS

Fercher, A. F., C. K. Hitzenberger, et al. (1993). "In-Vivo Optical Coherence Tomography." *American Journal of Ophthalmology* 116(1): 113-115.

Fercher, A. F., C. K. Hitzenberger, et al. (1994). *In-vivo dual-beam optical coherence tomography*. Proceedings of SPIE—The International Society for Optical Engineering.

Fercher, A. F., C. K. Hitzenberger, et al. (1995). "Measurement of Intraocular Diseases by Backscattering Spectral Interferometry." *Optics Communications* 117(1-2): 43-48.

Fercher, A. F., C. K. Hitzenberger, et al. (2000). "A thermal light source technique for optical coherence tomography." *Optics Communications* 185(1-3): 57-64.

Fercher, A. F., C. K. Hitzenberger, et al. (2001). "Numerical dispersion compensation for Partial Coherence Interferometry and Optical Coherence Tomography." *Optics Express* 9(12): 610-615.

Fercher, A. F., C. K. Hitzenberger, et al. (2002). "Dispersion compensation for optical coherence tomography depth-scan signals by a numerical technique." *Optics Communications* 204(1-6): 67-74.

Fercher, A. F., H. C. Li, et al. (1993). "Slit Lamp Laser-Doppler Interferometer." *Lasers in Surgery and Medicine* 13(4): 447-452.

Fercher, A. F., K. Mengedoht, et at. (1988). "Eye-Length Measurement by Interferometry with Partially Coherent-Light." *Optics Letters* 13(3): 186-188.

Ferro, P., M. Haelterman, et al. (1991). "All-Optical Polarization Switch with Long Low-Birefringence Fiber." *Electronics Letters* 27(16): 1407-1408.

Fetterman, M. R., D. Goswami, et al. (1998). "Ultrafast pulse shaping: amplification and characterization." *Optics Express* 3(10): 366-375.

Findl, O., W. Drexler, et al. (2001). "Improved prediction of intraocular lens power using partial coherence interferometry." *Journal of Cataract and Refractive Surgery* 27 (6): 861-867.

Fork, R. L., C. H. B. Cruz, et al. (1987). "Compression of Optical Pulses to 6 Femtoseconds by Using Cubic Phase Compensation." *Optics Letters* 12(7): 483-485.

Foschini, G. J. and C. D. Poole (1991). "Statistical-Theory of Polarization Dispersion in Single-Mode Fibers." *Journal of Lightwave Technology* 9(11): 1439-1456.

Francia, C., F. Bruyere, et al. (1998). "PMD second-order effects on pulse propagation in single-mode optical fibers." *Ieee Photonics Technology Letters* 10(12): 1739-1741.

Fried, D., R. E. Glena, et al. (1995). "Nature of Light-Scattering in Dental Enamel and Dentin at Visible and near-Infrared Wavelengths." *Applied Optics* 34(7): 1278-1285.

Fujimoto, J. G., M. E. Brezinski, et al. (1995). "Optical Biopsy and Imaging Using Optical Coherence Tomography." *Nature Medicine* 1(9): 970-972.

Fukasawa, A. and H. Iijima (2002). "Optical coherence tomography of choroidal osteoma." *American Journal of Ophthalmology* 133(3): 419-21.

Fymat, A. L. (1981). "High-Resolution Interferometric Spectrophotopolarimetry." *Optical Engineering* 20(1): 25-30.

Galtarossa, A., L. Palmieri, et al. (2000). "Statistical characterization of fiber random birefringence." *Optics Letters* 25(18): 1322-1324.

Galtarossa, A., L. Palmieri, et al. (2000). "Measurements of beat length and perturbation length in long single-mode fibers." *Optics Letters* 25(6): 384-386.

Gandjbakhche, A. H., P. Mills, et al. (1994). "Light-Scattering Technique for the Study of Orientation and Deformation of Red-Blood-Cells in a Concentrated Suspension." *Applied Optics* 33(6): 1070-1078.

Garcia, N. and M. Nieto-Vesperinas (2002). "Left-handed materials do not make a perfect lens." *Physical Review Letters* 88(20).

Gelikonov, V. M., G. V. Gelikonov, et al. (1995). "Coherent Optical Tomography of Microscopic Inhomogeneities in Biological Tissues." *Jetp Letters* 61(2): 158-162.

George, N. and A. Jain (1973). "Speckle Reduction Using Multiple Tones of Illumination." *Applied Optics* 12(6): 1202-1212.

Gibson, G. N., R. Klank, et al. (1996). "Electro-optically cavity-dumped ultrashort-pulse Ti:sapphire oscillator." *Optics Letters* 21(14): 1055.

Gil, J. J. (2000). "Characteristic properties of Mueller matrices." *Journal of the Optical Society of America a—Optical Image Science and Vision* 17(2): 328-334.

Gil, J. J. and E. Bernabeu (1987). "Obtainment of the Polarizing and Retardation Parameters of a Nondepolarizing Optical-System from the Polar Decomposition of Its Mueller Matrix." *Optik* 76(2): 67-71.

Gladkova, N. D., G. A. Petrova, et al. (2000). "In vivo optical coherence tomography imaging of human skin: norm and pathology." *Skin Research and Technology* 6 (1): 6-16.

Glaessl, A., A. G. Schreyer, et al. (2001). "Laser surgical planning with magnetic resonance imaging-based 3-dimensional reconstructions for intralesional Nd : YAG laser therapy of a venous malformation of the neck." *Archives of Dermatology* 137(10): 1331-1335.

Gloesmann, M., B. Hermann, et al. (2003). "Histologic correlation of pig retina radial stratification with ultrahigh-resolution optical coherence tomography." *Investigative Ophthalmology & Visual Science* 44(4): 1696-1703.

Goldberg, L. and D. Mehuys (1994). "High-Power Superluminescent Diode Source." *Electronics Letters* 30(20): 1682-1684.

Goldsmith, J. A., Y. Li, et al. (2005). "Anterior chamber width measurement by high speed optical coherence tomography." *Ophthalmology* 112(2): 238-244.

Goldstein, L. E., J. A. Muffat, et al. (2003). "Cytosolic beta-amyloid deposition and supranuclear cataracts in lenses from people with Alzheimer's disease." *Lancet* 361(9365): 1258-1265.

Golubovic, B., B. E. Bouma, et al. (1996). "Thin crystal, room-temperature Cr/sup +/:forsterite laser using near-infrared pumping." *Optics Letters* 21(24): 1993-1995.

Gonzalez, S. and Z. Tannous (2002). "Real-time, in vivo confocal reflectance microscopy of basal cell carcinoma." *Journal of the American Academy of Dermatology* 47(6): 869-874.

Gordon, M. O. and M. A. Kass (1999). "The Ocular Hypertension Treatment Study: design and baseline description of the participants." *Archives of Ophthalmology* 117(5): 573-83.

Grayson, T. P., J. R. Torgerson, et al. (1994). "Observation of a Nonlocal Pancharatnam Phase-Shift in the Process of Induced Coherence without Induced Emission." *Physical Review* A 49(1): 626-628.

Greaney, M. J., D. C. Hoffman, et al. (2002). "Comparison of optic nerve imaging methods to distinguish normal eyes from those with glaucoma." *Investigative Ophthalmology & Visual Science* 43(1): 140-5.

Greenfield, D. S., H. Bagga, et al. (2003). "Macular thickness changes in glaucomatous optic neuropathy detected using optical coherence tomography." *Archives of Ophthalmology* 121(1): 41-46.

Greenfield, D. S., R. W. Knighton, et al. "Effect of corneal polarization axis on assessment of retinal nerve fiber layer thickness by scanning laser polarimetry." *American Journal of Ophthalmology* 129(6): 715-722.

Griffin, R. A., D. D. Sampson, et al. (1995). "Coherence Coding for Photonic Code-Division Multiple-Access Networks." *Journal of Lightwave Technology* 13(9): 1826-1837.

Guedes, V., J. S. Schuman, et al. (2003). "Optical coherence tomography measurement of macular and nerve fiber layer thickness in normal and glaucomatous human eyes." *Ophthalmology* 110(1): 177-189.

Gueugniaud, P. Y., H. Carsin, et al. (2000). "Current advances in the initial management of major thermal burns. [Review] [76 refs]." *Intensive Care Medicine* 26(7): 848-56.

Guido, S. and R. T. Tranquillo (1993). "A Methodology for the Systematic and Quantitative Study of Cell Contact Guidance in Oriented Collagen Gels—Correlation of Fibroblast Orientation and Gel Birefringence." *Journal of Cell Science* 105: 317-331.

Gurses-Ozden, R., H. Ishikawa, et al. (1999). "Increasing sampling density improves reproducibility of optical coherence tomography measurements." *Journal of Glaucoma* 8(4): 238-41.

Guzzi, R. (1998). "Scattering Theory from Homogeneous and Coated Spheres." 1-11.

(56) References Cited

OTHER PUBLICATIONS

Haberland, U. B., Vladimir; Schmitt, Hans J (1996). "Optical coherent tomography of scattering media using electrically tunable near-infrared semiconductor laser." *Applied Optics* Draft.

Haberland, U. R., Walter; Blazek, Vladimir; Schmitt, Hans J. (1995). "Investigation of highly scattering media using near-infrared continuous wave tunable semiconductor laser." *Proc. SPIE*, 2389: 503-512.

Hale, G. M. and M. R. Querry (1973). "Optical-Constants of Water in 200-Nm to 200-Mum Wavelength Region." *Applied Optics* 12(3): 555-563.

Hammer, D. X., R. D. Ferguson, et al. (2002). "Image stabilization for scanning laser ophthalmoscopy." *Optics Express* 10(26): 1542.

Hara, T., Y. Ooi, et al. (1989). "Transfer Characteristics of the Microchannel Spatial Light-Modulator." *Applied Optics* 28(22): 4781-4786.

Harland, C. C., S. G. Kale, et al. (2000). "Differentiation of common benign pigmented skin lesions from melanoma by high-resolution ultrasound." *British Journal of Dermatology* 143(2): 281-289.

Hartl, I., X. D. Li, et al. (2001). "Ultrahigh-resolution optical coherence tomography using continuum generation in an air-silica microstructure optical fiber." *Optics Letters* 26(9): 608-610.

Hassenstein, A., A. A. Bialasiewicz, et al. (2000). "Optical coherence tomography in uveitis patients." *American Journal of Ophthalmology* 130(5): 669-70.

Hattenhauer, M. G., D. H. Johnson, et al. (1998). "The probability of blindness from open-angle glaucoma. [see comments]." *Ophthalmology* 105(11): 2099-104.

Hausler, G., J. M. Herrmann, et al. (1996). "Observation of light propagation in volume scatterers with 10(11)-fold slow motion." *Optics Letters* 21(14): 1087-1089.

Hazebroek, H. F. and A. A. Holscher (1973). "Interferometric Ellipsometry." *Journal of Physics E—Scientific Instruments* 6(9): 822-826.

Hazebroek, H. F. and W. M. Visser (1983). "Automated Laser Interferometric Ellipsometry and Precision Reflectometry." *Journal of Physics E—Scientific Instruments* 16(7): 654-661.

He, Z. Y., N. Mukohzaka, et al. (1997). "Selective image extraction by synthesis of the coherence function using two-dimensional optical lock-in amplifier with microchannel spatial light modulator." *Ieee Photonics Technology Letters* 9(4): 514-516.

Hee, M. R., J. A. Izatt, et al. (1993). "Femtosecond Transillumination Optical Coherence Tomography." *Optics Letters* 18(12): 950-952.

Hee, M. R., J. A. Izatt, et al. (1995). "Optical coherence tomography of the human retina." *Archives of Ophthalmology* 113(3): 325-32.

Hee, M. R., C. A. Puliafito, et al. (1998). "Topography of diabetic macular edema with optical coherence tomography." *Ophthalmology* 105(2): 360-70.

Hee, M. R., C. A. Puliafito, et al. (1995). "Quantitative assessment of macular edema with optical coherence tomography." *Archives of Ophthalmology* 113(8): 1019-29.

Hellmuth, T. and M. Welle (1998). "Simultaneous measurement of dispersion, specturm, and distance with a fourier transform spectrometer." *Journal of Biomedical Optics* 3(1): 7-11.

Hemenger, R. P. (1989). "Birefringence of a medium of tenuous parallel cylinders." *Applied Optics* 28(18): 4030-4034.

Henry, M. (1981). "Fresnel-Arago Laws for Interference in Polarized-Light—Demonstration Experiment." *American Journal of Physics* 49(7): 690-691.

Herz, P. R., Y. Chen, et al. (2004). "Micromotor endoscope catheter for in vivo, ultrahigh-resolution optical coherence tomography." *Optics Letters* 29(19): 2261-2263.

Hirakawa, H., H. Iijima, et al. (1999). "Optical coherence tomography of cystoid macular edema associated with retinitis pigmentosa." *American Journal of Ophthalmology* 128(2): 185-91.

Hitzenberger, C. K., A. Baumgartner, et al. (1994). "Interferometric Measurement of Corneal Thickness with Micrometer Precision." *American Journal of Ophthalmology* 118(4): 468-476.

Hitzenberger, C. K., A. Baumgartner, et al. (1999). "Dispersion effects in partial coherence interferometry: Implications for intraocular ranging." *Journal of Biomedical Optics* 4(1): 144-151.

Hitzenberger, C. K., A. Baumgartner, et al. (1998). "Dispersion induced multiple signal peak splitting in partial coherence interferometry." *Optics Communications* 154 (4): 179-185.

Hitzenberger, C. K., M. Danner, et al. (1999). "Measurement of the spatial coherence of superluminescent diodes." *Journal of Modern Optics* 46(12): 1763-1774.

Hitzenberger, C. K. and A. F. Fercher (1999). "Differential phase contrast in optical coherence tomography." *Optics Letters* 24(9): 622-624.

Hitzenberger, C. K., M. Sticker, et al. (2001). "Differential phase measurements in low-coherence interferometry without 2 pi ambiguity." *Optics Letters* 26(23): 1864-1866.

Hoeling, B. M., A. D. Fernandez, et al. (2000). "An optical coherence microscope for 3-dimensional imaging in developmental biology." *Optics Express* 6(7): 136-146.

Hoerauf, H., C. Scholz, et al. (2002). "Transscleral optical coherence tomography: a new imaging method for the anterior segment of the eye." *Archives of Ophthalmology* 120(6): 816-9.

Hoffmann, K., M. Happe, et al. (1998). "Optical coherence tomography (OCT) in dermatology." *Journal of Investigative Dermatology* 110(4): 583-583.

Hoh, S. T., D. S. Greenfield, et al. (2000). "Optical coherence tomography and scanning laser polarimetry in normal, ocular hypertensive, and glaucomatous eyes." *American Journal of Ophthalmology* 129(2): 129-35.

Hohenleutner, U., M. Hilbert, et al. (1995). "Epidermal Damage and Limited Coagulation Depth with the Flashlamp-Pumped Pulsed Dye-Laser—a Histochemical-Study." *Journal of Investigative Dermatology* 104(5): 798-802.

Holland, A. J. A., H. C. O. Martin, et al. (2002). "Laser Doppler imaging prediction of burn wound outcome in children." *Burns* 28(1): 11-17.

Hotate, K. and T. Okugawa (1994). "Optical Information-Processing by Synthesis of the Coherence Function." *Journal of Lightwave Technology* 12(7): 1247-1255.

Hourdakis, C. J. and A. Perris (1995). "A Monte-Carlo Estimation of Tissue Optical-Properties for Use in Laser Dosimetry." *Physics in Medicine and Biology* 40(3): 351-364.

Hu, Z., F. Li, et al. (2000). "Wavelength-tunable narrow-linewidth semiconductor fiber-ring laser." *IEEE Photonics Technology Letters* 12(8): 977-979.

Huang, F., W. Yang, et al. (2001). "Quadrature spectral interferometric detection and pulse shaping." *Optics Letters* 26(6): 382-384.

Huang, X. R. and R. W. Knighton (2002). "Linear birefringence of the retinal nerve fiber layer measured in vitro with a multispectral imaging micropolarimeter." *Journal of Biomedical Optics* 7(2): 199-204.

Huber, R., M. Wojtkowski, et al. (2005). "Amplified, frequency swept lasers for frequency domain reflectometry and OCT imaging: design and scaling principles." *Optics Express* 13(9): 3513-3528.

Hunter, D. G., J. C. Sandruck, et al. (1999). "Mathematical modeling of retinal birefringence scanning." *Journal of the Optical Society of America a—Optics Image Science and Vision* 16(9): 2103-2111.

Hurwitz, H. H. and R. C. Jones (1941). "A new calculus for the treatment of optical systems II. Proof of three general equivalence theorems." *Journal of the Optical Society of America* 31(7): 493-499.

Huttner, B., C. De Banos, et al. (1999). "Polarization-induced pulse spreading in birefringent optical fibers with zero differential group delay." *Optics Letters* 24(6): 370-372.

Huttner, B., B. Gisin, et al. (1999). "Distributed PMD measurement with a polarization-OTDR in optical fibers." *Journal of Lightwave Technology* 17(10): 1843-1848.

Huttner, B., J. Reecht, et al. (1998). "Local birefringence measurements in single-mode fibers with coherent optical frequency-domain reflectometry." *Ieee Photonics Technology Letters* 10(10): 1458-1460.

(56) References Cited

OTHER PUBLICATIONS

Hyde, S. C. W., N. P. Barry, et al. (1995). "Sub-100-Mu-M Depth-Resolved Holographic Imaging through Scattering Media in the near-Infrared." *Optics Letters* 20(22): 2330-2332.
Hyde, S. C. W., N. P. Barry, et al. (1995). "Depth-Resolved Holographic Imaging through Scattering Media by Photorefraction." *Optics Letters* 20(11): 1331-1333.
Iftimia, N. V., B. E. Bouma, et al. (2004). "Adaptive ranging for optical coherence tomography." *Optics Express* 12(17): 4025-4034.
Iida, T., N. Hagimura, et al. (2000). "Evaluation of central serous chorioretinopathy with optical coherence tomography." *American Journal of Ophthalmology* 129(1): 16-20.
Imai, M., H. Iijima, et al. (2001). "Optical coherence tomography of tractional macular elevations in eyes with proliferative diabetic retinopathy. [republished in Am J Ophthalmol. Sep. 2001;132(3):458-61 ; 11530091.]." *American Journal of Ophthalmology* 132(1): 81-4.
Indebetouw, G. and P. Klysubun (2000). "Imaging through scattering media with depth resolution by use of low-coherence gating in spatiotemporal digital holography." *Optics Letters* 25(4): 212-214.
Ip, M. S., B. J. Baker, et al. (2002). "Anatomical outcomes of surgery for idiopathic macular hole as determined by optical coherence tomography." *Archives of Ophthalmology* 120(1): 29-35.
Ismail, R., V. Tanner, et al. (2002). "Optical coherence tomography imaging of severe commotio retinae and associated macular hole." *British Journal of Ophthalmology* 86(4): 473-4.
Izatt, J. A., M. R. Hee, et al. (1994). "Optical Coherence Microscopy in Scattering Media." *Optics Letters* 19(8): 590-592.
Izatt, J. A., M. R. Hee, et al. (1994). "Micrometer-scale resolution imaging of the anterior eye in vivo with optical coherence tomography." *Archives of Ophthalmology* 112 (12): 1584-9.
Izatt, J. A., M. D. Kulkarni, et al. (1997). "In vivo bidirectional color Doppler flow imaging of picoliter blood volumes using optical coherence tomography." *Optics Letters* 22(18): 1439-1441.
Izatt, J. A., M. D. Kulkarni, et al. (1996). "Optical coherence tomography and microscopy in gastrointestinal tissues." *IEEE Journal of Selected Topics in Quantum Electronics* 2(4): 1017.
Jacques, S. L., J. S. Nelson, et al. (1993). "Pulsed Photothermal Radiometry of Port-Wine-Stain Lesions." *Applied Optics* 32(13): 2439-2446.
Jacques, S. L., J. R. Roman, et al. (2000). "Imaging superficial tissues with polarized light." *Lasers in Surgery and Medicine* 26(2): 119-129.
Jang, I. K., B. E. Bouma, et al. (2002). "Visualization of coronary atherosclerotic plaques in patients using optical coherence tomography: Comparison with intravascular ultrasound." *Journal of the American College of Cardiology* 39(4): 604-609.
Jong, I. K., B. D. MacNeill, et al. (2002). "In-vivo characterization of coronary plaques in patients with ST elevation acute myocardial infarction using optical coherence tomography (OCT)." *Circulation* 106(19): 698-698 3440 Supp. S,.
Jang, I. K., G. J. Tearney, et al. (2000). "Comparison of optical coherence tomography and intravascular ultrasound for detection of coronary plaques with large lipid-core in living patients." *Circulation* 102(18): 509-509.
Jeng, J. C., A. Bridgeman, et al. (2003). "Laser Doppler imaging determines need for excision and grafting in advance of clinical judgement: a prospective blinded trial." *Burns* 29(7): 665-670.
Jesser, C. A., S. A. Boppart, et al. (1999). "High resolution imaging of transitional cell carcinoma with optical coherence tomography: feasibility for the evaluation of bladder cell carcinoma pathology." *British Journal of Radiology* 72: 1170-1176.
Johnson, C. A., J. L. Keltner, et al. (2002). "Baseline visual field characteristics in the ocular hypertension treatment study." *Ophthalmology* 109(3): 432-7.
Jones, R. C. (1941). "A new calculus for the treatment of optical systems III. The Sohncke theory of optical activity." *Journal of the Optical Society of America* 31 (7): 500-503.

Jones, R. C. (1941). "A new calculus for the treatment of optical systems I. Description and discussion of the calculus." *Journal of the Optical Society of America* 31(7): 488-493.
Jones, R. C. (1942). "A new calculus for the treatment of optical systems. IV." *Journal of the Optical Society of America* 32(8): 486-493.
Jones, R. C. (1947). "A New Calculus for the Treatment of Optical Systems .6. Experimental Determination of the Matrix." *Journal of the Optical Society of America* 37(2): 110-112.
Jones, R. C. (1947). "A New Calculus for the Treatment of Optical Systems .5. A More General Formulation, and Description of Another Calculus." *Journal of the Optical Society of America* 37(2): 107-110.
Jones, R. C. (1948). "A New Calculus for the Treatment of Optical Systems .7. Properties of the N-Matrices." *Journal of the Optical Society of America* 38(8): 671-685.
Jones, R. C. (1956). "New Calculus for the Treatment of Optical Systems .8. Electromagnetic Theory." *Journal of the Optical Society of America* 46(2): 126-131.
Jopson, R. M., L. E. Nelson, et al. (1999). "Measurement of second-order polarization-mode dispersion vectors in optical fibers." *Ieee Photonics Technology Letters* 11 (9): 1153-1155.
Jost, B. M., A. V. Sergienko, et al. (1998). "Spatial correlations of spontaneously down-converted photon pairs detected with a single-photon-sensitive CCD camera." *Optics Express* 3(2): 81-88.
Kaplan, B., E. Compain, et al. (2000). "Phase-modulated Mueller ellipsometry characterization of scattering by latex sphere suspensions." *Applied Optics* 39 (4): 629-636.
Kass, M. A., D. K. Heuer, et al. (2002). "The Ocular Hypertension Treatment Study: a randomized trial determines that topical ocular hypotensive medication delays or prevents the onset of primary open-angle glaucoma." *Archives of Ophthalmology* 120(6): 701-13; discussion 829-30.
Kasuga, Y., J. Arai, et al. (2000). "Optical coherence tomoghraphy to confirm early closure of macular holes." *American Journal of Ophthalmology* 130(5): 675-6.
Kaufman, T., S. N. Lusthaus, et al. (1990). "Deep Partial Skin Thickness Burns—a Reproducible Animal-Model to Study Burn Wound-Healing." *Burns* 16(1): 13-16.
Kemp, N. J., J. Park, et al. (2005). "High-sensitivity determination of birefringence in turbid media with enhanced polarization-sensitive optical coherence tomography." *Journal of the Optical Society of America a—Optics Image Science and Vision* 22(3): 552-560.
Kerrigan-Baumrind, L. A., H. A. Quigley, et al. (2000). "Number of ganglion cells in glaucoma eyes compared with threshold visual field tests in the same persons." *Investigative Ophthalmology & Visual Science* 41(3): 741-8.
Kesen, M. R., G. L. Spaeth, et al. (2002). "The Heidelberg Retina Tomograph vs clinical impression in the diagnosis of glaucoma." *American Journal of Ophthalmology* 133(5): 613-6.
Kienle, A. and R. Hibst (1995). "A New Optimal Wavelength for Treatment of Port-Wine Stains." *Physics in Medicine and Biology* 40(10): 1559-1576.
Kienle, A., L. Lilge, et al. (1996). "Spatially resolved absolute diffuse reflectance measurements for noninvasive determination of the optical scattering and absorption coefficients of biological tissue." *Applied Optics* 35(13): 2304-2314.
Kim, B. Y. and S. S. Choi (1981). "Analysis and Measurement of Birefringence in Single-Mode Fibers Using the Backscattering Method." *Optics Letters* 6(11): 578-580.
Kimel, S., L. O. Svaasand, et al. (1994). "Differential Vascular-Response to Laser Photothermolysis." *Journal of Investigative Dermatology* 103(5): 693-700.
Kloppenberg, F. W. H., G. Beerthuizen, et al. (2001). "Perfusion of burn wounds assessed by Laser Doppler Imaging is related to burn depth and healing time." *Burns* 27(4): 359-363.
Knighton, R. W. and X. R. Huang (2002). "Analytical methods for scanning laser polarimetry." *Optics Express* 10(21): 1179-1189.
Knighton, R. W., X. R. Huang, et al. (2002). "Analytical model of scanning laser polarimetry for retinal nerve fiber layer assessment." *Investigative Ophthalmology & Visual Science* 43(2): 383-392.

(56) References Cited

OTHER PUBLICATIONS

Knuettel, A. R. S., Joseph M.; Shay, M.; Knutson, Jay R. (1994). "Stationary low-coherence light imaging and spectroscopy using a CCD camera." *Proc. SPIE*, vol. 2135: p. 239-250.

Knuttel, A. and M. Boehlau-Godau (2000). "Spatially confined and temporally resolved refractive index and scattering evaluation in human skin performed with optical coherence tomography." *Journal of Biomedical Optics* 5(1): 83-92.

Knuttel, A. and J. M. Schmitt (1993). "Stationary Depth-Profiling Reflectometer Based on Low-Coherence Interferometry." *Optics Communications* 102(3-4): 193-198.

Knuttel, A., J. M. Schmitt, et al. (1994). "Low-Coherence Reflectometry for Stationary Lateral and Depth Profiling with Acoustooptic Deflectors and a Ccd Camera." *Optics Letters* 19(4): 302-304.

Kobayashi, M., H. Hanafusa, et al. (1991). "Polarization-Independent Interferometric Optical-Time-Domain Reflectometer." *Journal of Lightwave Technology* 9(5): 623-628.

Kolios, M. C., M. D. Sherar, et al. (1995). "Large Blood-Vessel Cooling in Heating Tissues—a Numerical Study." *Physics in Medicine and Biology* 40(4): 477-494.

Koozekanani, D., K. Boyer, et al. (2001). "Retinal thickness measurements from optical coherence tomography using a Markov boundary model." *Ieee Transactions on Medical Imaging* 20(9): 900-916.

Kop, R. H. J. and R. Sprik (1995). "Phase-sensitive interferometry with ultrashort optical pulses." *Review of Scientific Instruments* 66(12): 5459-5463.

Kramer, R. Z., J. Bella, et al. (1999). "Sequence dependent conformational variations of collagen triple-helical structure." *Nature Structural Biology* 6(5): 454-7.

Kulkarni, M. D., T. G. van Leeuwen, et al. (1998). "Velocity-estimation accuracy and frame-rate limitations in color Doppler optical coherence tomography." *Optics Letters* 23(13): 1057-1059.

Kwon, Y. H., C. S. Kim, et al. (2001). "Rate of visual field loss and long-term visual outcome in primary open-angle glaucoma." *American Journal of Ophthalmology* 132(1): 47-56.

Kwong, K. F., D. Yankelevich, et al. (1993). "400-Hz Mechanical Scanning Optical Delay-Line." *Optics Letters* 18(7): 558-560.

Landers, J., I. Goldberg, et al. (2002). "Analysis of risk factors that may be associated with progression from ocular hypertension to primary open angle glaucoma." *Clin Experiment Ophthalmogy* 30(4): 242-7.

Laszlo, A. and A. Venetianer (1998). Heat resistance in mammalian cells: Lessons and challenges. *Stress of Life*. 851: 169-178.

Laszlo, A. and A. Venetianer (1998). "Heat resistance in mammalian cells: lessons and challenges. [Review] [52 refs]." *Annals of the New York Academy of Sciences* 851: 169-78.

Laufer, J., R. Simpson, et al. (1998). "Effect of temperature on the optical properties of ex vivo human dermis and subdermis." *Physics in Medicine and Biology* 43(9): 2479-2489.

Lederer, D. E., J. S. Schuman, et al. (2003). "Analysis of macular volume in normal and glaucomatous eyes using optical coherence tomography." *American Journal of Ophthalmology* 135(6): 838-843.

Lee, P. P., Z. W. Feldman, et al. (2003). "Longitudinal prevalence of major eye diseases." *Archives of Ophthalmology* 121(9): 1303-1310.

Lehrer, M. S., T. T. Sun, et al. (1998). "Strategies of epithelial repair: modulation of stem cell and transit amplifying cell proliferation." *Journal of Cell Science* 111(Pt 19): 2867-75.

Leibowitz, H. M., D. E. Krueger, et al. (1980). "The Framingham Eye Study monograph: An ophthalmological and epidemiological study of cataract, glaucoma, diabetic retinopathy, macular degeneration, and visual acuity in a general population of 2631 adults, 1973-1975." *Survey of Ophthalmology* 24(Suppl): 335-610.

Leitgeb, R., C. K. Hitzenberger, et al. (2003). "Performance of fourier domain vs. time domain optical coherence tomography." *Optics Express* 11(8): 889-894.

Leitgeb, R., L. F. Schmetterer, et al. (2002). "Flow velocity measurements by frequency domain short coherence interferometry." *Proc. SPIE* 4619: 16-21.

Leitgeb, R. A., W. Drexler, et al. (2004). "Ultrahigh resolution Fourier domain optical coherence tomography." *Optics Express* 12(10): 2156-2165.

Leitgeb, R. A., C. K. Hitzenberger, et al. (2003). "Phase-shifting algorithm to achieve high-speed long-depth-range probing by frequency-domain optical coherence tomography." *Optics Letters* 28(22): 2201-2203.

Leitgeb, R. A., L. Schmetterer, et al. (2003). "Real-time assessment of retinal blood flow with ultrafast acquisition by color Doppler Fourier domain optical coherence tomography." *Optics Express* 11(23): 3116-3121.

Leitgeb, R. A., L. Schmetterer, et al. (2004). "Real-time measurement of in vitro flow by Fourier-domain color Doppler optical coherencetomography." *Optics Letters* 29 (2): 171-173.

LeRoyBrehonnet, F. and B. LeJeune (1997). "Utilization of Mueller matrix formalism to obtain optical targets depolarization and polarization properties." *Progress in Quantum Electronics* 21(2): 109-151.

Leske, M. C., A. M. Connell, et al. (1995). "Risk factors for open-angle glaucoma. The Barbados Eye Study. [see comments]." *Archives of Ophthalmology* 113(7):918-24.

Leske, M. C., A. M. Connell, et al. (2001). "Incidence of open-angle glaucoma: the Barbados Eye Studies. The Barbados Eye Studies Group. [see comments]." *Archives of Ophthalmology* 119(1): 89-95.

Leske, M. C., A. Heijl, et al. (1999). "Early Manifest Glaucoma Trial. Design and Baseline Data." *Ophthalmology* 106(11): 2144-2153.

Lewis, S. E., J. R. DeBoer, et al. (2005). "Sensitive, selective, and analytical improvements to a porous silicon gas sensor." *Sensors and Actuators B: Chemical* 110(1): 54-65.

Lexer, F., C. K. Hitzenberger, et al. (1999). "Dynamic coherent focus OCT with depth-independent transversal resolution." *Journal of Modern Optics* 46(3): 541-553.

Li, X., C. Chudoba, et al. (2000). "Imaging needle for optical coherence tomography." *Optics Letters* 25: 1520-1522.

Li, X., T. H. Ko, et al. (2001). "Intraluminal fiber-optic Doppler imaging catheter for structural and functional optical coherence tomography." *Optics Letters* 26: 1906-1908.

Liddington, M. I. and P. G. Shakespeare (1996). "Timing of the thermographic assessment of burns." *Burns* 22(1): 26-8.

Lindmo, T., D. J. Smithies, et al. (1998). "Accuracy and noise in optical Doppler tomography studied by Monte Carlo simulation." *Physics in Medicine and Biology* 43(10): 3045-3064.

Liu, J., X. Chen, et al. (1999). "New thermal wave aspects on burn evaluation of skin subjected to instantaneous heating." *IEEE Transactions on Biomedical Engineering* 46(4): 420-8.

Luke, D. G., R. McBride, et al. (1995). "Polarization mode dispersion minimization in fiber-wound piezoelectric cylinders." *Optics Letters* 20(24): 2550-2552.

MacNeill, B. D., I. K. Jang, et al. (2004). "Focal and multi-focal plaque distributions in patients with macrophage acute and stable presentations of coronary artery disease." *Journal of the American College of Cardiology* 44(5): 972-979.

Mahgerefteh, D. and C. R. Menyuk (1999). "Effect of first-order PMD compensation on the statistics of pulse broadening in a fiber with randomly varying birefringence." *Ieee Photonics Technology Letters* 11(3): 340-342.

Maitland, D. J. and J. T. Walsh, Jr. (1997). "Quantitative measurements of linear birefringence during heating of native collagen." *Lasers in Surgery & Medicine* 20 (3): 310-8.

Majaron, B., S. M. Srinivas, et al. (2000). "Deep coagulation of dermal collagen with repetitive Er : YAG laser irradiation." *Lasers in Surgery and Medicine* 26(2): 215-222.

Mansuripur, M. (1991). "Effects of High-Numerical-Aperture Focusing on the State of Polarization in Optical and Magnetooptic Data-Storage Systems." *Applied Optics* 30(22): 3154-3162.

Marshall, G. W., S. J. Marshall, et al. (1997). "The dentin substrate: structure and properties related to bonding." *Journal of Dentistry* 25(6): 441-458.

(56) References Cited

OTHER PUBLICATIONS

Martin, P. (1997). "Wound healing—Aiming for perfect skin regeneration." *Science* 276 (5309): 75-81.

Martinez, O. E. (1987). "3000 Times Grating Compressor with Positive Group-Velocity Dispersion—Application to Fiber Compensation in 1.3-1.6 Mu-M Region." *Ieee Journal of Quantum Electronics* 23(1): 59-64.

Martinez, O. E., J. P. Gordon, et al. (1984). "Negative Group-Velocity Dispersion Using Refraction." *Journal of the Optical Society of America a—Optics Image Science and Vision* 1(10): 1003-1006.

McKinney, J. D., M. A. Webster, et al. (2000). "Characterization and imaging in optically scattering media by use of laser speckle and a variable-coherence source." *Optics Letters* 25(1): 4-6.

Miglior, S., M. Casula, et al. (2001). "Clinical ability of Heidelberg retinal tomograph examination to detect glaucomatous visual field changes." *Ophthalmology* 108 (9): 1621-7.

Milner, T. E., D. M. Goodman, et al. (1996). "Imaging laser heated subsurface chromophores in biological materials: Determination of lateral physical dimensions." *Physics in Medicine and Biology* 41(1): 31-44.

Milner, T. E., D. M. Goodman, et al. (1995). "Depth Profiling of Laser-Heated Chromophores in Biological Tissues by Pulsed Photothermal Radiometry." *Journal of the Optical Society of America a—Optics Image Science and Vision* 12 (7): 1479-1488.

Milner, T. E., D. J. Smithies, et al. (1996). "Depth determination of chromophores in human skin by pulsed photothermal radiometry." *Applied Optics* 35(19): 3379-3385.

Mishchenko, M. I. and J. W. Hovenier (1995). "Depolarization of Light Backscattered by Randomly Oriented Nonspherical Particles." (1995). *Optics Letters* 20(12): 1356-&.

Mistlberger, A., J. M. Liebmann, et al. (1999). "Heidelberg retina tomography and optical coherence tomography in normal, ocular-hypertensive, and glaucomatous eyes." *Ophthalmology* 106(10): 2027-32.

Mitsui, T. (1999). "High-speed detection of ballistic photons propagating through suspensions spectral interferometry." *Japanese Journal of Applied Physics Part 1—Regular Papers Short Notes & Review Papers* 38(5A): 2978-2982.

Molteno, A. C., N. J. Bosma, et al. (1999). "Otago glaucoma surgery outcome study: long-term results of trabeculectomy—1976 to 1995." *Ophthalmology* 106(9): 1742-50.

Morgner, U., W. Drexler, et al. (2000). "Spectroscopic optical coherence tomography." *Optics Letters* 25(2): 111-113.

Morgner, U., F. X. Kartner, et al. (1999). "Sub-two-cycle pulses from a Kerr-lens mode-locked Ti : sapphire laser (vol. 24, p. 411, 1999)." *Optics Letters* 24(13): 920-920.

Mourant, J. R., A. H. Hielscher, et al. (1998). "Evidence of intrinsic differences in the light scattering properties of tumorigenic and nontumorigenic cells." *Cancer Cytopathology* 84(6): 366-374.

Muller, M., J. Squier, et al. (1998). "Dispersion pre-compensation of 15 femtosecond optical pulses for high-numerical-aperture objectives." *Journal of Microscopy-Oxford* 191: 141-150.

Muscat, S., N. McKay, et al. (2002). "Repeatability and reproducibility of corneal thickness measurements by optical coherence tomography." *Investigative Ophthalmology & Visual Science* 43(6): 1791-5.

Musch, D. C., P. R. Lichter, et al. (1999). "The Collaborative Initial Glaucoma Treatment Study. Study Design, Methods, and Baseline Characteristics of Enrolled Patients." *Ophthalmology_* 106: 653-662.

Neerken, S., Lucassen, G.W., Bisschop, M.A., Lenderink, E., Nuijs, T.A.M. (2004). "Characterization of age-related effects in human skin: A comparative study that applies confocal laser scanning microscopy and optical coherence tomography." *Journal of Biomedical Optics* 9(2): 274-281.

Nelson, J. S., K. M. Kelly, et al. (2001). "Imaging blood flow in human port-wine stain in situ and in real time using optical Doppler tomography." *Archives of Dermatology* 137(6): 741-744.

Newson, T. P., F. Farahi, et al. (1988). "Combined Interferometric and Polarimetric Fiber Optic Temperature Sensor with a Short Coherence Length Source." *Optics Communications* 68(3): 161-165.

November, L. J. (1993). "Recovery of the Matrix Operators in the Similarity and Congruency Transformations—Applications in Polarimetry." *Journal of the Optical Society of America a—Optics Image Science and Vision* 10(4): 719-739.

Oh, W. Y., S. H. Yun, et al. (2005). "Wide tuning range wavelength-swept laser with two semiconductor optical amplifiers." *Ieee Photonics Technology Letters* 17(3): 678-680.

Oka, K. and T. Kato (1999). "Spectroscopic polarimetry with a channeled spectrum." *Optics Letters* 24(21): 1475-1477.

Okugawa, T. and K. Rotate (1996). "Real-time optical image processing by synthesis of the coherence function using real-time holography." *Ieee Photonics Technology Letters* 8(2): 257-259.

Oshima, M., R. Torii, et al. (2001). "Finite element simulation of blood flow in the cerebral artery." *Computer Methods in Applied Mechanics and Engineering* 191 (6-7): 661-671.

Pan, Y. T., H. K. Xie, et al. (2001). "Endoscopic optical coherence tomography based on a microelectromechanical mirror." *Optics Letters* 26(24): 1966-1968.

Parisi, V., G. Manni, et al. (2001). "Correlation between optical coherence tomography, pattern electroretinogram, and visual evoked potentials in open-angle glaucoma patients." *Ophthalmology* 108(5): 905-12.

Park, B. H., M. C. Pierce, et al. (2005). "Real-time fiber-based multi-functional spectral domain optical coherence tomography at 1.3 mu m." *Optics Express* 13(11): 3931-3944.

Park, D. H., J. W. Hwang, et al. (1998). "Use of laser Doppler flowmetry for estimation of the depth of burns." *Plastic and Reconstructive Surgery* 101(6): 1516-1523.

Pendry, J. B., A. J. Holden, et al. (1999). "Magnetism from conductors and enhanced nonlinear phenomena." *Ieee Transactions on Microwave Theory and Techniques* 47(11): 2075-2084.

Penninckx, D. and V. Morenas (1999). "Jones matrix of polarization mode dispersion." *Optics Letters* 24(13): 875-877.

Pierce, M. C., M. Shishkov, et al. (2005). "Effects of sample arm motion in endoscopic polarization-sensitive optical coherence tomography." *Optics Express* 13(15): 5739-5749.

Pircher, M., E. Gotzinger, et al. (2003). "Measurement and imaging of water concentration in human cornea with differential absorption optical coherence tomography." *Optics Express* 11(18): 2190-2197.

Pircher, M., E. Gotzinger, et al. (2003). "Speckle reduction in optical coherence tomography by frequency compounding." *Journal of Biomedical Optics* 8(3): 565-569.

Podoleanu, A. G., G. M. Dobre, et al. (1998). "En-face coherence imaging using galvanometer scanner modulation." *Optics Letters* 23(3): 147-149.

Podoleanu, A. G. and D. A. Jackson (1999). "Noise analysis of a combined optical coherence tomograph and a confocal scanning ophthalmoscope." *Applied Optics* 38(10): 2116-2127.

Podoleanu, A. G., J. A. Rogers, et al. (2000)."Three dimensional OCT images from retina and skin." *Optics Express* 7(9): 292-298.

Podoleanu, A. G., M. Seeger, et al. (1998). "Transversal and longitudinal images from the retina of the living eye using low coherence reflectometry." *Journal of Biomedical Optics* 3(1): 12-20.

Poole, C. D. (1988). "Statistical Treatment of Polarization Dispersion in Single-Mode Fiber." *Optics Letters* 13(8): 687-689.

Povazay, B., K. Bizheva, et al. (2002). "Submicrometer axial resolution optical coherence tomography." *Optics Letters* 27(20): 1800-1802.

Qi, B., A. P. Himmer, et al. (2004). "Dynamic focus control in high-speed optical coherence tomography based on a microelectromechanical mirror." *Optics Communications* 232(1-6): 123-128.

Radhakrishnan, S., A. M. Rollins, et al. (2001). "Real-time optical coherence tomography of the anterior segment at 1310 nm." *Archives of Ophthalmology* 119(8): 1179-1185.

Rogers, A. J. (1981). "Polarization-Optical Time Domain Reflectometry—a Technique for the Measurement of Field Distributions." *Applied Optics* 20(6): 1060-1074.

(56) References Cited

OTHER PUBLICATIONS

Rollins, A. M. and J. A. Izatt (1999). "Optimal interferometer designs for optical coherence tomography." *Optics Letters* 24(21): 1484-1486.
Rollins, A. M., R. Ung-arunyawee, et al. (1999). "Real-time in vivo imaging of human gastrointestinal ultrastructure by use of endoscopic optical coherence tomography with a novel efficient interferometer design." *Optics Letters* 24(19): 1358-1360.
Rollins, A. M., S. Yazdanfar, et al. (2002). "Real-time in vivo colors Doppler optical coherence tomography." *Journal of Biomedical Optics* 7(1): 123-129.
Rollins, A. M., S. Yazdanfar, et al. (2000). "Imaging of human retinal hemodynamics using color Doppler optical coherence tomography." *Investigative Ophthalmology & Visual Science* 41(4): S548-S548.
Sandoz, P. (1997). "Wavelet transform as a processing tool in white-light interferometry." *Optics Letters* 22(14): 1065-1067.
Sankaran, V., M. J. Everett, et al. (1999). "Comparison of polarized-light propagation in biological tissue and phantoms." *Optics Letters* 24(15): 1044-1046.
Sankaran, V., J. T. Walsh, et al. (2000). "Polarized light propagation through tissue phanto, ehms containing densely packed scatterers." *Optics Letters* 25(4): 239-241.
Sarunic, M. V., M. A. Choma, et al. (2005). "Instantaneous complex conjugate resolved spectral domain and swept-source OCT using 3x3 fiber couplers." *Optics Express* 13(3): 957-967.
Sathyam, U. S., B. W. Colston, et al. (1999). "Evaluation of optical coherence quantitation of analytes in turbit media by use of two wavelengths." *Applied Optics* 38(10): 2097-2104.
Schmitt, J. M. (1997). "Array detection for speckle reduction in optical coherence microscopy." *Physics in Medicine and Biology* 42(7): 1427-1439.
Schmitt, J. M. (1999). "Optical coherence tomography (OCT): A review." *Ieee Journal of Selected Topics in Quantum Electronics* 5(4): 1205-1215.
Schmitt, J. M. and A. Knuttel (1997). "Model of optical coherence tomography of heterogeneous tissue." *Journal of the Optical Society of America a—Optics Image Science and Vision* 14(6): 1231-1242.
Schmitt, J. M., S. L. Lee, et al. (1997). "An optical coherence microscope with enhanced resolving power in thick tissue." *Optics Communications* 142(4-6): 203-207.
Schmitt, J. M., S. H. Xiang, et al. (1998). "Differential absorption imaging with optical coherence tomography." *Journal of the Optical Society of America a—Optics Image Science and Vision* 15(9): 2288-2296.
Schmitt, J. M., S. H. Xiang, et al. (1999). "Speckle in optical coherence tomography." *Journal of Biomedical Optics* 4(1): 95-105.
Schmitt, J. M., M. J. Yadlowsky, et al. (1995). "Subsurface Imaging of Living Skin with Optical Coherence Microscopy." *Dermatology* 191(2): 93-98.
Shi, H., J. Finlay, et al. (1997). "Multiwavelength 10-GHz picosecond pulse generation from a single-stripe semiconductor diode laser." *Ieee Photonics Technology Letters* 9(11): 1439-1441.
Shi, H., I. Nitta, et al. (1999). "Demonstration of phase correlation in multiwavelength mode-locked semiconductor diode lasers." *Optics Letters* 24(4): 238-240.
Simon, R. (1982). "The Connection between Mueller and Jones Matrices of Polarization Optics." *Optics Communications* 42(5): 293-297.
Smith, P. J. M., E.M.; Taylor, C.M.; Selviah, D.R.; Day, S.E.; Commander, L.G. "Variable-Focus Microlenses as a Potential Technology for Endoscopy."
Smithies, D. J., T. Lindmo, et al. (1998). "Signal attenuation and localization in optical coherence tomography studied by Monte Carlo simulation." *Physics in Medicine and Biology* 43(10): 3025-3044.
Sorin, W. V. and D. F. Gray (1992). "Simultaneous Thickness and Group Index Measurement Using Optical Low-Coherence Reflectometry." *Ieee Photonics Technology Letters* 4(1): 105-107.

Sticker, M., C. K. Hitzenberger, et al. (2001). "Quantitative differential phase measurement and imaging in transparent and turbid media by optical coherence tomography." *Optics Letters* 26(8): 518-520.
Sticker, M., M. Pircher, et al. (2002). "En face imaging of single cell layers by differntial phase-contrast optical coherence microscopy." *Optics Letters* 27(13): 1126-1128.
Stoller, P., B. M. Kim, et al. (2002). "Polarization-dependent optical second-harmonic imaging of a rat-tail tendon." *Journal of Biomedical Optics* 7(2): 205-214.
Sun, C. S. (2003). "Multiplexing of fiber-optic acoustic sensors in a Michelson interferometer configuration." *Optics Letters* 28(12): 1001-1003.
Swanson, E. A., J. A. Izatt, et al. (1993). "In-Vivo Retinal Imaging by Optical Coherence Tomography." *Optics Letters* 18(21): 1864-1866.
Takada, K., A. Himeno, et al. (1991). "Phase-Noise and Shot-Noise Limited Operations of Low Coherence Optical-Time Domain Reflectometry." *Applied Physics Letters* 59(20): 2483-2485.
Takenaka, H. (1973). "Unified Formalism for Polarization Optics by Using Group-Theory I (Theory)." *Japanese Journal of Applied Physics* 12(2): 226-231.
Tanno, N., T. Ichimura, et al. (1994). "Optical Multimode Frequency-Domain Reflectometer." *Optics Letters* 19(8): 587-589.
Targowski, P., M. Wojtkowski, et al. (2004). "Complex spectral OCT in human eye imaging in vivo." *Optics Communications* 229(1-6): 79-84.
Tearney, G. J., S. A. Boppart, et al. (1996). "Scanning single-mode fiber optic catheter-endoscope for optical coherence tomography (vol. 21, p. 543, 1996)." *Optics Letters* 21(12): 912-912.
Tearney, G. J., B. E. Bouma, et al. (1996). "Rapid acquisition of in vivo biological images by use of optical coherence tomography." *Optics Letters* 21(17): 1408-1410.
Tearney, G. J., B. E. Bouma, et al. (1997). "In vivo endoscopic optical biopsy with optical coherence tomography." *Science* 276(5321): 2037-2039.
Tearney, G. J., M. E. Brezinski, et al. (1996). "Catheter-based optical imaging of a human coronary artery." *Circulation* 94(11): 3013-3013.
Tearney, G. J., M. E. Brezinski, et al. (1997). "In vivo endoscopic optical biopsy with optical coherence tomography." *Science* 276(5321): 2037-9.
Tearney, G. J., M. E. Brezinski, et al. (1997). "Optical biopsy in human gastrointestinal tissue using optical coherence tomography." *American Journal of Gastroenterology* 92(10): 1800-1804.
Tearney, G. J., M. E. Brezinski, et al. (1995). "Determination of the refractive index of highly scattering human tissue by optical coherence tomography." *Optics Letters* 20(21): 2258-2260.
Tearney, G. J., I. K. Jang, et al, (2000). "Porcine coronary imaging in vivo by optical coherence tomography." *Acta Cardiologica* 55(4): 233-237.
Tearney, G. J., R. H. Webb, et al. (1998). "Spectrally encoded confocal microscopy." *Optics Letters* 23(15): 1152-1154.
Tearney, G. J., H. Yabushita, et al. (2003). "Quantification of macrophage content in atherosclerotic plaques by optical coherence tomography." *Circulation* 107(1): 113-119.
Tower, T. T. and R. T. Tranquillo (2001). "Alignment maps of tissues: I. Microscopic elliptical polarimetry." *Biophysical Journal* 81(5): 2954-2963.
Tower, T. T. and R. T. Tranquillo (2001). "Alignment maps of tissues: II. Fast harmonic analysis for imaging." *Biophysical Journal* 81(5): 2964-2971.
Troy, T. L. and S. N. Thennadil (2001). "Optical properties of human skin in the near infrared wavelength range of 1000 to 2200 nm." *Journal of Biomedical Optics* 6 (2): 167-176.
Vabre, L., A. Dubois, et al. (2002). "Thermal-light full-field optical coherence tomography." *Optics Letters* 27(7): 530-532.
Vakhtin, A. B., D. J. Kane, et al. (2003). "Common-path interferometer for frequency-domain optical coherence tomography." *Applied Optics* 42(34): 6953-6958.
Vakhtin, A. B., K. A. Peterson, et al. (2003). "Differential spectral interferometry: an imaging technique for biomedical applications." *Optics Letters* 28(15): 1332-1334.

(56) References Cited

OTHER PUBLICATIONS

Vakoc, B. J., S. H. Yun, et al. (2005). "Phase-resolved optical frequency domain imaging." *Optics Express* 13(14): 5483-5493.
Van Leeuwen, T. G., M. D. Kulkarni, et al. (1999). "High-flow-velocity and shear-rate imaging by use of color Doppler optical coherence tomography." *Optics Letters* 24(22): 1584-1586.
Vansteenkiste, N., P. Vignolo, et al. (1993). "Optical Reversibility Theorems for Polarization—Application to Remote-Control of Polarization." *Journal of the Optical Society of America a—Optics Image Science and Vision* 10(10): 2240-2245.
Vargas, O., E. K. Chan, et al. (1999). "Use of an agent to reduce scattering in skin." *Lasers in Surgery and Medicine* 24(2): 133-141.
Wang, R. K. (1999). "Resolution improved optical coherence-gated tomography for imaging through biological tissues." *Journal of Modern Optics* 46(13): 1905-1912.
Wang, X. J., T. E. Milner, et al. (1997). "Measurement of fluid-flow-velocity profile in turbid media by the use of optical Doppler tomography." *Applied Optics* 36(1): 144-149.
Wang, X. J., T. E. Milner, et al. (1995). "Characterization of Fluid-Flow Velocity by Optical Doppler Tomography." *Optics Letters* 20(11): 1337-1339.
Wang, Y. M., J. S. Nelson, et al. (2003). "Optimal wavelength for ultrahigh-resolution optical coherence tomography." *Optics Express* 11(12): 1411-1417.
Wang, Y. M., Y. H. Zhao, et al. (2003). "Ultrahigh-resolution optical coherence tomography by broadband continuum generation from a photonic crystal fiber." *Optics Letters* 28(3): 182-184.
Watkins, L. R., S. M. Tan, et al. (1999). "Determination of interferometer phase distributions by use of wavelets." *Optics Letters* 24(13): 905-907.
Wetzel, J. (2001). "Optical coherence tomography in dermatology: a review." *Skin Research and Technology* 7(1): 1-9.
Wentworth, R. H. (1989). "Theoretical Noise Performance of Coherence-Multiplexed Interferometric Sensors." *Journal of Lightwave Technology* 7(6): 941-956.
Westphal, V., A. M. Rollins, et al. (2002). "Correction of geometric and refractive image distortions in optical coherence tomography applying Fermat's principle." *Optics Express* 10(9): 397-404.
Westphal, V., S. Yazdanfar, et al. (2002). "Real-time, high velocity-resolution color Doppler optical coherence tomography." *Optics Letters* 27(1): 34-36.
Williams, P. A. (1999). "Rotating-wave-plate Stokes polarimeter for differential group delay measurements of polarization-mode dispersion." *Applied Optics* 38(31): 6508-6515.
Wojtkowski, M., T. Bajraszewski, et al. (2003). "Real-time in vivo imaging by high-speed spectral optical coherence tomography." *Optics Letters* 28(19): 1745-1747.
Wojtkowski, M., A. Kowalczyk, et al. "Full range complex spectral optical coherence tomography technique in eye imaging." *Optics Letters* 27(16): 1415-1417.
Wojtkowski, M., R. Leitgeb, et al. (2002). "In vivo human retinal imaging by Fourier domain optical coherence tomography." *Journal of Biomedical Optics* 7(3): 457-463.
Wojtkowski, M., R. Leitgeb, et al. (2002). "Fourier domain OCT imaging of the human eye in vivo." *Proc. SPIE* 4619: 230-236.
Wojtkowski, M., V. J. Srinivasan, et al. (2004). "Ultrahigh-resolution, high-speed, Fourier domain optical coherence tomography and methods for dispersion compensation." *Optics Express* 12(11): 2404-2422.
Wong, B. J. F., Y. H. Zhao, et al. (2004). "Imaging the internal structure of the rat cochlea using optical coherence tomography at 0.827 mu m and 1.3 mu m." *Otolaryngology—Head and Neck Surgery* 130(3): 334-338.
Yabushita, H. B., B.E.; Houser, S.L.; Aretz, H.T.; Jang, I.; Schlendorf, K.H.; Kauffman, C.R.; Shishkov, M.; Halpern, E.F.; Tearney, G.J. "Measurement of Thin Fibrous Caps in Atherosclerotic Plaques by Optical Coherence Tomography."
Yang, C., A. Wax, et al. (2001). "Phase-dispersion optical tomography." *Optics Letters* 26(10): 686-688.

Yang, C., A. Wax, et al. (2001). "Phase-referenced interferometer with subwavelength and subhertz sensitivity applied to the study of cell membrane dynamics." *Optics Letters* 26(16): 1271-1273.
Yang, C. H., A. Wax, et al. (2001). "Phase-dispersion optical tomography." *Optics Letters* 26(10): 686-688.
Yang, C. H., A. Wax, et al. (2000). "Interferometric phase-dispersion microscopy." *Optics Letters* 25(20): 1526-1528.
Yang, V. X. D., M. L. Gordon, et al. (2002). "Improved phase-resolved optical Doppler tomography using the Kasai velocity estimator and histogram segmentation." *Optics Communications* 208(4-6): 209-214.
Yang, V. X. D., M. L. Gordon, et al. (2003). "High speed, wide velocity dynamic range Doppler optical coherence tomography (Part I): System design, signal processing, and performance." *Optics Express* 11(7): 794-809.
Yang, V. X. D., M. L. Gordon, et al. (2003). "High speed, wide velocity dynamic range Doppler optical coherence tomography (Part II): Imaging in vivo cardiac dynamics of Xenopus laevis." *Optics Express* 11(14): 1650-1658.
Yang, V. X. D., M. L. Gordon, et al. (2003). "High speed, wide velocity dynamic range Doppler optical coherence tomography (Part III): in vivo endoscopic imaging of blood flow in the rat and human gastrointestinal tracts." *Optics Express* 11(19): 2416-2424.
Yang, V. X. D., B. Qi, et al. (2003). "In vivo feasibility of endoscopic catheter-based Doppler optical coherence tomography." *Gastroenterology* 124(4): A49-A50.
Yao, G. and L. H. V. Wang (2000). "Theoretical and experimental studies of ultrasound-modulated optical tomography in biological tissue." *Applied Optics* 39(4): 659-664.
Yazdanfar, S. and J. A. Izatt (2002). "Self-referenced Doppler optical coherence tomography." *Optics Letters* 27(23): 2085-2087.
Yazdanfar, S., M. D. Kulkarni, et al. (1997). "High resolution imaging of in vivo cardiac dynamics using color Doppler optical coherence tomography." *Optics Express* 1 (13): 424-431.
Yazdanfar, S., A. M. Rollins, et al. (2000). "Imaging and velocimetry of the human retinal circulation with color Doppler optical coherence tomography." *Optics Letters* 25(19): 1448-1450.
Yazdanfar, S., A. M. Rollins, et al. (2000). "Noninvasive imaging and velocimetry of human retinal blood flow using color Doppler optical coherence tomography." *Investigative Ophthalmology & Visual Science* 41(4): S548-S548.
Yazdanfar, S., A. M. Rollins, et al. (2003). "In vivo imaging of human retinal flow dynamics by color Doppler optical coherence tomography." *Archives of Ophthalmology* 121(2): 235-239.
Yazdanfar, S., C. H. Yang, et al. (2005). "Frequency estimation precision in Doppler optical coherence tomography using the Cramer-Rao lower bound." *Optics Express* 13(2): 410-416.
Yun, S. H., C. Boudoux, et al. (2004). "Extended-cavity semiconductor wavelength-swept laser for biomedical imaging." *Ieee Photonics Technology Letters* 16(1): 293-295.
Yun, S. H., C. Boudoux, et al. (2003). "High-speed wavelength-swept semiconductor laser with a polygon-scanner-based wavelength filter." *Optics Letters* 28(20): 1981-1983.
Yun, S. H., G. J. Tearney, et al. (2004). "Pulsed-source and swept-source spectral-domain optical coherence tomography with reduced motion artifacts." *Optics Express* 12(23): 5614-5624.
Yun, S. H., G. J. Tearney, et al. (2004). "Removing the depth-degeneracy in optical frequency domain imaging with frequency shifting." *Optics Express* 12(20): 4822-4828.
Yun, S. H., G. J. Tearney, et al. (2004). "Motion artifacts in optical coherence tomography with frequency-domain ranging." *Optics Express* 12(13): 2977-2998.
Zhang, J., J. S. Nelson, et al. (2005). "Removal of a mirror image and enhancement of the signal-to-noise ratio in Fourier-domain optical coherence tomography using an electro-optic phase modulator." *Optics Letters* 30(2): 147-149.
Zhang, Y., M. Sato, et al. (2001). "Numerical investigations of optimal synthesis of several low coherence sources for resolution improvement." *Optics Communications* 192(3-6): 183-192.
Zhang, Y., M. Sato, et al. (2001). "Resolution improvement in optical coherence tomography by optimal synthesis of light-emitting diodes." *Optics Letters* 26(4): 205-207.

(56) References Cited

OTHER PUBLICATIONS

Zhao, Y., Z. Chen, et al. (2002). "Real-time phase-resolved functional optical coherence tomography by use of optical Hilbert transformation." *Optics Letters* 27(2): 98-100.
Zhao, Y. H., Z. P. Chen, et al. (2000). "Doppler standard deviation imaging for clinical monitoring of in vivo human skin blood flow." *Optics Letters* 25(18): 1358-1360.
Zhao, Y. H., Z. P. Chen, et al. (2000). "Phase-resolved optical coherence tomography and optical Doppler tomography for imaging blood flow in human skin with fast scanning speed and high velocity sensitivity." *Optics Letters* 25(2): 114-116.
Zhou, D., P. R. Prucnal, et al. (1998). "A widely tunable narrow linewidth semiconductor fiber ring laser." *IEEE Photonics Technology Letters* 10(6): 781-783.
Zuluaga, A. F. and R. Richards-Kortum (1999). "Spatially resolved spectral interferometry for determination of subsurface structure." *Optics Letters* 24(8): 519-521.
Zvyagin, A. V., J. B. FitzGerald, et al. (2000). "Real-time detection technique for Doppler optical coherence tomography." *Optics Letters* 25(22): 1645-1647.
Marc Nikles et al., "Brillouin gain spectrum characterization in single-mode optical fibers", *Journal of Lightwave Technology* 1997, 15 (10): 1842-1851.
Tsuyoshi Sonehara et al., "Forced Brillouin Spectroscopy Using Frequency-Tunable Continuous-Wave Lasers", *Physical Review Letters* 1995, 75 (23): 4234-4237.
Hajime Tanaka et al., "New Method of Superheterodyne Light Beating Spectroscopy for Brillouin-Scattering Using Frequency-Tunable Lasers", *Physical Review Letters* 1995, 74 (9): 1609-1612.
Webb RH et al. "Confocal Scanning Laser Ophthalmoscope", *Applied Optics* 1987, 26 (8): 1492-1499.
Andreas Zumbusch et al. "Three-dimensional vibrational imaging by coherent anti-Stokes Raman scattering", *Physical Review Letters* 1999, 82 (20): 4142-4145.
Katrin Kneipp et al., "Single molecule detection using surface-enhanced Raman scattering (SERS)", *Physical Review Letters* 1997, 78 (9): 1667-1670.
K.J. Koski et al., "Brillouin imaging" *Applied Physics Letters* 87, 2005.
Boas et al., "Diffusing temporal light correlation for burn diagnosis", *SPIE*, 1999, 2979:468-477.
David J. Briers, "Speckle fluctuations and biomedical optics: implications and applications", *Optical Engineering*, 1993, 32(2):277-283.Clark et al., "Tracking Speckle Patterns with Optical Correlation", *SPIE*, 1992, 1772:77-87.
Clark et al., "Tracking Speckle Patterns with Optical Correlation", *SPIE*, 1992, 1772:77-87.
Facchini et al., "An endoscopic system for DSPI", *Optik*, 1993, 95(1):27-30.
Hrabovsky, M., "Theory of speckle dispacement and decorrelation: application in mechanics", *SPIE*, 1998, 3479:345-354.
Sean J. Kirkpatrick et al., "Micromechanical behavior of cortical bone as inferred from laser speckle data", *Journal of Biomedical Materials Research*, 1998, 39(3):373-379.
Sean J. Kirkpatrick et al., "Laser speckle microstrain measurements in vascular tissue", *SPIE*, 1999, 3598:121-129.
Loree et al., "Mechanical Properties of Model Atherosclerotic Lesion Lipid Pools", *Arteriosclerosis and Thrombosis*, 1994, 14(2):230-234.
Podbielska, H. "Interferometric Methods and Biomedical Research", *SPIE*, 1999, 2732:134-141.
Richards-Kortum et al., "Spectral diagnosis of atherosclerosis using an optical fiber laser catheter", *American Heart Journal*, 1989, 118(2):381-391.
Ruth, B. "blood flow determination by the laser speckle method", *Int J Microcirc: Clin Exp*, 1990, 9:21-45.
Shapo et al., "Intravascular strain imaging: Experiments on an Inhomogeneous Phantom", *IEEE Ultrasonics Symposium* 1996, 2:1177-1180.
Shapo et al., "Ultrasonic displacement and strain imaging of coronary arteries with a catheter array", *IEEE Ultrasonics Symposium* 1995, 2:1511-1514.
Thompson et al., "Imaging in scattering media by use of laser speckle", *Opt. Soc. Am. A.*, 1997, 14(9):2269-2277.
Thompson et al., "Diffusive media characterization with laser speckle", *Applied Optics*, 1997, 36(16):3726-3734.
Tuchin, Valery V., "Coherent Optical Techniques for the Analysis of Tissue Structure and Dynamics," *Journal of Biomedical Optics*, 1999, 4(1):106-124.
M. Wussling et al., "Laser diffraction and speckling studies in skeletal and heart muscle", *Biomed, Biochim, Acta*, 1986, 45(1/2):S 23-S 27.
T. Yoshimura et al., "Statistical properties of dynamic speckles", *J. Opt. Soc. Am* . 1986, 3(7):1032-1054.
Zimnyakov et al., "Spatial speckle correlometry in applications to tissue structure monitoring", *Applied Optics* 1997, 36(22): 5594-5607.
Zimnyakov et al., "A study of statistical properties of partially developed speckle fields as applied to the diagnosis of structural changes in human skin", *Optics and Spectroscopy*, 1994, 76(5): 747-753.
Zimnyakov et al., "Speckle patterns polarization analysis as an approach to turbid tissue structure monitoring", *SPIE* 1999, 2981:172-180.
Ramasamy Manoharan et al., "Biochemical analysis and mapping of atherosclerotic human artery using FT-IR microspectroscopy", *Atherosclerosis*, May 1993, 181-1930.
N.V. Salunke et al., "Biomechanics of Atherosclerotic Plaque" *Critical Reviews™ in Biomedical Engineering* 1997, 25(3):243-285.
D. Fu et al., "Non-invasive quantitative reconstruction of tissue elasticity using an iterative forward approach", Phys. Med. Biol. 2000 (45): 1495-1509.
S.B. Adams Jr. et al., "The use of polarization sensitive optical coherence tomography and elastography to assess connective tissue", Optical Soc. of American Washington 2002, p. 3.
International Search Report for International Patent application No. PCT/US2005/039740.
International Written Opinion for International Patent application No. PCT/US2005/039740.
International Search Report for International Patent application No. PCT/US2005/030294.
International Written Opinion for International Patent application No. PCT/US2005/043951.
International Search Report for International Patent application No. PCT/US2005/043951.
Erdelyi et al. "Generation of diffraction-free beams for applications in optical microlithography", J. Vac. Sci. Technol. B 15 (12), Mar./Apr. 1997, pp. 287-292.
International Search Report for International Patent application No. PCT/US2005/023664.
International Written Opinion for International Patent application No. PCT/US2005/023664.
Tearney et al., "Spectrally encoded miniature endoscopy" Optical Society of America; Optical Letters vol. 27, No. 6, Mar. 15, 2002; pp. 412-414.
Yelin et al., "Double-clad Fiber for Endoscopy" Optical Society of America; Optical Letters vol. 29, No. 20, Oct. 16, 2005; pp. 2408-2410.
International Search Report for International Patent application No. PCT/US2001/049704.
International Search Report for International Patent application No. PCT/US2004/039454.
International Written Opinion for International Patent application No. PCT/US2004/039454.
PCT International Preliminary Report on Patentability for International Application No. PCT/US2004/038404 dated Jun. 2, 2006.
Notice of Reasons for Rejection and English translation for Japanese Patent Application No. 2002538830.

(56) References Cited

OTHER PUBLICATIONS

Office Action dated Aug. 24, 2006 for U.S. Appl. No. 10/137,749.
Barry Cense et al., "Spectral-domain polarization-sensitive optical coherence tomography at 850nm", Coherence Domain Optical Methods and Optical Coherence Tomography in Biomedicine IX, 2005, pp. 159-162.
A. Ymeti et al., "Integration of microfluidics with a four-channel integrated optical Young interferometer immunosensor", Biosensors and Bioelectronics, Elsevier Science Publishers, 2005, pp. 1417-1421.
PCT International Search Report for Application No. PCT/US2006/018865 filed May 5, 2006.
International Written Opinion for International Patent application No. PCT/US2006/018865 filed May 5, 2006.
John M. Poneros, "Diagnosis of Barrett's esophagus using optical coherence tomography", Gastrointestinal Endoscopy clinics of North America, 14 (2004) pp. 573-588.
P.F. Escobar et al., "Diagnostic efficacy of optical coherence tomography in the management of preinvasive and invasive cancer of uterine cervix and vulva", Int. Journal of Gynecological Cancer 2004, 14, pp. 470-474.
Ko T et al., "Ultrahigh resolution in vivo versus ex vivo OCT imaging and tissue preservation", Conference on Lasers and electro-optics, 2001, pp. 252-253.
Paul M. Ripley et al., "A comparison of Artificial Intelligence techniques for spectral classification in the diagnosis of human pathologies based upon optical biopsy", Journal of Optical Society of America, 2000, pp. 217-219.
Wolfgang Drexler et al., "Ultrahigh-resolution optical coherence tomography", Journal of Biomedical Optics Spie USA, 2004, pp. 47-74.
PCT International Search Report for Application No. PCT/US2006/016677 filed Apr. 28, 2006.
International Written Opinion for International Patent application No. PCT/US2006/016677 filed Apr. 28, 2006.
Office Action dated Nov. 13, 2006 for U.S. Appl. No. 10/501,268.
Office Action dated Nov. 20, 2006 for U.S. Appl. No. 09/709,162.
PCT International Search Report and Written Opinion for Application No. PCT/US2004/023585 filed Jul. 23, 2004.
Office Action dated Dec. 6, 2006 for U.S. Appl. No. 10/997,789.
Elliott, K. H. "The use of commercial CCD cameras as linear detectors in the physics undergraduate teaching laboratory", European Journal of Physics 19, 1998, pp. 107-117.
Lauer, V. "New approach to optical diffraction tomography yielding a vector equation of diffraction tomography and a novel tomographic microscope", Journal of Microscopy vol. 205, Issue 2, 2002, pp. 165-176.
Yu, P. et al. "Imaging of tumor necroses using full-frame optical coherence imaging", Proceedings of SPIE vol. 4956, 2003, pp. 34-41.
Zhao, Y. et al. "Three-dimensional reconstruction of in vivo blood vessels in human skin using phase-resolved optical Doppler tomography", IEEE Journal of Selected Topics in Quantum Electronics 7.6 (2001): 931-935.
Office Action dated Dec. 18, 2006 for U.S. Appl. No. 10/501,276.
Devesa, Susan S. et al. (1998) "Changing Patterns in the Incidence of Esophegeal and Gastric Carcinoma in the United States." *American Cancer Society* vol. 83, No. 10 pp. 2049-2053.
Barr, H et al. (2005) "Endoscopic Therapy for Barrett's Oesophaugs" *Gut* vol. 54:875-884.
Johnston, Mark H.(2005) "Technology Insight: Ablative Techniques for Barrett's Esophagus—Current and Emerging Trends" www.Nature.com/clinicalpractice/gasthep.
Falk, Gary W. et al. (1997) "Surveillance of Patients with Barrett's Esophagus for Dysplasia and Cancer with Ballon Cytology" *Gastrorenterology* vol. 112, pp. 1787-1797.
Sepchler, Stuart Jon. (1997) "Barrett's Esophagus: Should We Brush off this Balloning Problem?" *Gastroenterology* vol. 112, pp. 2138-2152.

Froehly, J. et al. (2003) "Multiplexed 3D Imaging Using Wavelength Encoded Spectral Interferometry: A Proof of Principle" *Optics Communications* vol. 222, pp. 127-136.
Kubba A.K. et al. (1999) "Role of p53 Assessment in Management of Barrett's Esophagus" *Digestive Disease and Sciences* vol. 44, No. 4. pp. 659-667.
Reid, Brian J. (2001) "p53 and Neoplastic Progression in Barrett's Esophagus" *The American Journal of Gastroenterology* vol. 96, No. 5, pp. 1321-1323.
Sharma, P. et al.(2003) "Magnification Chromoendoscopy for the Detection of Intestinal Metaplasia and Dysplasia in Barrett's Oesophagus" *Gut* vol. 52, pp. 24-27.
Kuipers E.J et al. (2005) "Diagnostic and Therapeutic Endoscopy" *Journal of Surgical Oncology* vol. 92, pp. 203-209.
Georgakoudi, Irene et al. (2001) "Fluorescence, Reflectance, and Light-Scattering Spectroscopy Evaluating Dysplasia in Patients with Barrett's Esophagus" *Gastroenterology* vol. 120, pp. 1620-1629.
Adrain, Alyn L. et al. (1997) "High-Resolution Endoluminal Sonography is a Sensitive Modality for the Identification of Barrett's Meaplasia" *Gastrointestinal Endoscopy* vol. 46, No. 2, pp. 147-151.
Canto, Marcia Irene et al (1999) "Vital Staining and Barrett's Esophagus" *Gastrointestinal Endoscopy* vol. 49, No. 3, part 2, pp. 12-16.
Evans, John A. et al. (2006) "Optical Coherence Tomography to Identify Intramucosal Carcinoma and High-Grade Dysplasia in Barrett's Esophagus" *Clinical Gastroenterology and Hepatology* vol. 4, pp. 38-3.
Poneros, John M. et al. (2001) "Diagnosis of Specialized Intestinal Metaplasia by Optical Coherence Tomography" *Gastroenterology* vol. 120, pp. 7-12.
Ho, W. Y. et al. (2005) "115 KHz Tuning Repetition Rate Ultrahigh-Speed Wavelength-Swept Semiconductor Laser" *Optics Letters* col. 30, No. 23, pp. 3159-3161.
Brown, Stanley B. et al. (2004) "The Present and Future Role of Photodynamic Therapy in Cancer Treatment" *The Lancet Oncology* vol. 5, pp. 497-508.
Boogert, Jolanda Van Den et al. (1999) "Endoscopic Ablation Therapy for Barrett's Esophagua with High-Grade Dysplasia: A Review" *The American Journal of Gastroenterology* vol. 94, No. 5, pp. 1153-1160.
Sampliner, Richard E. et al. (1996) "Reversal of Barrett's Esophagus with Acid Suppression and Multipolar Electrocoagulation: Preliminary Results" *Gastrointestinal Endoscopy* vol. 44, No. 5, pp. 532-535.
Sampliner, Richard E. (2004) "Endoscopic Ablative Therapy for Barrett's Esophagus: Current Status" *Gastrointestinal Endoscopy* vol. 59, No. 1, pp. 66-69.
Soetikno, Roy M. et al. (2003) "Endoscopic Mucosal resection" *Gastrointestinal Endoscopy* vol. 57, No. 4, pp. 567-579.
Ganz, Robert A. et al. (2004) "Complete Ablation of Esophageal Epithelium with a Balloon-based Bipolar Electrode: A Phased Evaluation in the Porcine and in the Human Esophagus" *Gastrointestinal Endoscopy* vol. 60, No. 6, pp. 1002-1010.
Pfefer, Jorje at al. (2006) "Performance of the Aer-O-Scope, A Pneumatic, Self Propelling, Self Navigating Colonoscope in Animal Experiments" *Gastrointestinal Endoscopy* vol. 63, No. 5, pp. AB223.
Overholt, Bergein F. et al. (1999) "Photodynamic Therapy for Barrett's Esophagus: Follow-Up in 100 Patients" *Gastrointestinal Endoscopy* vol. 49, No. 1, pp. 1-7.
Vogel, Alfred et al. (2003) "Mechanisms of Pulsed Laser Ablation of Biological Tissues" *American Chemical Society* vol. 103, pp. 577-644.
McKenzie, A. L. (1990) "Physics of Thermal Processes in Laser-Tissue Interaction" *Phys. Med. Biol* vol. 35, No. 9, pp. 1175-1209.
Anderson, R. Rox et al. (1983) "Selective Photothermolysis" Precise Microsurgery by Selective Absorption of Pulsed Radiation *Science* vol. 220, No. 4596, pp. 524-527.
Jacques, Steven L. (1993) "Role of Tissue Optics and Pulse Duration on Tissue Effects During High-Power Laser Irradiation" *Applied Optics* vol. 32, No. 13, pp. 2447-2454.

(56) References Cited

OTHER PUBLICATIONS

Nahen, Kester et al. (1999) "Investigations on Acosustic On-Line Monitoring of IR Laser Ablation of burned Skin" *Lasers in Surgery and Medicine* vol. 25, pp. 69-78.
Jerath, Maya R. et al. (1993) "Calibrated Real-Time Control of Lesion Size Based on Reflectance Images" *Applied Optics* vol. 32, No. 7, pp. 1200-1209.
Jerath, Maya R. et al (1992) "Dynamic Optical Property Changes: Implications for Reflectance Feedback Control of Photocoagulation" *Journal of Photochemical,.Photobiology. B: Biol* vol. 16, pp. 113-126.
Deckelbaum, Lawrence I. (1994) "Coronary Laser Angioplasty" *Lasers in Surgery and Medicine* vol. 14, pp. 101-110.
Kim, B.M. et al. (1998) "Optical Feedback Signal for Ultrashort Laser Pulse Ablation of Tissue" *Applied Surface Science* vol. 127-129, pp. 857-862.
Brinkman, Ralf et al. (1996) "Analysis of Cavitation Dynamics During Pulsed Laser Tissue Ablation by Optical On-Line Monitoring" *IEEE Journal of Selected Topics in Quantum Electronics* vol. 2, No. 4, pp. 826-835.
Whelan, W.M. et al. (2005) "A novel Strategy for Monitoring Laser Thermal Therapy Based on Changes in Optothermal Properties of Heated Tissues" *International Journal of Thermophysics* vol. 26., No. 1, pp. 233-241.
Thomsen, Sharon et al. (1990) "Microscopic Correlates of Macroscopic Optical Property Changes During Thermal Coagulation of Myocardium" *SPIE* vol. 1202, pp. 2-11.
Khan, Misban Huzaira et al. (2005) "Intradermally Focused Infrared Laser Pulses: Thermal Effects at Defined Tissue Depths" *Lasers in Surgery and Medicine* vol. 36, pp. 270-280.
Neumann, R.A. et al. (1991) "Enzyme Histochemical Analysis of Cell Viability After Argon Laser-Induced Coagulation Necrosis of the Skin" *Journal of the American Academy of Dermatology* vol. 25, No. 6, pp. 991-998.
Nadkarni, Seemantini K. et al (2005) "Charaterization of Atherosclerotic Plaques by Laser Speckle Imaging" *Circulation* vol. 112, pp. 885-892.
Zimnyakov, Dmitry A. et al (2002) "Speckle-Contrast Monitoring of Tissue Thermal Modification" *Applied Optics* vol. 41, No. 28, pp. 5989-5996.
Morelli, J.G., et al (1986) "Tunable Dye Laser (577 nm) Treatment of Port Wine Stains" *Lasers in Surgery and Medicine* vol. 6, pp. 94-99.
French, P.M.W. et al. (1993) "Continuous-wave Mode-Locked $Cr^{4+}$: YAG Laser" *Optics Letters* vol. 18, No. 1, pp. 39-41.
Sennaroglu, Alphan at al. (1995) "Efficient Continuous-Wave Chromium-Doped YAG Laser" *Journal of Optical Society of America* vol. 12, No. 5, pp. 930-937.
Bouma, B et al. (1994) "Hybrid Mode Locking of a Flash-Lamp-Pumped Ti: $Al_2O_3$ Laser" *Optics Letters* vol. 19, No. 22, pp. 1858-1860.
Bouma, B et al. (1995) "High Resolution Optical Coherence Tomography Using a Mode-Locked Ti: $Al_2O_3$ Laser Source" *Optics Letters* vol. 20, No. 13, pp. 1486-1488.
Fernández, Cabrera Delia et al. "Automated detection of retinal layer structures on optical coherence tomography images", *Optics Express* vol. 13, No. 25, Oct. 4, 2005, pp. 10200-10216.
Ishikawa, Hiroshi et al. "Macular Segmentation with optical coherence tomography", Investigative Ophthalmology & Visual Science, vol. 46, No. 6, Jun. 2005, pp. 2012-2017.
Nadkarni, Seemantini K., et al., "Measurement of fibrous cap thickness in atherosclerotic plaques by spatiotemporal analysis of laser speckle images", Journal of Biomedical Optics, vol. 11 Mar./Apr. 2006, pp. 021006-1-8.
Office Action dated Jul. 7, 2010 for U.S. Appl. No. 11/624,277.
Montag Ethan D., "Parts of the Eye" online textbook for JIMG 774: Vision & Psycophysics, download on Jun. 23, 2010 from http://www.cis.rit.edu/people/faculty/montag/vandplite/pages/chap_8/ch8p3.html.
Office Action dated Jul. 16, 2010 for U.S. Appl. No. 11/445,990.
Office Action dated Jul. 20, 2010 for U.S. Appl. No. 11/625,135.
Office Action dated Aug. 5, 2010 for U.S. Appl. No. 11/623,852.
Chinese office action dated Aug. 4, 2010 for CN 200780005949.9.
Chinese office action dated Aug. 4, 2010 for CN 200780016266.3.
Zhang et al., "Full Range Polarization-Sensitive Fourier Domain Optical Coherence Tomography" *Optics Express*, Nov. 29, 2004, vol. 12, No. 24.
Office Action dated Aug. 27, 2010 for U.S. Appl. No. 11/569,790.
Office Action dated Aug. 31, 2010 for U.S. Appl. No. 11/677,278.
Office Action dated Sep. 3, 2010 for U.S. Appl. No. 12/139,314.
Yong Zhao et al: "Virtual Data Grid Middleware Services for Data-Intensive Science", Concurrency and Computation: Practice and Experience, Wiley, London, GB, Jan. 1, 2000, pp. 1-7, pp. 1532-0626.
Swan et al., "Toward Nanometer-Scale Resolution in Fluorescence Microscopy using Spectral Self-Inteference" IEEE Journal. Selected Topics in Quantum Electronics 9 (2) 2003, pp. 294-300.
Moiseev et al., "Spectral Self-Interference Fluorescence Microscopy", J. Appl. Phys. 96 (9) 2004, pp. 5311-5315.
Hendrik Verschueren, "Interference Reflection Microscopy in Cell Biology", J. Cell Sci. 75, 1985, pp. 289-301.
Park et al., "Diffraction Phase and Fluorescence Microscopy", Opt. Expr. 14 (18) 2006, pp. 8263-8268.
Swan et al, "High Resolution Spectral Self-Interference Fluorescence Microscopy", Proc. SPIE 4621, 2002, pp. 77-85.
Sanchez et al., "Near-Field Fluorscence Microscopy Based on Two-Photon Excvitation with Metal Tips", Phys. Rev. Lett. 82 (20) 1999, pp. 4014-4017.
Wojtkowski, Maciej, Ph.D. "Three-Dimensional Retinal Imaging with High-Speed Ultrahigh-Resolution Optical Coherence Tomography" Ophthalmology, Oct. 2005, 112(10): 1734-1746.
Vaughan, J.M. et al., "Brillouin Scattering, Density and Elastic Properties of the Lens and Cornea of the Eye", Nature, vol. 284, Apr. 3, 1980, pp. 489-491.
Hess, S.T. et al. "Ultra-high Resolution Imaging by Fluorescence Photoactivation Localization Microscopy" Biophysical Journal vol. 91, Dec. 2006,4258-4272.
Fernandez-Suarez, M. et al., "Fluorescent Probes for Super-Resolution Imaging in Living Cells" Nature Reviews Molecular Cell Biology vol. 9, Dec. 2008.
Extended European Search Report dated Dec. 14, 2010 for EP 10182301.1.
S. Hell et al., "Breaking the diffraction resolution limit by stimulated-emission—stimulated-emission-depletion fluorescence microscopy," Optics Letters. 19:495 (1995) and Ground State Depletion (GSD).
S. Hell et al. "Ground-State-Depletion fluorescence microscopy—a concept for breaking the diffraction resolution limit," Applied Physics B. 60:780 (1994)) fluorescence microscopy, photoactivated localization microscopy (PALM).
E. Betzig et al. "Imaging intracellular fluorescent proteins at nanometer resolution," Science 313:1642 (2006), stochastic optical reconstruction microscopy (STORM).
M. Rust et al. "Sub-diffraction-limited imaging by stochastic optical reconstruction microscopy (STORM)," Nature Methods 3:783 (2006), and structured illumination microscopy (SIM).
Bailey et al. "Enhancement of Axial Resolution in Fluorescence Microscopy by Standing-Wave Excitation," Nature 366:44 (1993).
M. Gustafsson "Surpassing the lateral resolution limit by a factor of two using structured illumination microscopy," Journal of Microscopy 198:82 (2000).
M. Gustafsson "Nonlinear structured illumination microscopy: Widefield fluorescence imaging with theoretically unlimited resolution," PNAS 102:13081 (2005)).
R. Thompson et al. "Precise nanometer localization analysis for individual fluorescent probes," Biophysical Journal 82:2775 (2002).
K. Drabe et al. "Localization of Spontaneous Emission in front of a mirror," Optics Communications 73:91 (1989).
Swan et al. "Toward nanometer-scale resolution in fluorescence microscopy using spectral self-interference," IEEE Quantum Electronics 9:294 (2003).
C. Joo, et al. "Spectral Domain optical coherence phase and multiphoton microscopy," Optics Letters 32:623 (2007).

(56) References Cited

OTHER PUBLICATIONS

Virmani et al., "Lesions from sudden coronary death: A comprehensive morphological classification scheme for atherosclerotic lesions," Arterioscler. Thromb. Vase. Bio., 20:1262-75 (2000).
Gonzalez, R.C. and Wintz, P., "Digital Image Processing" Addison-Wesley Publishing Company, Reading MA, 1987.
V. Tuchin et al., "Speckle interferometry in the measurements ofbiotissues vibrations," SPIE, 1647: 125 (1992).
A.A. Bednov et al., "Investigation of Statistical Properties of Lymph Flow Dynamics Using Speckle-Microscopy," SPIE, 2981: 181-90 (1997).
Feng et al., "Mesocopic Conductors and Correlations in Laser Speckle Patters" Science, New Series, vol. 251, No. 4994, pp. 633-639 (Feb. 8, 1991).
Lee et al., "The Unstable Atheroma," Arteriosclerosis, Thrombosis & Vascular Biology, 17:1859-67 (1997).
International Search report dated Apr. 29, 2011 for PCT/US2010/051715.
International Search report dated Sep. 13, 2010 for PCT/US2010/023215.
International Search Report dated Jul. 28, 2011 for PCT/US2010/059534.
International Search report dated Nov. 18, 2011 for PCT/US2011/027450.
International Search report dated Nov. 18, 2011 for PCT/US2011/027437.
International Search report dated Nov. 22, 2011 for PCT/US2011/027421.
Office Action dated Oct. 11, 2007 for U.S. Appl. No. 11/534,095.
Office Action dated Oct. 9, 2007 for U.S. Appl. No. 09/709,162.
Notice of Allowance dated Oct. 3, 2007 for U.S. Appl. No. 11/225,840.
Siavash Yazdanfar et al., "In Vivo imaging in blood flow in human retinal vessels using color Doppler optical coherence tomography", SPIE, 1999 vol. 3598, pp. 177-184.
Office Action dated Oct. 30, 2007 for U.S. Appl. No. 11/670,069.
Tang C. L. et al., "Wide-band electro-optical tuning of semiconductor lasers", Applied Physics Letters, vol. 30, No. 2, Jan. 15, 1977, pp. 113-116.
Tang C. L. et al., "Transient effects in wavelength-modulated dye lasers", Applied Physics Letters, vol. 26, No. 9, May 1, 1975, pp. 534-537.
Telle M. John, et al., "Very rapid tuning of cw dye laser", Applied Physics Letters, vol. 26, No. 10, May 15, 1975, pp. 572-574.
Telle M. John, et al., "New method for electro-optical tuning of tunable lasers", Applied Physics Letters, vol. 24, No. 2, Jan. 15, 1974, pp. 85-87.
Schmitt M. Joseph et al. "OCT elastography: imaging microscopic deformation and strain of tissue", Optics Express, vol. 3, No. 6, Sep. 14, 1998, pp. 199-211.
M. Gualini Muddassir et al., "Recent Advancements of Optical Interferometry Applied to Medicine", IEEE Transactions on Medical Imaging, vol. 23, No. 2, Feb. 2004, pp. 205-212.
Maurice L. Roch et al. "Noninvasive Vascular Elastography: Theoretical Framework", IEEE Transactions on Medical Imaging, vol. 23, No. 2, Feb. 2004, pp. 164-180.
Kirkpatrick J. Sean et al. "Optical Assessment of Tissue Mechanical Properties", Proceedings of the SPIE—The International Society for Optical Engineering SPIE—vol. 4001, 2000, pp. 92-101.
Lisauskas B. Jennifer et al., "Investigation of Plaque Biomechanics from Intravascular Ultrasound Images using Finite Element Modeling", Proceedings of the 19$^{th}$ International Conference—IEEE Oct. 30-Nov. 2, 1997. pp. 887-888.
Parker K. J. et al., "Techniques for Elastic Imaging: A Review", IEEE Engineering in Medicine and Biology, Nov./Dec. 1996, pp. 52-59.
European Patent Office Search Report for Application No. 05791226.3.
Dubois Arnaud et al., "Ultrahigh-resolution OCT using white-light interference microscopy", Proceedings of SPIE, 2003, vol. 4956, pp. 14-21.

Office Action dated Jan. 3, 2008 for U.S. Appl. No. 10/997,789.
Office Action dated Dec. 21, 2007 for U.S. Appl. No. 11/264,655.
Office Action dated Dec. 18, 2007 for U.S. Appl. No. 11/288,994.
Office Action dated Jan. 10, 2008 for U.S. Appl. No. 11/435,228.
Office Action dated Jan. 10, 2008 for U.S. Appl. No. 11/410,937.
Office Action dated Jan. 11, 2008 for U.S. Appl. No. 11/445,990.
Office Action dated Feb. 4, 2008 for U.S. Appl. No. 10/861,179.
PCT International Search Report and Written Opinion for Application No. PCT/US2007/061463 dated Jan. 23, 2008.
PCT International Search Report and Written Opinion for Application No. PCT/US2007/061481 dated Mar. 17, 2008.
PCT International Search Report and Written Opinion for Application No. PCT/US2007/078254 dated Mar. 28, 2008.
Sadhwani, Ajay et al., "Determination of Teflon thickness with laser speckle I. Potential for burn depth diagnosis", Optical Society of America, 1996, vol. 35, No. 28, pp. 5727-5735.
C.J. Stewart et al., "A comparison of two laser-based methods for determination of burn scar perfusion: Laser Doppler versus laser speckle imaging", Elsevier Ltd., 2005, vol. 31, pp. 744-752.
G. J. Tearney et al., "Atherosclerotic plaque characterization by spatial and temporal speckle pattern analysis", CLEO 2001, vol. 56, pp. 307-307.
PCT International Search Report for Application No. PCT/US2007/068233 dated Feb. 21, 2008.
PCT International Search Report for Application No. PCT/US2007/060787 dated Mar. 18, 2008.
Statement under Article 19 and Reply to PCT Written Opinion for PCT International Application No. PCT/US2005/043951 dated Jun. 6, 2006.
PCT International Preliminary Report on Patentability for Application No. PCT/US2005/043951 dated Jun. 7, 2007.
Liptak David C. et al., (2007) "On the Development of a Confocal Rayleigh-Brillouin Microscope" *American Institute of Physics* vol. 78, 016106.
Office Action dated Oct. 1, 2008 for U.S. Appl. No. 11/955,986.
Invitation of Pay Additional Fees dated Aug. 7, 2008 for International Application No. PCT/US2008/062354.
Invitation of Pay Additional Fees dated Jul. 20, 2008 for International Application No. PCT/US2007/081982.
International Search Report and Written Opinion dated Mar. 7, 2006 for PCT/US2005/035711.
International Search Report and Written Opinion dated Jul. 18, 2008 for PCT/US2008/057533.
Aizu, Y et al. (1991) "Bio-Speckle Phenomena and Their Application to the Evaluation of Blood Flow" Optics and Laser Technology, vol. 23, No. 4, Aug. 1, 1991.
Richards G.J. et al. (1997) "Laser Speckle Contrast Analysis (LASCA): A Technique for Measuring Capillary Blood Flow Using the First Order Statistics of Laser Speckle Patterns" Apr. 2, 1997.
Gonick, Maria M., et al (2002) "Visualization of Blood Microcirculation Parameters in Human Tissues by Time Integrated Dynamic Speckles Analysis" vol. 972, No. 1, Oct. 1, 2002.
International Search Report and Written Opinion dated Jul. 4, 2008 for PCT/US2008/051432.
Jonathan, Enock (2005) "Dual Reference Arm Low-Coherence Interferometer-Based Reflectometer for Optical Coherence Tomography (OCT) Application" *Optics Communications* vol. 252.
Motaghian Nezam, S.M.R. (2007) "increased Ranging Depth in optical Frequency Domain Imaging by Frequency Encoding" *Optics Letters*, vol. 32, No. 19, Oct. 1, 2007.
Office Action dated Jun. 30, 2008 for U.S. Appl. No. 11/670,058.
Office Action dated Jul. 7, 2008 for U.S. Appl. No. 10/551,735.
Australian Examiner's Report dated May 27, 2008 for Australian patent application No. 2003210669.
Notice of Allowance dated Jun. 4, 2008 for U.S. Appl. No. 11/174,425.
European communication dated May 15, 2008 for European patent application No. 05819917.5.
International Search Report and Written Opinion dated Jun. 10, 2008 for PCT/US2008/051335.
Oh. W.Y. et al (2006) "Ultrahigh-Speed Optical Frequency Domain Imaging and Application to laser Ablation Monitoring" *Applied Physics Letters*, vol. 88.
Office Action dated Aug. 21, 2008 for U.S. Appl. No. 11/505,700.

(56) References Cited

OTHER PUBLICATIONS

Sticker, Markus (2002) En Face Imaging of Single Cell layers by Differential Phase-Contrast Optical Coherence Microscopy) *Optics Letters*, col. 27, No. 13, Jul. 1, 2002.
International Search Report and Written Opinion dated Jul. 17, 2008 for International Application No. PCT/US2008/057450.
International Search Report and Written Opinion dated Aug. 11, 2008 for International Application No. PCT/US2008/058703.
US National Library of Medicine (NLM), Bethesda, MD, US; Oct. 2007 (Oct. 2007), "Abstracts of the 19th Annual Symposium of Transcatheter Cardiovascular Therapeutics, Oct. 20-25, 2007, Washington, DC, USA."
International Search Report and Written Opinion dated May 26, 2008 for International Application No. PCT/US2008/051404.
Office Action dated Aug. 25, 2008 for U.S. Appl. No. 11/264,655.
Office Action dated Sep. 11, 2008 for U.S. Appl. No. 11/624,334.
Office Action dated Aug. 21, 2008 for U.S. Appl. No. 11/956,079.
Gelikono, V. M. et al. Oct. 1, 2004 "Two-Wavelength Optical Coherence Tomography" Radio physics and Quantum Electronics, Kluwer Academic Publishers-Consultants. vol. 47, No. 10-1.
International Search Report and Written Opinion for PCT/US2007/081982 dated Oct. 19, 2007.
Database Compendex Engineering Information, Inc., New York, NY, US; Mar. 5, 2007, Yelin, Dvir et al: "Spectral-Domain Spectrally-Encoded Endoscopy".
Database Biosis Biosciences Information Service, Philadelphia, PA, US; Oct. 2006, Yelin D. et al: "Three-Dimensional Miniature Endoscopy".
International Search Report and Written Opinion dated Mar. 14, 2005 for PCT/US2004/018045.
Notification of the international Preliminary Report on Patentability dated Oct. 21, 2005.
Shim M.G. et al., "Study of Fiber-Optic Probes for in vivo Medical Raman Spectroscopy" Applied Spectroscopy. vol. 53, No. 6, Jun. 1999.
Bingid U. et al., "Fibre-Optic Laser-Assisted Infrared Tumour Diagnostics (FLAIR); Infrared Tomour Diagnostics" Journal of Physics D. Applied Physics, vol. 38, No. 15, Aug. 7, 2005.
Jun Zhang et al. "Full Range Polarization-Sensitive Fourier Domain Optical Coherence Tomography" Optics Express, vol. 12, No. 24. Nov. 29, 2004.
Yonghua et al., "Real-Time Phase-Resolved Functional Optical Hilbert Transformation" Optics Letters, vol. 27, No. 2, Jan. 15, 2002.
Siavash et al., "Self-Referenced Doppler Optical Coherence Tomography" Optics Letters, vol. 27, No. 23, Dec. 1, 2002.
International Search Report and Written Opinion dated Dec. 20, 2004 for PCT/US04/10152.
Notification Concerning Transmittal of International Preliminary Report on Patentability dated Oct. 13, 2005 for PCT/US04/10152.
International Search Report and Written Opinion dated Mar. 23, 2006 for PCT/US2005/042408.
International Preliminary Report on Patentability dated Jun. 7, 2007 for PCT/US2005/042408.
International Search Report and Written Opinion dated Feb. 28, 2007 for International Application No. PCT/US2006/038277.
International Search Report and Written Opinion dated Jan. 30, 2009 for International Application No. PCT/US2008/081834.
Fox, J.A. et al; "A New Galvanometric Scanner for Rapid tuning of C02 Lasers" New York, IEEE, US vol. Apr. 7, 1991.
Motaghian Nezam, S.M. et al: "High-speed Wavelength-Swept Semiconductor laser using a Diffrection Grating and a Polygon Scanner in Littro Configuration" *Optical Fiber Communication and the National Fiber Optic Engineers Conference* Mar. 29, 2007.
International Search Report and Written Opinion dated Feb. 2, 2009 for International Application No. PCT/US2008/071786.
Bilenca A et al: "The Role of Amplitude and phase in Fluorescence Coherence Imaging: From Wide Filed to Nanometer Depth Profiling", *Optics IEEE*, May 5, 2007.
Inoue, Yusuke et al: "Varible Phase-Contrast Fluorescence Spectrometry for Fluorescently Strained Cells", *Applied Physics Letters*, Sep. 18, 2006.
Bernet, S et al: "Quantitative Imaging of Complex Samples by Spiral Phase Contrast Microscopy", *Optics Express*, May 9, 2006.
International Search Report and Written Opinion dated Jan. 15, 2009 for International Application No. PCT/US2008/074863.
Office Action dated Feb. 17, 2009 for U.S. Appl. No. 11/211,483.
Notice of Reasons for Rejection dated Dec. 2, 2008 for Japanese patent application No. 2000-533782.
International Search Report and Written Opinion dated Feb. 24, 2009 for PCT/US2008/076447.
European Official Action dated Dec. 2, 2008 for EP 07718117.0.
Barfuss et al (1989) "Modified Optical Frequency Domain Reflectometry with High spatial Resolution for Components of integrated optic Systems", IEEE vol. 7., No. 1.
Yun et al., (2004) "Removing the Depth-Degeneracy in Optical Frequency Domain Imaging with Frequency Shifting", Optics Express, vol. 12, No. 20.
International Search Report and Written Opinion dated Jun. 10, 2009 for PCT/US08/075456.
European Search Report dated May 5, 2009 for European Application No. 01991471.2.
Motz, J.T. et al: "Spectral-and Frequency-Encoded Fluorescence Imaging" Optics Letters, OSA, Optical Society of America, Washington, DC, US, vol. 30, No. 20, Oct. 15, 2005, pp. 2760-2762.
Japanese Notice of Reasons for Rejection dated Jul. 14, 2009 for Japanese Patent application No. 2006-503161.
Office Action dated Aug. 18, 2009 for U.S. Appl. No. 12/277,178.
Office Action dated Aug. 13, 2009 for U.S. Appl. No. 10/136,813.
Office Action dated Aug. 6, 2009 for U.S. Appl. No. 11/624,455.
Office Action dated May 15, 2009 for U.S. Appl. No. 11/537,123.
Office Action dated Apr. 17, 2009 for U.S. Appl. No. 11/537,343.
Office Action dated Apr. 15, 2009 for U.S. Appl. No. 12/205,775.
Office Action dated Dec. 9, 2008 for U.S. Appl. No. 09/709,162.
Office Action dated Dec. 23, 2008 for U.S. Appl. No. 11/780,261.
Office Action dated Jan. 9, 2010 for U.S. Appl. No. 11/624,455.
Office Action dated Feb. 18, 2009 for U.S. Appl. No. 11/285,301.
Beddow et al, (May 2002) "Improved Performance Interferomater Designs for Optical Coherence Tomography", IEEE Optical Fiber Sensors Conference, pp. 527-530.
Yagoob et al., (Jun. 2002) "High-Speed Wavelength-Multiplexed Fiber-Optic Sensors for Biomedicine," Sensors Proceedings of the IEEE, pp. 325-330.
Office Action dated Feb. 18, 2009 for U.S. Appl. No. 11/697,012.
Zhang et al, (Sep. 2004), "Fourier Domain Functional Optical Coherence Tomography", Saratov Fall Meeting 2004, pp. 8-14.
Office Action dated Feb. 23, 2009 for U.S. Appl. No. 11/956,129.
Office Action dated Mar. 16, 2009 for U.S. Appl. No. 11/621,694.
Office Action dated Oct. 1, 2009 for U.S. Appl. No. 11/677,278.
Office Action dated Oct. 6, 2009 for U.S. Appl. No. 12/015,642.
Lin, Stollen et al., (1977) "A CW Tunable Near-infrared (1.085-1.175-um) Raman Oscillator," Optics Letters, vol. 1, 96.
Summons to attend Oral Proceedings dated Oct. 9, 2009 for European patent application No. 06813365.1.
Office Action dated Dec. 15, 2009 for U.S. Appl. No. 11/549,397.
Poneros er al: "Optical Coherence Tomograjphy of the Biliary Tree During ERCP", Gastrointestinal Endoscopy, Elsevier, NL, vol. 55, No. 1, Jan. 1, 2002, pp. 84-88.
Fu L e tal: double-Clad Photonic Crystal Fiber Coupler for compact Nonlinear Ontical Microscopy Imaging, Optics Letters, OSA, Optical Society of America, vol. 31, No. 10, May 15, 2006, pp. 1471-1473.
Japanese language Appeal Decision dated Jan. 10, 2012 for JP 2006-503161.
Japanese Notice of Grounds for Rejection dated Oct. 28, 2011 for JP2009-294737.
Japanese Notice of Grounds for Rejection dated Dec. 28, 2011 for JP2008-535793.
Japanese Notice of Reasons for Rejection dated Dec. 12, 2011 for JP 2008-533712.
International Search Report and Written Opinion dated Feb. 9, 2012 based on PCT/US2011/034810.

(56) References Cited

OTHER PUBLICATIONS

Japanese Notice of Reasons for Rejection dated Mar. 27, 2012 for JP 2003-102672.
Japanese Notice of Reasons for Rejection dated May 8, 2012 for JP 2008-533727.
Korean Office Action dated May 25, 2012 for KR 10-2007-7008116.
Japanese Notice of Reasons for Rejection dated May 21, 2012 for JP 2008-551523.
Japanese Notice of Reasons for Rejection dated Jun. 20, 2012 for JP 2009-546534.
European Official Communication dated Aug. 1, 2012 for EP 10193526.0.
Fujimoto et al., "High Resolution in Vivo Intra-Arterial Imaging with Optical Coherence Tomography," *Official Journal of the British Cardiac Society*, vol. 82, pp. 128-133 Heart, 1999.
Rollins, et al., "In Vivo Video Rate Optical Coherence Tomography," *Optics Express*, vol. 3, pp. 219-229, Sep. 1998.
Bashkansky, et al., "Signal Processing for Improving Field Cross-Correlation Coherence Function in Optical Coherence Tomography," *Optics & Photonics News*, vol. 9, pp. 8137-8138, May 1998.
Haberland, U. H. P. et al., "Chirp Optical Coherence Tomography of Layerd Scattering Media," *Journal of Biomedical Optics*, vol. 3, pp. 259-266, Jul. 1998.
Yun, S. H. et al., "Wavelength-Swept Fiber Laser with Frequency Shifted Feedback and Resonantly Swept Intra-Cavity Acoustooptic Tunable Filter," *IEEE Journal of Selected Topics in Quantum Electronics*, vol. 3, pp. 1087-1096, Aug. 1997.
De Boer, Johannes F. et al., "Review of Polarization Sensitive Optical Coherence of Tomography and Stokes Vector Determination," *Journal of Biomedical Optics*, vol. 7, No. 3, Jul. 2002, p. 359-371.
De Boer, Johannes F. et al., "Determination of the Depth-Resolved Stokes Parameters of Light Backscattered from Turbid Media by use of Polarization-Sensitive Optical Coherence Tomography," *Optics Letters*, vol. 24, No. 5, Mar. 1, 1999, pp. 300-302.
Lu, Shih-Yau et al., "Homogeneous and Inhomogeneous Jones Matrices," *Opt. Soc. Am. A.*, vol. 11, No. 2, Feb. 1994, pp. 766-773.
Hee, Michael R. et al., "Polarization-Sensitive Low-Coherence Reflectometer for Birefringence Characterization and Ranging," *J. Opt. Soc. Am. B.*, vol. 9, for No. 6, Jun. 1992, pp. 903-908.
Pierce, Mark C. et al., "Simultaneous Intensity, Birefringence, and Flow Measurements with High-Speed Fiber-Baed Optical Coherence Tomography," *Optics Letters*, vol. 27, No. 17, Sep. 1, 2002, pp. 1534-1536.
White, Brian R. et al., "In Vivo Dynamic Human Retinal Blood Flow Imaging Using Ultra-Doppler High-Speed Spectral Domain Optical Doppler Tomography," *Optics Express*, vol. 11, No. 25, Dec. 15, 2003, pp. 3490-3497
Moreau, Julien et al., "Full-Field Birefringence Imaging by Thermal-Light Polarization-Sensitive Optical Coherence Tomography. I. Theory," *Applied Optics*, vol. 42, No. 19, Jul. 1, 2003, pp. 3800-3810.
Moreau, Julien et al., "Full-Field Birefringence Imaging by Thermal-Light Polarization-Sensitive Optical Coherence Tomography. II. Instrument and Results," *Applied Optics*, vol. 42, No. 19, Jul. 1, 2003, pp. 3811-3818.
Guo, Shuguang et al., "Depth-Resolved Birefringence and Differential Optical Axis Orientation Measurements with Finer-based Polarization-Sensitive Optical Coherence Tomography," *Optics Letters*, vol. 29, No. 17, Sep. 1, 2003, pp. 2025-2027.
Matcher, Stephen J. et al., "The Collagen Structure of Bovine Intervertebral Disc Studied Using Polarization-Sensitive Optical Coherence Tomography," *Physics in Medicine and Biology*, 2004, pp. 1295-1306.
Pierce, Mark C. et al., "Birefringence Measurements in Human Skin Using Polarizatin-Sensitive Optical Coherence Tomography," *Journal of Biomedical Optics*, vol. 9, No. 2, Mar./Apr. 2004, pp. 287-291.
Strasswimmer, John et al., "Polarization-Sensitive Optical Coherence Tomography of Invasive Basal Cell Carcinoma," *Journal of Biomedical Optics*, vol. 9, No. 2, Mar./Apr. 2004, pp. 292-298.
Andretzky, P., Lindner, M.W., Herrmann, J.M., Schultz, A., Konzog, M., Kiesewetter, F., Haeusler, G. (1999). "Optical coherence tomography by 'spectral radar': Dynamic range estimation and in vivo measurements of skin." *Proceedings of SPIE—The International Society for Optical Engineering* 3567: pp. 78-87.
Azzolini, C., F. Patelli, et al. (2001). "Correlation between optical coherence tomography data and biomicroscopic interpretation of idiopathic macular hole." *American Journal of Ophthalmology* 132(3): 348-55.
Bail, M. A. H., Gerd; Hellmann, Juergen M.; Lindner, Michael W.; Ringler, R. (1996). "Optical coherence tomography with the "spectral radar": fast optical analysis in volume scatterers by short-coherence interferometry." *Proc. SPIE*, 2925: p. 298-303.
Bardal, S., A. Kamal, et al. (1992). "Photoinduced Birefringence in Optical Fibers—a Comparative-Study of Low-Birefringence and High Birefringence Fibers." *Optics Letters* 17(6): 411-413.
Benoit, A. M., K. Naoun, et al. (2001). "Linear dichroism of the retinal nerve fiber layer expressed with Mueller matrices." *Applied Optics* 40(4): 565-569.
Blumenthal, E. Z., J. M. Williams, et al. (2000). "Reproducibility of nerve fiber layer thickness measurements by use of optical coherence tomography." *Ophthalmology* 107(12): 2278-82.
Bouzid, A., M. A. G. Abushagur, et al. "Fiber-optic four-detector polarimeter." *Optics Communications* 118(3-4): 329-334. (1995).
Bowd, C., L. M. Zangwill, et al. (2001). "Detecting early glaucoma by assessment of retinal nerve fiber layer thickness and visual function." *Investigative Ophthalmology & Visual Science* 42(9): 1993-2003.
Chauhan, B. C., J. W. Blanchard, et al. "Technique for Detecting Serial Topographic Changes in the Optic Disc and Peripapillary Retina Using Scanning Laser Tomograph." *Invest Ophthalmol Vis Sci* 41: 775-782.
Choma, M. A., C. H. Yang, et al. (2003). "Instantaneous quadrature low-coherence interferometry with 3 x 3 fiber-optic couplers." *Optics Letters* 28(22): 2162-2164.
Drexler, W., A. Baumgartner, et al. (1998). "Dual beam optical coherence tomography: signal identification for ophthalmolgoic diagnosis." *Journal of Biomedical Optics* 3 (1): 55-65.
Drexler, W., C. K. Hitzenberger, et al. (1998). "Investigation of dispersion effects in ocular media by multiple wavelength partial coherence interferometry." *Experimental Eye Research* 66(1): 25-33.
Drexler, W., U. Morgner, et al. (2001). "Ultrahigh-resolution ophthalmic optical coherence tomography." *Nature Medicine* 7(4): 502-507.
Ducros, M. G., J. D. Marsack, et al. (2001). "Primate retina imaging with polarization-sensitive optical coherence tomography." *Journal of the Optical Society of America a—Optics Image Science and Vison* 18(12): 2945-2956.
Eisenbeiss, W., J. Marotz, et al. (1999). "Reflection-optical multispectral imaging method for objective determination of burn depths." *Burns* 25(8): 697-704.
Feldchtein, F. I., G. V. Gelikonov, et al. (1998). "In vivo OCT imaging of hard and soft tissue of the oral cavity." *Optics Express* 3(6): 239-250.
Fercher, A. F., C. K. Hitzenberger, et al. (1995). "Measurement of Intraocular Distances by Backscattering Spectral Interferometry." *Optics Communications* 117(1-2): 43-48.
Fukasawa, A. and H. Iijima (2002). "Optical coherence tomography of choroidal osteoma." *American Journal of Ophthalmology* 133(3):419-21.
Gelikonov, V. M., G. V. Gelikonov, et al. (1995). "Coherent Optical Tomography of Microscopic Inhomogeneities in Biolgoical Tissues." *Jetp Letters* 61(2): 158-162.
Gil, J. J. (2000). "Characteristic properties of Mueller matrices." *Journal of the Optical Society of America a—Optics Image Science and Vision* 17(2): 328-334.
Glaessl, A., A. G. Schreyer, et al. (2001)."Laser surgical planning with magnetic resonance therapy of a venous imaging-based 3-di-

(56) References Cited

OTHER PUBLICATIONS mensional reconstructions for intralesional Nd : YAG laser therapy of a venous malformation of the neck." *Archives of Dermatology* 137:(10): 1331-1335.
Greaney, M. J., D. C. Hoffinan, et al. (2002). "Comparison of optic nerve imaging methods to distinguish normal eyes from those with glaucoma." *Investigative Ophthalmology & Visual Science* 43(1): 140-5.
Gueugniaud, P. Y., H. Carsin, et al. (2000). "Current advances in the initial management of thermal burns. [Review] [76 refs]." *Intensive Care Medicine* 26(7): 848-56.
Hausler, G., J. M. Hellmann, et al. (1996). "Observation of light propagation in volume scatterers with 10(11)-fold slow motion." *Optics Letters* 21(14): 1087-1089.
Hee, M. R., J. A. Izatt, et al. (1995). "Optical of coherence tomography of the human retina." *Archives of Ophthalmology* 113(3): 325-32.
Hellmuth, T. and M. Welle (1998). "Simultaneous measurement of dispersion, spectrum, and distance with a fourier transform spectrometer." *Journal of Biomedical Optics* 3(1): 7-11.
Hitzenberger, C. K., M. Sticker, et al. (2001). "Differential phase measurements in low-coherence interometry without 2 pi ambiguity." *Optics Letters* 26(23): 1864-1866.
Huttner, B., C. De Barros, et al. (1999). "Polarization-induced pulse spreading in birefringent optical fibers with zero differential group delay." *Optics Letters* 24(6): 370-372.
Izatt, J. A., M. D. Kulkarni, et al. (1997). "In vivo bidirectional color Doppler flow imaging of picoliter blood volumes using optical coherence tomography." *Optics Letters* 22(18): 1439-1441.
Jang, I. K., B. D. MacNeill, et al. (2002). "In-vivo characterization of coronary plaques in patients with ST elevation acute myocardial infarction using optical coherence tomography (OCT)." *Ciruculation* 106(19): 698-698 3440 Suppl. S,.
Jeng, J. C., A. Bridgeman, et al. (2003). "Laser Doppler imaging determines need for excision and grafting in advance of clinical judgment: a prospective blinded trial." *Burns* 29(7): 665-670.
Jopson, R. M., L. E. Nelson, et al. (1999). "Measurement of second-order polarization-mode dispersion vectors in optical fibers." *Ieee Photonics Technology Letters* (9): 1153-1155.
Kolios, M. C., M. D. Sherar, et al. (1995). "Large Blood-Vessel Cooling in Heated Tissues—a Numerical Study." *Physics in Medicine and Biology* 40(4): 477-494.
Laszlo, A. and A. Venetianer (1998). "Heat resistance in mammalian cells: lessons and challenges. [Review] [52 refs]." *Annals of the New Academy of Sciences* 851: 169-78.
Laufer, J., R. Simpson, et al. (1998). "Effect of temperature on the optical properties of ex vivo human dermis and subdermic." *Physics in Medicine and Biology* 43(9): 2479-2489.
Leibowitz, H. M., D. E. Krueger, et al. (1980). "The Framingham Eye Study monograph: An ophthalmological and epidemiological study of cataract, glaucoma, diabetic degeneration, and macular degeneration, and visual acuity in a general population of 2631 adults, 1973-1975." *Survey of Ophthalmology* 24(Suppl): 335-610.
Miglior, S., M. Casula, et al. (2001). "Clinical to of Heidelberg retinal tomograph examination detect glaucomatous visual field changes." *Ophthalmology* 108 (9): 1621-7.
Milner, T. E., D. M. Goodman, et al. (1995). "Depth Profiling of Laser-Heated Chromophores in Biological Tissues by Pulsed Photothermal Radiometry." *Journal of the Optical Society of America a—Optics Image Science and Vision* 12 (7): 1479-4788.
Mishchenko, M. I. and J. W. Hovenier (1995). "Depolarization of Light Backscattered by Randomly Oriented Nonspherical Particles." *Optics Letters* 20(12): 1356-&.
Mitsui, T. (1999). "High-speed detection of ballistic photons propagating through suspensions using spectral interferometry." *Japanese Journal of Applied Physics* Part 1—Regular Papers Short Notes & Review Papers 38(5A): 2978-2982.
November, L. J. (1993). "Recovery of the Matrix Operators in the Similarity and Congruency Transformations—Applications in Polarimetry." *Journal of the Optical Society of America a—Opics Image Science and Vision* 10(4): 719-739.
Park, B. H., M. C. Pierce, et al. (2005). "Real-time fiber-based multi-functional spectral-function optical coherence tomography at 1.3 mu m." *Optics Express* 13(11): 3931-3944.
Podoleanu, A. G. and D. A. Jackson (1999). "Noise analysis of a combined coherence tomograph and a confocal scanning ophthalmoscope." *Applied Optics* 38(10): 2116-2127.
Qi, B., A. P. Rimmer, et al. (2004). "Dynamic focus control in high-speed optical coherence tomography based on a microelectromechanical mirror." *Optics Communications* 232(1-6): 123-128.
Sathyam, U. S., B. W. Colston, et al. (1999). "Evaluation of optical coherence quantitation of analytes in turbid media by use of two wavelengths." *Applied Optics* 38(10): 2097-2104.
Schmitt, J. M., S. H. Xiang, et al. (1999). "Speckle in optical coherence tomography." *Journal of Biomedical Optics* 4(1): 95-105.
Schmitt, J. M., M. J. Yadlowsky, et al. "Subsurface Imaging of Living Skin with Optical Coherence Microscopy." *Dermatology* (1995). 191(2): 93-98.
Sticker, M., M. Pircher, et al. (2002). "En face imaging of single cell layers by differential phase-contrast optical coherence microscopy." *Optics Letters* 27(13): 1126-1128.
Wojtkowski, M., A. Kowalczyk, et al. (2002). "Full range complex spectral optical coherence tomography technique in eye imaging." *Optics Letters* 27(16): 1415-1417.
T. Yoshimura et al., "Statistical properties of dynamic speckles", *J. Opt. Soc. Am A*. 1986, 3(7):1032-1054
Zimnyakov et al., "A study of statistical properties of partially developed specle fields as applied to the diagnosis of structural changes in human skin", *Optics and Spectroscopy*, 1994, 76(5): 747-753.
Georgakoudi, Irene et al. (2001) "Fluorescence, Reflectance, and Light-Scattering Spectroscopy for Evaluating Dysplasia in Patients with Barrett's Esophagus" *Gastroenterology* vol. 120, pp. 1620-1629.
Poneros, John M. et al. (2001) "Diagnosis of Specialized Intestinal Metaplasia Optical Coherence Tomography" *Gastroenterology* vol. 120, pp. 7-12.
Bouma, B et al. (1995) "High Resolution Optical Coherence Tomography Imaging Using a Mode-Locked Ti: $Al_2O_3$ Laser Source" *Optics Letters* vol. 20, No. 13, pp. 1486-1488.
European Search Report dated Jun. 25, 2012 tor EP 10733985.5.
Wieser, Wolfgang et al., "Multi-Megahertz OCT: High Quality 3D Imaging at 20 million A-Scans and 4.5 Gvoxels Per Second" Jul. 5, 2010, vol. 18, No. 14, Optics Express.
European Communication Pursuant to EPC Article 94(3) for EP 07845206.7 dated Aug. 30, 2012.
International Search Report and Written Opinion dated Aug. 30, 2012 for PCT/US2012/035234.
Giuliano, Scarcelli et al., "Three-Dimensional Brillouin Confocal Microscopy". Optical Society of American, 2007, CtuV5.
Giuliano, Scarcelli et al., "Confocal Brillouin Microscopy for Three-Dimensional Mechanical Imaging." Nat Photonis, Dec. 9, 2007.
Japanese Notice of Reasons for Rejections dated Oct. 10, 2012 for 2008-553511.
W.Y. Oh et al: "High-Speed Polarization Sensitive Optical Frequency Domain Imaging with Frequency Multiplexing", Optics Express, vol. 16, No. 2, Jan. 1, 2008.
Athey, B.D. et al., "Development and Demonstration of a Networked Telepathology 3-D Imaging, Databasing, and Communication System", 1998 ("C2"), pp. 5-17.
D'Amico, A.V., et al., "Optical Coherence Tomography as a Method for Identifying Benign and Maliganat Microscope Structures in the Prostate Gland", Urology, vol. 55, Isue 5, May 2000 ("C3"), pp. 783-787.
Tearney, G.J. et al., "In Vivo Endoscopic Optical Biopsy with Optical Coherence Tomography", Science, vol. 276, No. 5321, Jun. 27, 1997 ("C6"), pp. 2037-2039.
Japanese Notice of Reasons for Rejections dated Oct. 2, 2012 for 2007-543626.
Canadian Office Action dated Oct. 10, 2012 for 2,514,189.

(56) References Cited

OTHER PUBLICATIONS

Japanese Notice of Reasons for Rejections dated Nov. 9, 2012 for JP 2007-530134.
Japanese Notice of Reasons for Rejections dated Nov. 27, 2012 for JP 2009-554772.
Japanese Notice of Reasons for Rejections dated Oct. 11, 2012 for JP 2008-533712.
Yoden, K. et al. "An Approach to Optical Reflection Tomography Along the Geometrial Thickness," Optical Review, vol. 7, No. 5, Oct. 1, 2000.
International Search Report and Written Opinion dated Oct. 25, 2012 for PCT/US2012/047415.
Joshua, Fox et al: "Measuring Primate RNFL Thickness with OCT", IEEE Journal of Selected Topics in Quantum Electronics, IEEE Service Center, Piscataway, NJ, US, vol. 7,No. 6, Nov. 1, 2001.
European Official Communication dated Feb. 6, 2013 for 04822169.1.
International Search Report dated Jan. 31, 2013 for PCT/US2012/061135.
Viliyam K. Pratt. Lazernye Sistemy Svyazi. Moskva, Izdatelstvo "Svyaz", 1972. p. 68-70.
International Search Report and Written Opinion dated Jan. 31, 2013 for PCT/US2012/060843.
European Search Report dated Mar. 11, 2013 doe EP 10739129.4.
Huber, R et al: "Fourier Domain Mode Locked Lasers for OCT Imaging at up to 290 kHz Sweep Rates", Proceedings of SPIE, SPIE—International Society for Optical Engineering, US, vol. 5861, No. 1, Jan. 1, 2005.
M. Kourogi et al: "Programmable High Speed (1MHz) Vernier-mode-locked Frequency-Swept Laser for OCT Imaging", Proceedings of SPIE, vol. 6847, Feb. 7, 2008.
Notice of Reasons for Rejection dated Feb. 5, 2013 for JP 2008-509233.
Notice of Reasons for Rejection dated Feb. 19, 2013 for JP 2008-507983.
European Extended Search Report dated Mar. 26, 2013 for EP 09825421.1.
Masahiro, Yamanari et al: "polarization-Sensitive Swept-Source Optical Coherence Tomography with Continuous Source Polarization Modulation", Optics Express, vol. 16, No. 8, Apr. 14, 2008.
European Extended Search Report dated Feb. 1, 2013 for EP 12171521.3.
Nakamura, Koichiro et al., "A New Technique of Optical Ranging by a Frequency-Shifted Feedback Laser", IEEE Phontonics Technology Letters, vol. 10, No. 12, pp. 1041-1135, Dec. 1998.
Lee, Seok-Jeong et al., "Ultrahigh Scanning Speed Optical Coherence Tomography Using Optical Frequency Comb Generators", The Japan Society of Applied Physics, vol. 40 (2001).
Kinoshita, Masaya et al., "Optical Frequency-Domain Imaging Microprofilmetry with a Frequency-Tunable Liquid-Crystal Fbry-Perot Etalon Device" Applied Optics, vol. 38, No. 34, Dec. 1, 1999.
Notice of Reasons for Rejection dated Apr. 16, 2013 for JP 2009-510092.
Bachmann A.H. et al: "Heterodyne Fourier Domain Optical Coherence Tomography for Full Range Probing with High Axial Resolution", Optics Express, OSA, vol. 14, No. 4, Feb. 20, 2006.
European Search Report for 12194876.4 dated Feb. 1, 2013.
R. Haggitt et al., "Barrett's Esophagus Correlation Between Mucin Histochemistry, Flow Cytometry, and Histological Diagnosis for Predicting Increased Cancer Risk," Apr. 1988, American Journal of Pathology, vol. 131, No. 1, pp. 53-61.
R.H. Hardwick et al., (1995) "c-erbB-2 Overexpression in the Dysplasia/Carcinoma Sequence of Barrett's Oesophagus," Journal of Clinical Pathology, vol. 48, No. 2, pp. 129-132.
W. Polkowski et al, (1998) Clinical Decision making in Barrett's Oesophagus can be supported by Computerized Immunoquantitation and Morphometry of Features Associated with Proliferation and Differentiation, Journal of pathology, vol. 184, pp. 161-168.
J.R. Turner et al., MN Antigen Expression in Normal Preneoplastic, and Neoplastic Esophagus: A Clinicopathological Study of a New Cancer-Associated Biomarker,: Jun. 1997, Human Pathology, vol. 28, No. 6, pp. 740-744.
D.J. Bowery et al., (1999) "Patterns of Gastritis in Patients with Gastro-Oesophageal Reflux Disease,", Gut, vol. 45, pp. 798-803.
O'Reich et al., (2000) "Expression of Oestrogen and Progesterone Receptors in Low-Grade Endometrial Stromal Sarcomas,", British Journal of Cancer, vol. 82, No. 5, pp. 1030-1034.
M.I. Canto et al., (1999) "Vital Staining and Barrett's Esophagus," Gastrointestinal Endoscopy, vol. 49, No. 3, Part 2, pp. S12-S16.
S. Jackie et al., (2000) "In Vivo Endoscopic Optical Coherence Tomography of the Human Gastrointestinal Tract-Toward Optical Biopsy," Encoscopy, vol. 32, No. 10, pp. 743-749.
E. Montgomery et al., "Reproducibility of the Diagnosis of Dysplasia in Barrett Esophagus: A Reaffirmation," Apr. 2001, Human Pathology, vol. 32, No. 4, pp. 368-378.
H. Geddert et al., "Expression of Cyclin B1 in the Metaplasia-Dysphasia-Carcinoma Sequence of Barrett Esophagus," Jan. 2002, Cancer, vol. 94, No. 1, pp. 212-218.
P. Pfau et al., (2003) "Criteria for the Diagnosis of Dysphasia by Endoscopic Optical Coherence Tomography,"Gastrointestinal Endoscopy, vol. 58, No. 2, pp. 196-2002.
R. Kiesslich et al., (2004) "Confocal Laser Endoscopy for Diagnosing Intraepithelial Neoplasias and Colorectal Cancer in Vivo," Gastroenterology, vol. 127, No. 3, pp. 706-713.
X. Qi et al., (2004) "Computer Aided Diagnosis of Dysphasia in Barrett's Esophagus Using Endoscopic Optical Coherence Tomography," SPIE, Coherence Domain Optical Methods and Optical Coherence Tomography in Biomedicine VIII. Proc. of Conference on., vol. 5316, pp. 33-40.
Seltzer et al., (1991) "160 nm Continuous Tuning of a MQW Laser in an External Cavity Across the Entire 1.3 µm Communications Window," Electronics Letters, vol. 27, pp. 95-96.
Office Action dated Jan. 25, 2010 for U.S. Appl. No. 11/537,048.
International Search Report dated Jan. 27, 2010 for PCT/US2009/050553.
International Search Report dated Jan. 27, 2010 for PCT/US2009/047988.
International Search Report dated Feb. 23, 2010 for U.S. Appl. No. 11/445,131.
Office Action dated Mar. 18, 2010 of U.S. Appl. No. 11/844,454.
Office Action dated Apr. 8, 2010 of U.S. Appl. No. 11/414,564.
Japanese Office Action dated Apr. 13, 2010 for Japanese Patent application No. 2007-515029.
International Search Report dated May 27, 2010 for PCT/US2009/063420.
Office Action dated May 28, 2010 for U.S. Appl. No. 12/015,642.
Office Action dated Jun. 2, 2010 for U.S. Appl. No. 12/112,205.

* cited by examiner

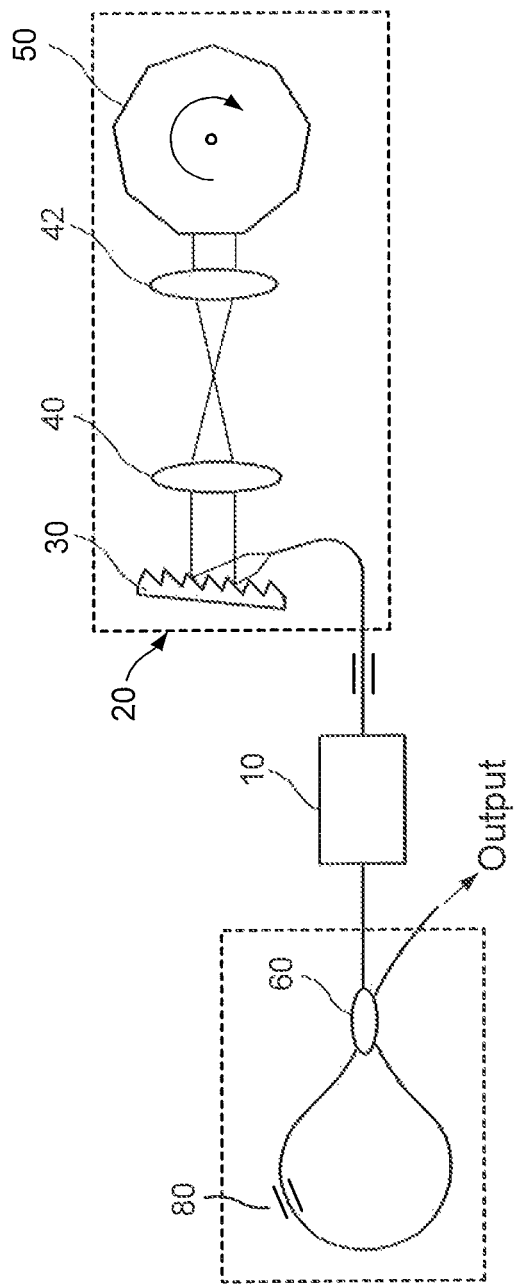
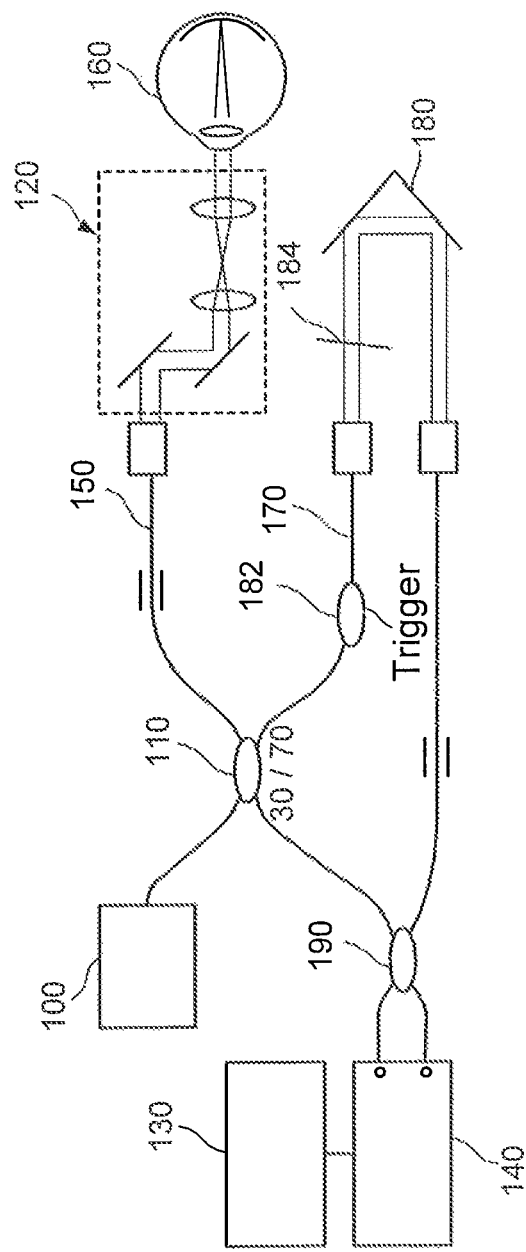
FIG. 1A
FIG. 1B

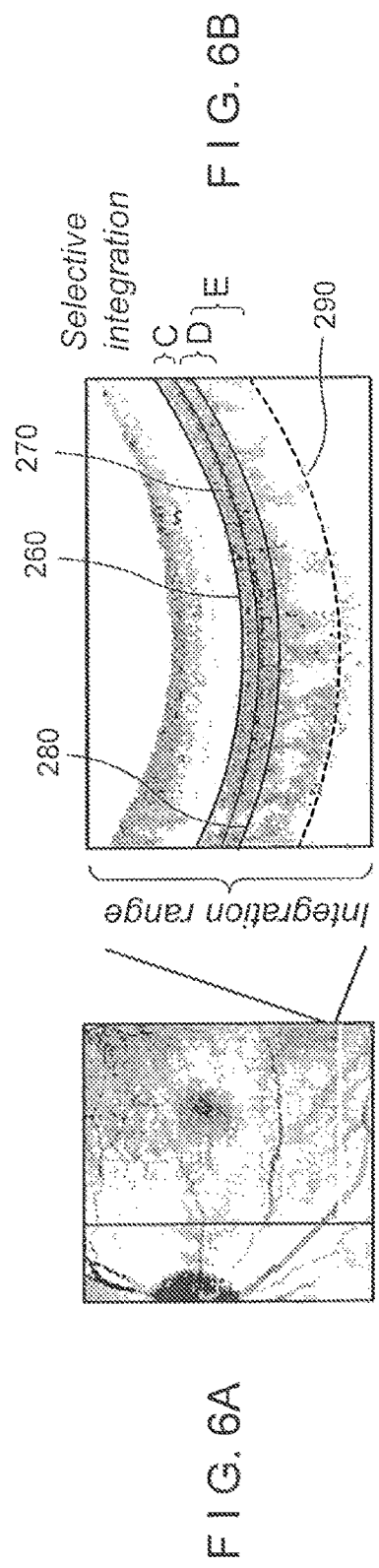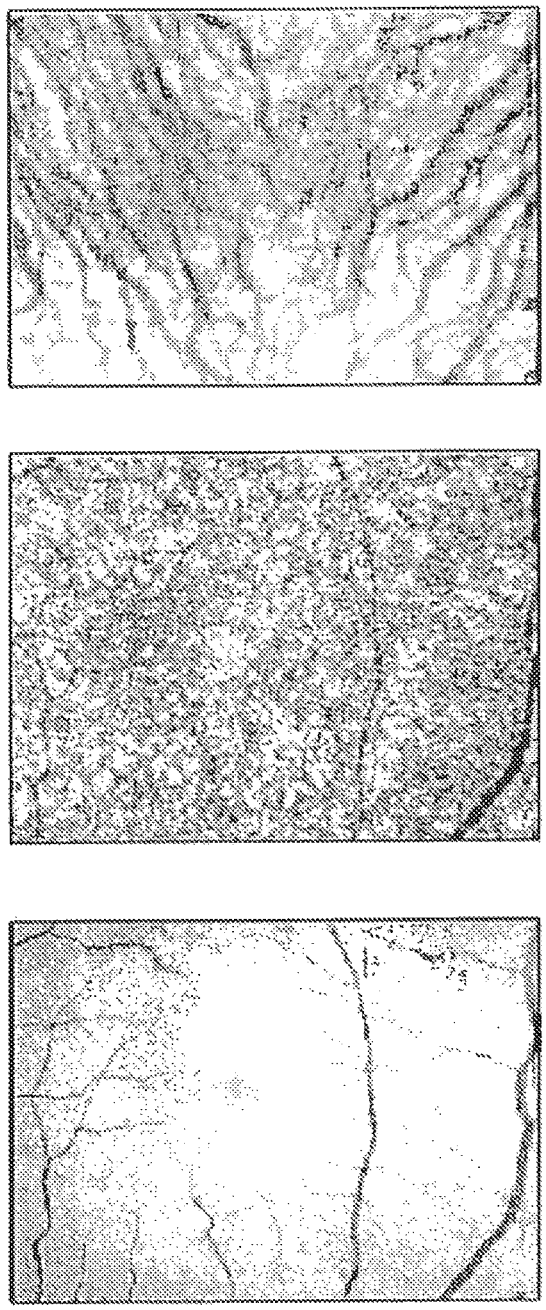
FIG. 6A  FIG. 6B  FIG. 6C  FIG. 6D  FIG. 6E

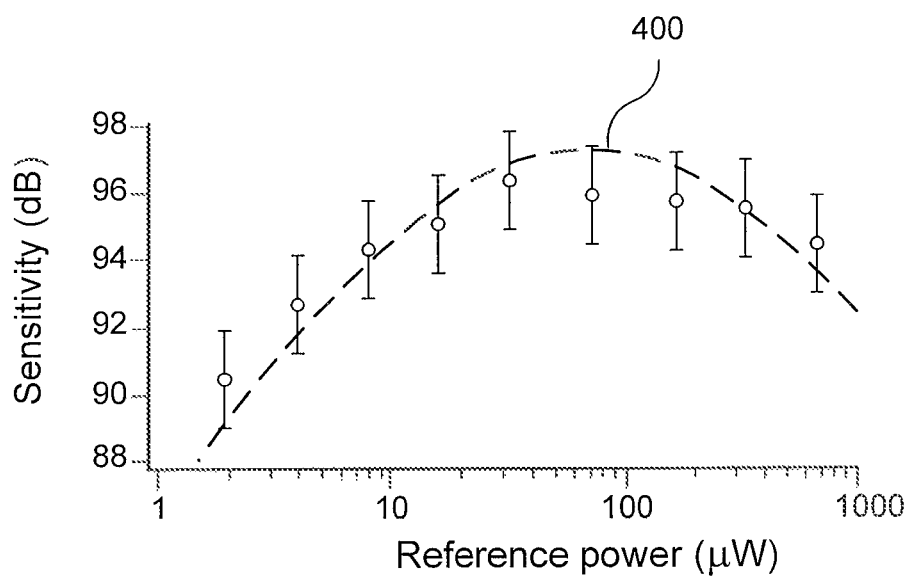
F I G. 8A
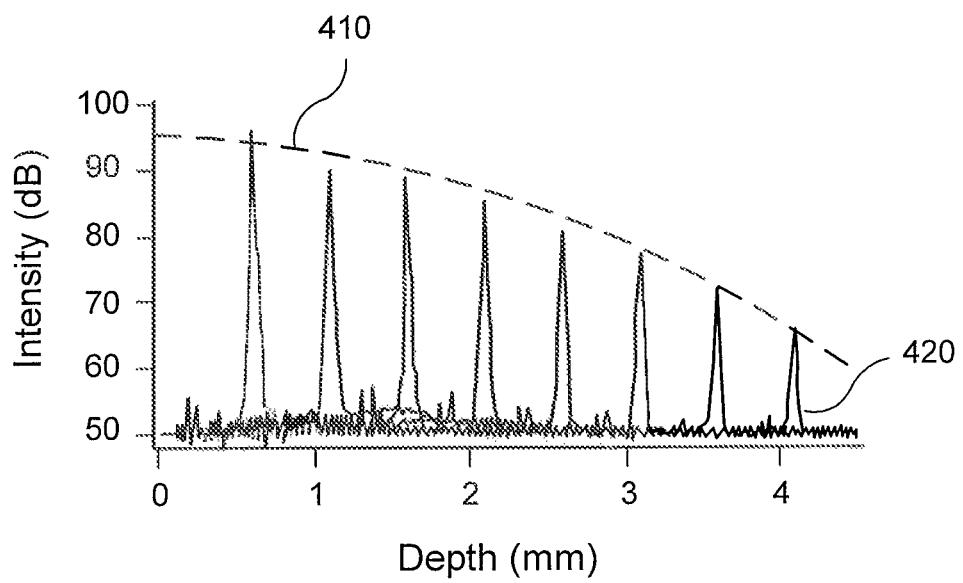
F I G. 8B

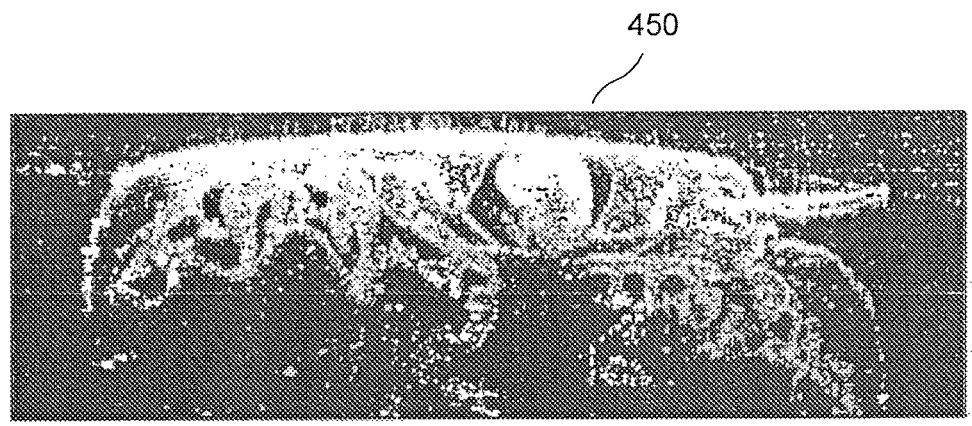
F I G. 9
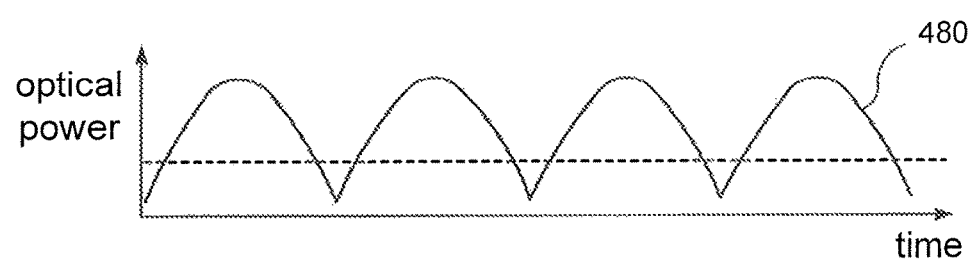
F I G. 10A
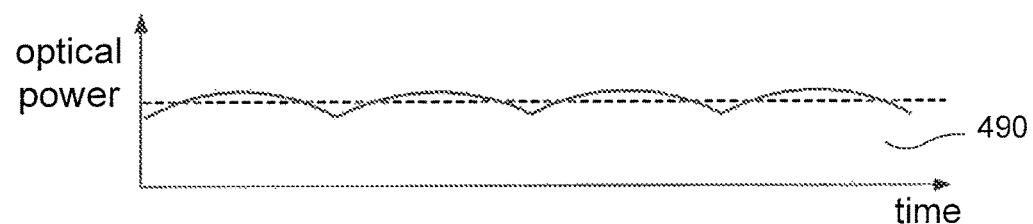
F I G. 10B

PROCESS, ARRANGEMENTS AND SYSTEMS FOR PROVIDING FREQUENCY DOMAIN IMAGING OF A SAMPLE

CROSS-REFERENCE TO RELATED APPLICATION(S)

The present application is a continuation of U.S. patent application Ser. No. 13/465,580 filed on May 7, 2012, which issues as U.S. Pat. No. 9,364,143 on Jun. 14, 2016, which is a continuation of U.S. patent application Ser. No. 11/744,287 filed May 4, 2007, which issued as U.S. Pat. No. 8,175,685 on May 8, 2012, and also claims the benefit of priority from U.S. Patent Application Ser. No. 60/799,511, filed May 10, 2006, the entire disclosures of which are incorporated herein by reference.

STATEMENT REGARDING FEDERALLY SPONSORED RESEARCH

The research leading to the present invention was supported, at least in part, by National Institute of Health—National Cancer Institute, Grant number R33 214033. Thus, the U.S. government may have certain rights in the invention.

FIELD OF THE INVENTION

The present invention relates to processes, arrangements and systems which obtain information associated with an anatomical structure or a sample using optical microscopy, and more particularly to such methods, systems and arrangements that provide optical frequency domain imaging of the anatomical structure/sample (e.g., at least one portion of an eye).

BACKGROUND INFORMATION

Optical frequency domain imaging ("OFDI"), which may also be known as swept source optical coherence tomography ("OCT"), is a technique associated with OCT concepts that generally uses a wavelength-swept light source to probe the amplitude and phase of back scattering light from tissue. Exemplary OFDI techniques and systems are described in International Application No. PCT/US04/029148. Method and system to determine polarization properties of tissue is described in International Application No. PCT/US05/039374. The OFDI technique can offer intrinsic signal-to-noise ratio ("SNR") advantage over the time-domain techniques because the interference signal can be effectively integrated through a Fourier transform. With the recently developed rapidly tunable lasers in the 1300-nm range, the OFDI technique has enabled significant improvements in, e.g., imaging speed, sensitivity, and ranging depth over the conventional time-domain OCT systems. For example, such OFDI procedures/techniques can be used for imaging skin, coronary artery, esophagus, and anterior eye segments.

While retinal imaging is an established clinical use of the OCT techniques, this application has not been implemented using the OFDI procedures because the optical absorption in the human eye at 1300 nm may be too large. The standard spectral range of the conventional ophthalmic OCT techniques has been between 800 nm and 900 nm where the humors in the eye are transparent and broadband superluminescent-diode ("SLD") light sources are readily available. It has been has suggested that the 1040-nm spectral range can be a viable alternative operating window for a retinal imaging, and can potentially offer a deeper penetration into the choroidal layers below the highly absorbing and scattering retinal pigment epithelium. The spectral domain ("SD") OCT systems, also known as Fourier domain OCT systems, that use broadband light sources at 800 nm and arrayed spectrometers have been provided to facilitate a three-dimensional retinal imaging in vivo with a superior image acquisition speed and a sensitivity to conventional time-domain OCT techniques.

As compared to the SD-OCT techniques, the OFDI procedures offer several advantages, such as an immunity to motion-induced signal fading, simple polarization-sensitive or diversity scheme, and long ranging depth. However, a clinical-viable OFDI system for imaging posterior eye segments has previously been unavailable, primarily due to the lack of a wide-tuning rapidly-swept light source in a low water absorption window. Indeed, despite the widespread use of the conventional OCT for retinal disease diagnostics, imaging posterior eye segment with OFDI has not been possible.

Accordingly, there is a need to overcome the deficiencies as described herein above.

OBJECTS AND SUMMARY OF EXEMPLARY EMBODIMENTS

To address and/or overcome the above-described problems and/or deficiencies, exemplary embodiments of systems, arrangements and processes can be provided that are capable of, e.g., utilizing the OFDI techniques to image at least one portion of the eye.

Thus, an exemplary embodiment of OFDI technique, system and process according to the present invention for imaging at least one portion of an eye can be provided. For example, a high-performance swept laser at 1050 nm and an ophthalmic OFDI system can be used that offers a high A-line rate of 19 kHz, sensitivity of >92 dB over a depth range of 2.5 mm with an optical exposure level of 550 μW, and a deep penetration into the choroid. Using the exemplary systems, techniques and arrangements according to the present invention, it is possible to perform comprehensive human retina, optic disk, and choroid imaging in vivo. This can enable a display of a choroidal vasculature in vivo, without exogenous fluorescence contrasts, and may be beneficial for evaluating choroidal as well as retinal diseases. According to another exemplary embodiment of the present invention, an OFDI system can be utilized which uses a swept laser in the 815-870 nm range, which can be used in clinical ophthalmic imaging and molecular contrast-based imaging.

Thus, according to one exemplary embodiment of the present invention, a method, apparatus and software arrangement can be provided for obtaining information associated with an anatomical structure or a sample using optical microscopy. For example, a radiation can be provided which includes at least one first electro-magnetic radiation directed to be provided to an anatomical sample and at least one second electro-magnetic radiation directed to a reference. A wavelength of the radiation can vary over time, and the wavelength is shorter than approximately 1150 nm. An interference can be detected between at least one third radiation associated with the first radiation and at least one fourth radiation associated with the second radiation. At least one image corresponding to at least one portion of the sample can be generated using data associated with the interference.

For example, a period of a variation of the wavelength of the first electro-magnetic radiation can be shorter than 1 millisecond. The anatomical sample can include at least one section of the posterior segment of an eye. The section can include a retina, a choroid, an optic nerve and/or a fovea. The wavelength may be shorter than approximately 950 nm. The wavelength can also vary by at least 10 nm over a period of a variation of the wavelength of the first electro-magnetic radiation. At least one fourth arrangement can also be provided which is capable of scanning the first electro-magnetic radiation laterally across the anatomical sample. The image may be associated with the anatomical structure of the sample and/or a blood and/or a lymphatic flow in the sample.

In one exemplary variant, the third arrangement may be capable of (i) obtaining at least one signal associated with at least one phase of at least one frequency component of the interference signal over less than an entire sweep of the wavelength, and (ii) comparing the at least one phase to at least one particular information. The particular information can be associated with a further signal obtained from a sweep of the wavelength that is different from the sweep of the wavelength of the signal. The particular information may be a constant, and/or can be associated with at least one phase of at least one further frequency component of the interference signal over less than an entire sweep of the wavelength. The frequency components may be different from one another.

In another exemplary variant, the third arrangement may be capable of generating a two-dimensional fundus-type reflectivity profile of the anatomic sample and/or a two-dimensional fundus-type image of the anatomic sample based the signal. Another arrangement may be provided which is capable of receiving the first or second electro-magnetic radiations, and providing at least one fifth electro-magnetic radiation associated with the first electro-magnetic radiation and/or the second electro-magnetic radiation The second arrangement may be further capable of detecting a further interference signal between the fifth radiation and the fourth radiation. The second arrangement may be further capable of obtaining at least one reference signal associated with a further phase of at least one first frequency component of the further interference signal over less than an entire sweep of the wavelength. The particular information may be the further phase.

According to another exemplary embodiment of the present invention, at least one source arrangement can be provided which is configured to provide an electro-magnetic radiation which has a wavelength that varies over time. A period of a variation of the wavelength of the one first electro-magnetic radiation can be shorter than 1 millisecond, and the wavelength is shorter than approximately 1150 nm. A control arrangement which is capable of modulating at least one of an optical gain or an optical loss in the at least one source arrangement over time can be provided. The optical gain may be facilitated by a semiconductor material. Another arrangement can be provided which is configured to effect a gain and/or a loss as a function of the wavelength. The wavelength may vary by at least 10 nm over the period and/or may be shorter than approximately 950 nm.

In yet another exemplary embodiment of the present invention, a method, apparatus and software arrangement can be provided. For example, first data can be received for a three-dimensional image of at least one portion of a sample. The first data may be associated with an optical interferometric signal generated from signals obtained from the sample and a reference. A region that is less than an entire portion of the first data can be converted to second data to generate a two-dimensional image which is associated with the portion of the sample. The region can be automatically selected based on at least one characteristic of the sample. The entire portion may be associated with an internal structure within the sample (e.g., an anatomical structure). For example, the region may be at least one portion of a retina and/or a choroid. The two-dimensional image may be associated with an integrated reflectivity profile of the region and/or at least one of a blood or a lymphatic vessel network. The region can be automatically selected by determining at least one location of at least one section of the region based a reflectivity in the region.

According to a further exemplary embodiment of the present invention, is possible to cause a radiation to be provided which includes at least one first electro-magnetic radiation directed to a sample and at least one second electro-magnetic radiation directed to a reference. A wavelength of the radiation varies over time. An interference signal can be detected between at least one third radiation associated with the first radiation and at least one fourth radiation associated with the second radiation. At least one signal associated with at least one phase of at least one frequency component of the interference signal can be obtained over less than an entire sweep of the wavelength. The phase may be compared to at least one particular information.

In one exemplary variant, the first electro-magnetic radiation may be scanned laterally across the sample, which may include at least one section of a posterior segment of an eye. The section can include a retina, a choroid, an optic nerve and/or a fovea. The interference signal may be associated with an integral fraction of the entire sweep of the wavelength. The fraction of the sweep may be a half or a quarter of the sweep. The signal may be associated with a flow velocity and/or an anatomical structure in the sample. The particular information may be associated with a further signal obtained from a sweep of the wavelength that is different from the sweep of the wavelength of the signal. The particular information may be a constant and/or may be associated with at least one phase of at least one further frequency component of the interference signal over less than an entire sweep of the wavelength. The frequency components may be different from one another.

These and other objects, features and advantages of the present invention will become apparent upon reading the following detailed description of embodiments of the invention, when taken in conjunction with the appended claims.

BRIEF DESCRIPTION OF THE DRAWINGS

Further objects, features and advantages of the invention will become apparent from the following detailed description taken in conjunction with the accompanying figures showing illustrative embodiments of the invention, in which:

FIG. 1(a) is a block diagram of an exemplary embodiment of a wavelength-swept laser system according to the present invention;

FIG. 1(b) is a block diagram of an exemplary embodiment of an interferometric system according to the present invention;

FIG. 6A is an exemplary two-dimensional reflectance image of the retinal and choroidal vasculature extracted from the three-dimensional OFDI data set associated with the image of FIG. 4 obtained by a conventional full-range integration method;

FIG. 6B is an exemplary fundus-type reflectivity image obtained using an exemplary embodiment of an axial-sectioning integration technique;

FIG. 6C is an exemplary retinal reflectivity image showing a shadow of a blood vasculature;

FIG. 6D is an exemplary reflectivity image obtained from an upper part of the choroids;

FIG. 6E is an exemplary image of an exemplary reflectivity image integrated from a center of the choroid showing a choroidal vasculature;

FIG. 8(a) is a graph of a sensitivity measured as a function of a reference power;

FIG. 8(b) is a graph of a sensitivity measured as a function of a depth;

FIG. 9 is an exemplary OFDI image of a Xenopus laevis tadpole in vivo acquired using another exemplary embodiment of the system, arrangement and process according to the present invention;

FIG. 10(a) is a graph of an exemplary output of a shaped spectra without a gain/loss modulation generated as a function of wavelength using another exemplary embodiment of the system, arrangement and process according to the present invention;

FIG. 10(b) is a graph of an exemplary output of the shaped spectra with the gain/loss modulation generated as a function of wavelength using an exemplary embodiment of the system, arrangement and process according to the present invention;

Figure 2B:
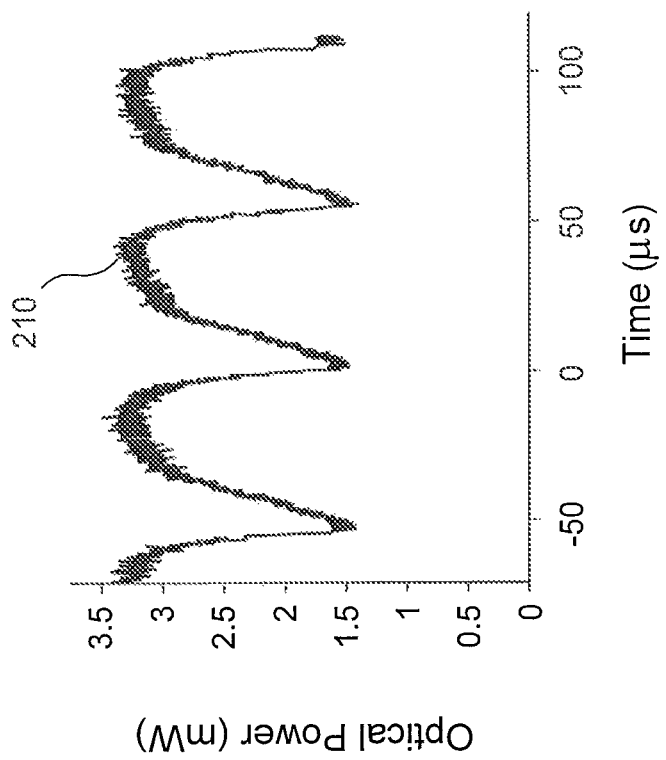
FIG. 2(b) is a graph illustrating measured output characteristics of a time-domain output trace.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF EXEMPLARY EMBODIMENTS

First Exemplary Embodiment of Laser Source System

FIG. 1(a) depicts an exemplary embodiment of a laser source system (e.g., which can include a 1050 nm swept laser source) provided in a linear cavity configuration according to the present invention. As shown in this figure, a gain medium 10 can be provided, such as a bi-directional semiconductor optical amplifier (QPhotonics, Inc., QSOA-1050) which may be driven at an injection current level of 400 mA. One port of the amplifier can be coupled to a wavelength-scanning filter 20 that may comprise a diffraction grating 30 (1200 lines/mm), a telescope consisting of two lenses 40, 42 with respective focal lengths of 100 and 50 mm, and a polygon mirror scanner 50 (e.g., Lincoln Lasers, Inc., 40 facets). The design bandwidth and free spectral range of the filter can be approximately 0.1 nm and 61 nm, respectively. The amplifier's other port can be spliced to connect to a loop mirror which may include a 50/50 coupler 60. A Sagnac loop 70 can also act as an output coupler.

The reflectivity and output coupling ratio can be complementary, and may be optimized by adjusting a polarization controller 80 to tune the amount of the birefringence-induced non-reciprocity in the loop. The linear-cavity configuration can also be used instead of or together with conventional ring cavity designs, since low-loss low-cost circulators and isolators may not be readily available at 1050 nm. Sweep repetition rates of up to 36 kHz may be achieved with 100% duty cycle, which may represent a significant improvement over previously demonstrated swept lasers in the 1050 nm region that offered tuning rates of <1 kHz. In an OFDI system according to one exemplary embodiment of the present invention, the laser can be operated at a wavelength sweep rate of about 18.8 kHz, thus producing a polarized output with an average output power of 2.7 mW.

Exemplary Embodiment of Imaging System

FIG. 1(b) depicts an exemplary embodiment of an optical frequency domain imaging (OFDI) system according to the present invention. For example, it is possible to use a swept laser can be used as a light source 100. This exemplary system further comprises a fiber-optic interferometer 110, a beam scanner 120, a detector 130 and a computer 140. A sample arm 150 (e.g., 30% port) can be connected to a two-axis galvanometer scanner apparatus 120 which may be designed for a retinal imaging. A focal beam size can be approximately 10 µm in tissue (e.g., index=1.38). The optical power level at an entrance pupil of an eye 160 can be measured to be about 550 µW, which is well below the 1.9-mW maximum exposure level at λ=1050 nm according to the ANSI laser safety standards. A reference arm 170 (e.g., 70% port) can utilize a transmission-type variable delay line 180 and a 10% tap coupler 182 to generate sampling trigger signals for acquiring data.

As shown in FIG. 1(b), a neutral density (ND) attenuator 184 may be used to obtain an optimal reference-arm power. Light returning from the sample can be combined with the reference light at a 50/50 coupler 190. Resulting interference signals can be measured using an InGaAs dual-balanced detector 140 (e.g., New Focus, Inc., 1811). A signal provided by the balanced detector 140 can be further amplified (e.g., by 10 dB), low-pass filtered, and digitized at 10 MS/s using, e.g., a 12-bit data acquisition board (National Instruments, Inc., PCI-6115). For example, when sampling a 512 samples during each A-line scan, the imaging depth range determined by the spectral sampling interval can be about 2.44 mm in air.

Exemplary Laser Output Characteristics

Figure 2A:
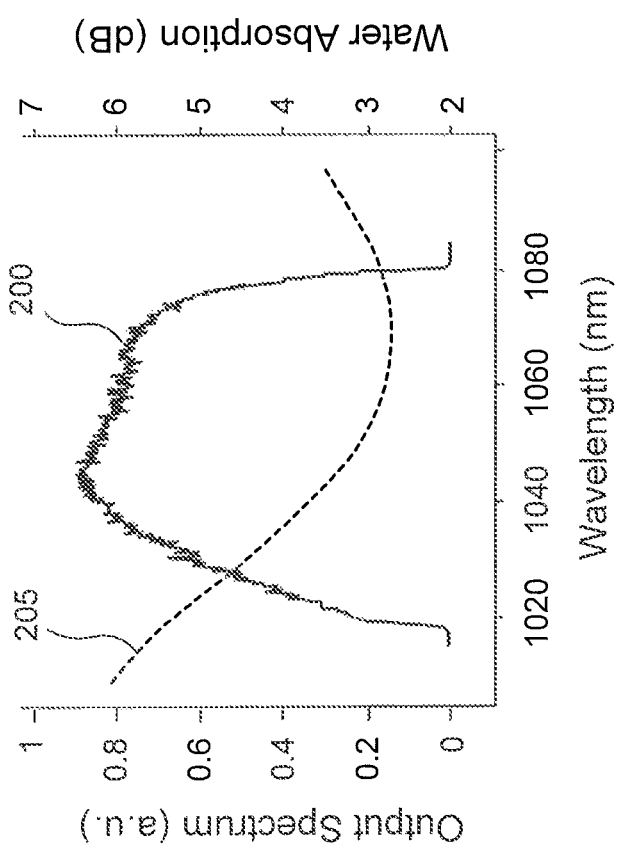
FIG. 2(a) is a graph illustrating measured output characteristics of a peak-hold output spectrum and an optical absorption in water for a particular propagation distance corresponding to a roundtrip in typical human vitreous.

FIG. 2(a) depicts an exemplary output spectrum measured using an optical spectrum analyzer in peak-hold mode (with resolution=0.1 nm). The exemplary output spectrum spanned from 1019 to 1081 nm over a range of 62 nm determined by the free spectral range of the filter. The spectral range coincided with a local transparent window of the eye. The roundtrip optical absorption in human vitreous and aqueous humors can be estimated to be between about 2 dB and 5 dB based on known absorption characteristics of water (as shown in FIG. 2(a)). Using a variable-delay Michelson interferometer, it is possible to measure the coherence length of the laser output, defined as the roundtrip delay resulting in 50% visibility, to be approximately 4.4 mm in air. From this value, it is possible to determine an instantaneous line width of laser output to be 0.11 nm. In FIG. 2(a), a peak-hold output spectrum 200 and an optical absorption curve 205 are provided in water for a 42-mm propagation distance corresponding to a roundtrip in a typical human vitreous.

FIG. 2(b) shows a graph of a time domain exemplary oscilloscope output trace 210 of a laser output indicating 100% tuning duty cycle at 18.8 kHz (single shot, 5-MHz detection bandwidth). The y-axis of the trace graph of FIG. 2(b) represents an instantaneous optical power. The total power of amplified spontaneous emission (ASE) in the output, measured by blocking the intracavity beam in the polygon filter, is shown as about 1.1 mW. Since ASE is significantly suppressed during lasing, it is expected that the ASE level in the laser output may be negligible. The laser output exhibited significant intensity fluctuations (~10% pp) due to an etalon effect originating from relatively large facet reflections at the SOA chip with a thickness equivalent to 2.5 mm in air. In the exemplary embodiment of the imaging system, the etalon effect can cause ghost images (−30 dB) by optical aliasing.

Exemplary Sensitivity and Resolution of Imaging System

An exemplary embodiment of the OFDI system and exemplary optimized operating parameters can be provided to maximize the SNR using a partial reflector (neutral density filter and metal mirror) as a sample. An exemplary preferable reference arm power for maximal SNR may be 2.6 µW at each detection port. This relatively low value can be attributed to the relatively large intensity noise of the laser that may not be completely suppressed in the dual balanced detection. Exemplary data processing according to an exemplary embodiment of the present invention can include reference subtraction, envelope apodization or windowing, interpolation to correct for nonlinear k-space tuning, and dispersion correction. For example, subtracting the reference from the interference signals can eliminate image artifacts due to a non-uniform spectral envelope of the laser source. Apodizing the interference fringes by imposing a appropriate windowing technique can decrease the sidebands of point spread functions and improve image contrast.

This exemplary embodiment of the process according to the present invention may come at a resolution loss and SNR (due to a reduced integration time). It is possible to use a Gaussian window to yield a desirable compromise in contrast and resolution (e.g., at 1050-nm). Since the detector signal may not be sampled in constant time intervals, whereas the tuning curve of our laser was not linear in k-space, interpolating the interference signal may be preferable to reduce or avoid image blurring. Upon completing the exemplary interpolation, the signal may be further corrected for the chromatic dispersion in the interferometer as well as in the sample, e.g., by multiplying a predetermined phase function.

Figure 3:
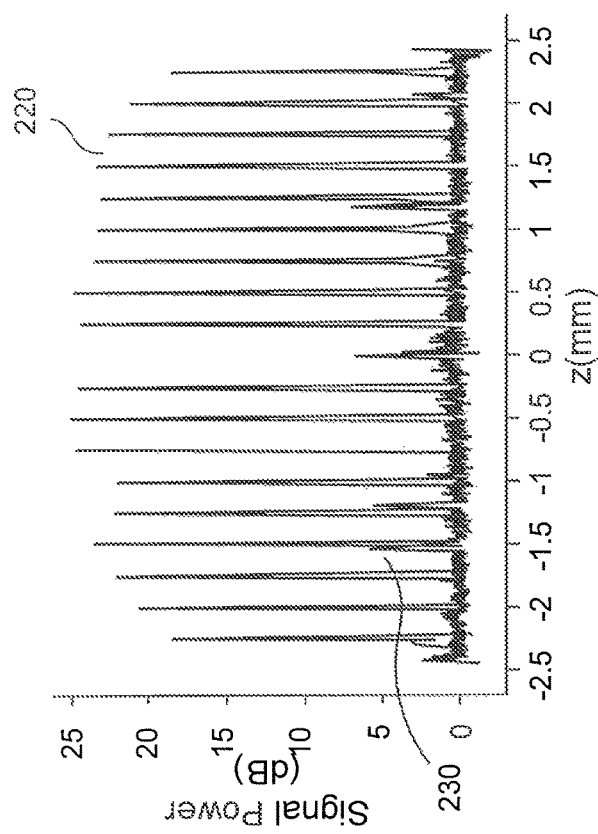
FIG. 3 is a graph illustrating point spread functions measured at various path length differences.

FIG. 3 shows exemplary A-line profiles and/or point spread functions 220 measured at various path length differences of the interferometer. For this measurement, we used a neutral density attenuator (73 dB) and gold-coated mirror in the sample arm, and the path length was varied by moving the reference mirror. The maximum SNR is 25 dB that corresponds to a maximum sensitivity of 98 dB. The theoretical shot-noise limit of sensitivity is calculated to be 109 dB; the 11-dB deficiency in sensitivity of our system seems reasonable, considering that the residual laser intensity noise, imperfect polarization alignment between the sample and reference light, and Gaussian windowing, among many other practical details, contributed to SNR loss. For example, to facilitate the exemplary SNR analysis, each exemplary curve plotted was obtained by an average over 500 consecutive scans at a constant depth, and a simple numerical subtraction was performed to make the noise floor flat. Ghost artifacts marked as asterisks 230 were caused by the etalon effect in the laser source are shown in this figure.

As indicated in FIG. 3, the sensitivity was decreased to 92 dB as the path length increased to a depth of 2.4 mm, due to the finite coherence length of the laser output. As compared to the conventional time-domain systems that use a broadband source at 1040 nm, the exemplary embodiment of the system according to the present invention provides a higher sensitivity, e.g., at a 100-fold faster image acquisition speed and one sixth of sample arm power. The high sensitivity and depth range of the exemplary embodiment of the system according to the present invention compare favorably with exemplary SD-OCT systems that use broadband sources in the 800-900 nm spectral range. Due to the absorption by water in the eye, the actual SNR for the human retina is likely 3-4 dB lower than the values measured with the mirror sample. Based on the source spectrum (as shown in FIG. 2(a)) and the Gaussian window function used, the theoretical axial resolution can be determined to be about 13 μm in air; the measured values may be 14-16 μm, increasing with the depth. Errors in interpolation and dispersion compensation due to higher order terms may account for the discrepancy.

Exemplary Video-rate Imaging of Retina, Optic Disk, and Choroid in vivo

Figure 4:
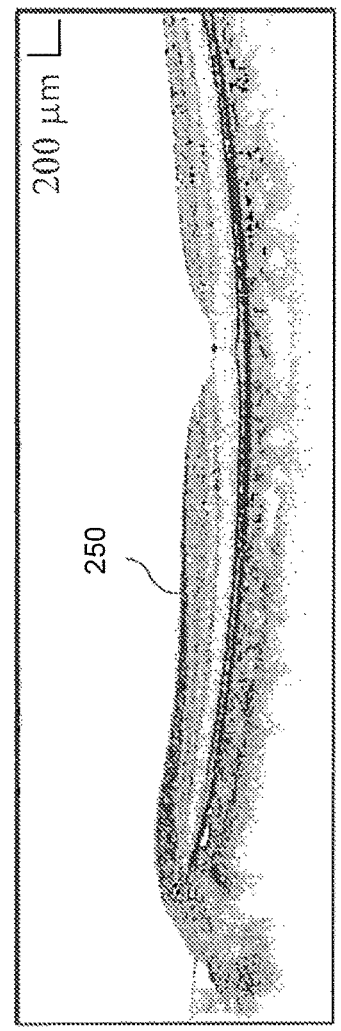
FIG. 4 is an exemplary image of retina and choroid obtained from a healthy volunteer using the exemplary embodiment of the . system, process and arrangement according to the present invention.

Exemplary OFDI imaging was conducted on two healthy volunteers (A: 36-year-old Asian male, B: 41-year-old Caucasian male) using the exemplary embodiments of the system, process and arrangement according to the present invention. The exemplary OFDI system acquired 18,800 A-lines continuously over 10-20 seconds as the focused sample beam was scanned over an area of 6 mm (horizontal) by 5.2 mm (vertical) across the macular region in the retina. FIG. 4 shows a sequence 250 of images of the fovea and optic disk of the sample recorded from volunteer A at a frame rate of 18.8 Hz in 10.6 seconds. Each image frame was constructed from 1,000 A-line scans with an inverse grayscale table mapping to the reflectivity range over 47 dB, with each frame spanning over 6.0 mm (horizontal) and 1.8 mm (depth) in tissue. For example, 200 frames were acquired in 10.6 seconds to screen a tissue area with a vertical span of 5.2 mm. The anatomical layers in the retina are visualized and correlate well with previously published OCT images and histological findings.

Figure 5A:
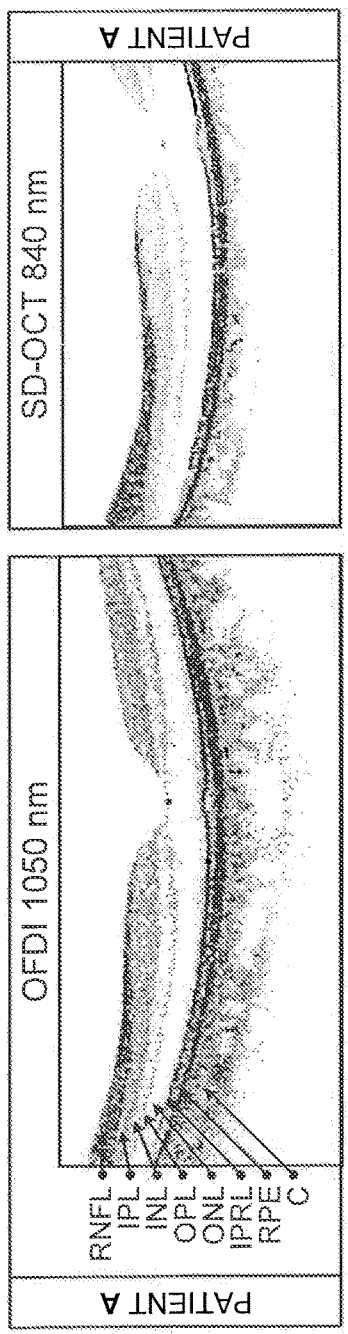
FIG. 5(a) is a first exemplary OFDI image at fovea and optic nerve head of a patient A produced by an exemplary system at one location.

FIG. 5A depicts an expanded exemplary image of fovea extracted from the three-dimensional data set using the exemplary embodiments of the system, process and arrangement according to the present invention. The exemplary OFDI image of FIG. 5A indicates a deep penetration into the choroid nearly up to the interface with the sclera, visualizing densely-packed choroidal capillaries and vessels.

To assess the penetration of the exemplary embodiments of the system, process and arrangement according to the present invention, the two volunteers A and B can be three-dimensionally imaged using both the OFDI system and the SD-OCT system previously developed for video-rate retinal imaging. The SD-OCT system employed a super luminescent diode with a center wavelength of 840 nm and a 3-dB spectral bandwidth of 50 nm, offering an axial resolution of 8-9 nm in air. At an A-line rate of 29 kHz and a sample arm power level of 600 the SD-OCT system offered a peak sensitivity of 98 dB at zero delay that decreased to 82 dB at the maximum ranging depth of 2.2 mm in air.

Figure 5B:
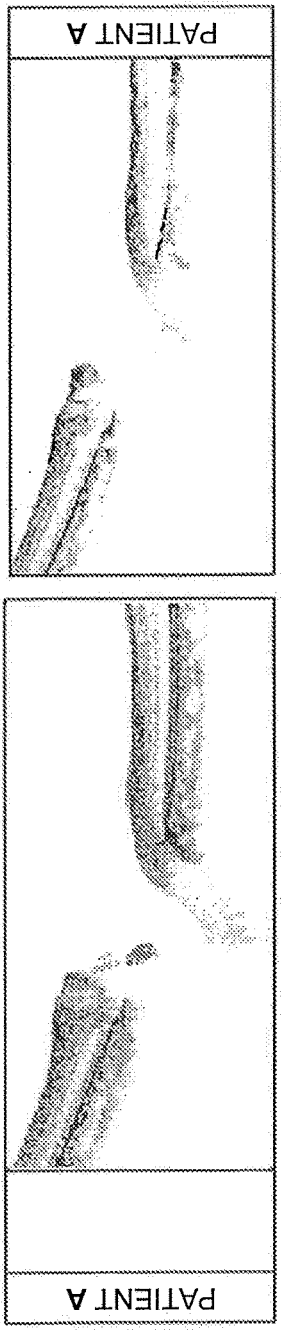
FIG. 5(b) is a second exemplary OFDI image at the fovea and the optic nerve head of the patient A produced by another exemplary system at such location.
Figure 5C:
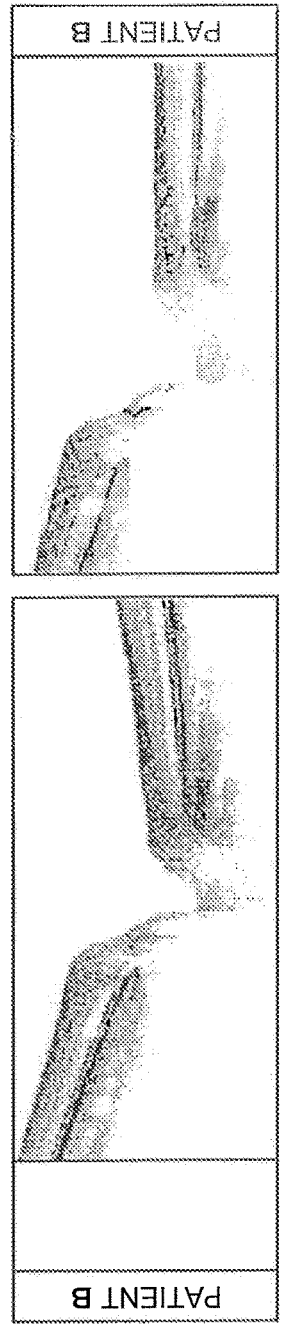
FIG. 5(c) is a first exemplary SD-OCT image at the fovea and the optic nerve head of the patient A as a similar location produced by an exemplary system according to the present invention.
Figure 5D:
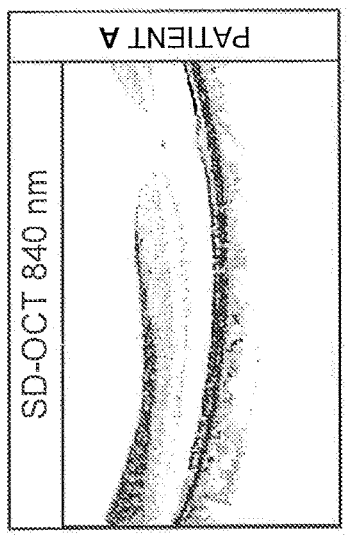
FIG. 5(d) is a second exemplary SD-OCT image at the fovea and the optic nerve head of the patient A as the location of FIG. 5(c) produced by an exemplary system according to the present invention.
Figure 5E:
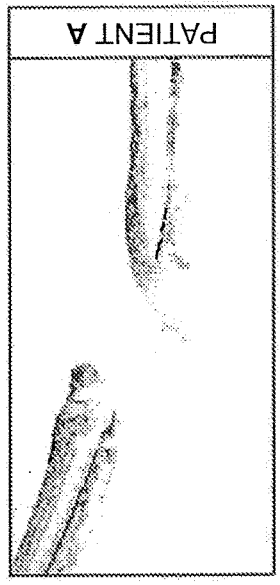
FIG. 5(e) is a third exemplary OFDI image obtained from a patient B produced by another exemplary system according to the present invention.
Figure 5F:
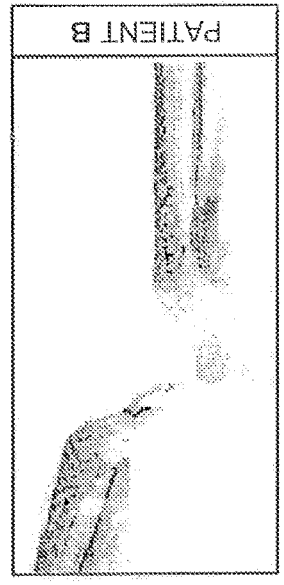
FIG. 5(f) is a fourth exemplary OFDI image obtained from the patient B produced by a further exemplary system according to the present invention.

FIGS. 5A-5F illustrate side-by-side comparisons of the OFDI and SD-OCT images near the foveae and optic disks of the two volunteers A and B. For example, FIGS. 5A and 5C shows OFDI images at fovea and optic nerve head from the volunteer A. FIGS. 5B and 5D illustrate SD-OCT images from the same person at similar tissue locations. FIGS. 5E and 5F provide the OFDI and SD-OCT images, respectively, obtained from volunteer B. For example, as shown, the OFDI images exhibit considerably deeper penetration in tissue than the SD-OCT images in most if not in all data sets. Such large penetration depth may stem from both the high system sensitivity and long source wavelength. Despite the relatively large axial resolution of ~11 μm in tissue, the OFDI system can visualize the anatomical layered structure in the retina (as shown in FIG. 5A), RNFL, retinal nerve fiber layer, IPL, inner plexiform layer, INL; inner nuclear layer, OPL; outer plexiform layer, ONL; outer nuclear layer, IPRL; interface between the inner and outer segments of the photoreceptor layer, RPE; retinal pigmented epithelium, and C; choriocapillaris and choroid.

As shown in these figures, the OFDI images exhibit considerably deeper penetration into the choroid compared to the SD-OCT images, whereas the higher axial resolution in the SD-OCT images provide better contrast between retinal layers. The lower absorption and scattering in RPE at 1050 nm than 840 nm may account for the apparently superior penetration of the OFDI system to the SD-OCT system with a comparable sensitivity.

Visualization of Retinal/Choroidal Vasculature with OFDI Techniques/Systems

With the three-dimensional tomographic data of the eye's posterior segment, the pixel values along the entire depth axis can be integrated to produce a two-dimensional fundus-type reflectivity image. FIG. 6A shows an exemplary integrated reflectivity image generated from the entire OFDI image sequence shown in FIG. 4, with the image being two-dimensional reflectance image (5.3×5.2 mm$^2$) obtained with the conventional full-range integration method. The exemplary image shows the exemplary optical nerve head, fovea, retinal vessels, and an outline of the deep choroidal vasculature. However, the depth information is not indicated. To address this deficiency of the image generated by a conventional method, it is possible to integrate only selective regions according to using the exemplary embodiment of the system, process and arrangement of the present invention.

For example, according to one exemplary embodiment of the present invention, in order to visualize the retinal vasculature with a maximum contrast, it is possible to integrate the reflectivity in the range between IPRL and RPE 260, 270 as shown in FIG. 6B. This figure shows an Illustration of an exemplary embodiment of a axial-sectioning integration technique for producing fundus-type reflectivity images. The shadow or loss of signal created by the retinal vessels above can appear most distinctly. Integrating over the entire retina including the vessel often results in a lower contrast in the vasculature because retinal blood vessels produce large signals by strong scattering. Automatic image processing conveniently allowed for automatic segmentations of the IPRL and RPE layers 260, 270.

FIG. 6C depicts an exemplary reflectivity image (shadow) of a blood vasculature (3.8×5.2 mm$^2$) of the retina vessels. Using the thin integration region below the RPE, it is also possible to obtain fundus-type reflectivity images of the choriocapillary layer containing abundant small blood vessels and pigment cells obtained from an upper part of the choroid, as shown in FIG. 6D. To obtain an image of the complete choroidal region, it is possible to utilize an integration range indicated by references 280 and 290 of FIG. 6B. The choroidal vasculature is shown in the exemplary resulting reflectivity image of FIG. 6E which is an exemplary reflectivity image integrated from the center of the choroid revealing the choroidal vasculature. Reflectivity images with similar qualities can be obtained from volunteer B.

Exemplary Implementation of Exemplary Embodiments of Invention

Experimental results show that the images generated using the exemplary OFDI techniques at 1050 nm can provide a comprehensive imaging of the human retina and choroid with high resolution and contrast. However, the exemplary embodiment of the OFDI system according to the exemplary embodiments of the present invention may provide an order-of-magnitude higher image acquisition speed than with the use of the conventional time-domain OCT systems, and avails the choroid images with an enhanced contrast in comparison to the SD-OCT system at 840 nm.

The enhanced penetration makes it possible to obtain depth-sectioned reflectivity images of the choroid capillary and vascular networks. Fundus camera or scanning laser ophthalmoscope have been conventionally used to view vasculatures. However, such methods may require fluoresce in or indocyanine green angiography to have access to the choroid except for patients with significantly low level of pigmentations.

The exemplary OFDI system according to the present invention includes a wavelength-swept laser produced using, e.g., a commercial SOA and custom-built intracavity scanning filter. such laser's output power, tuning speed and range may yield a sensitivity of about 98 dB, A-line rate of 19 kHz, and resolution of 10 μm in tissue. Increasing the saturation power and gain of SOA and reducing the extended-cavity loss can possibly further improve the sensitivity and resolution (tuning range). For example, the power exposure level of the exemplary embodiment of the system according to the present invention can be only 550 μW, whereas the maximum ANSI limit at 1050 nm is likely to be 1.9 mW.

Exemplary Embodiment of Swept Laser Source

Figure 7A:
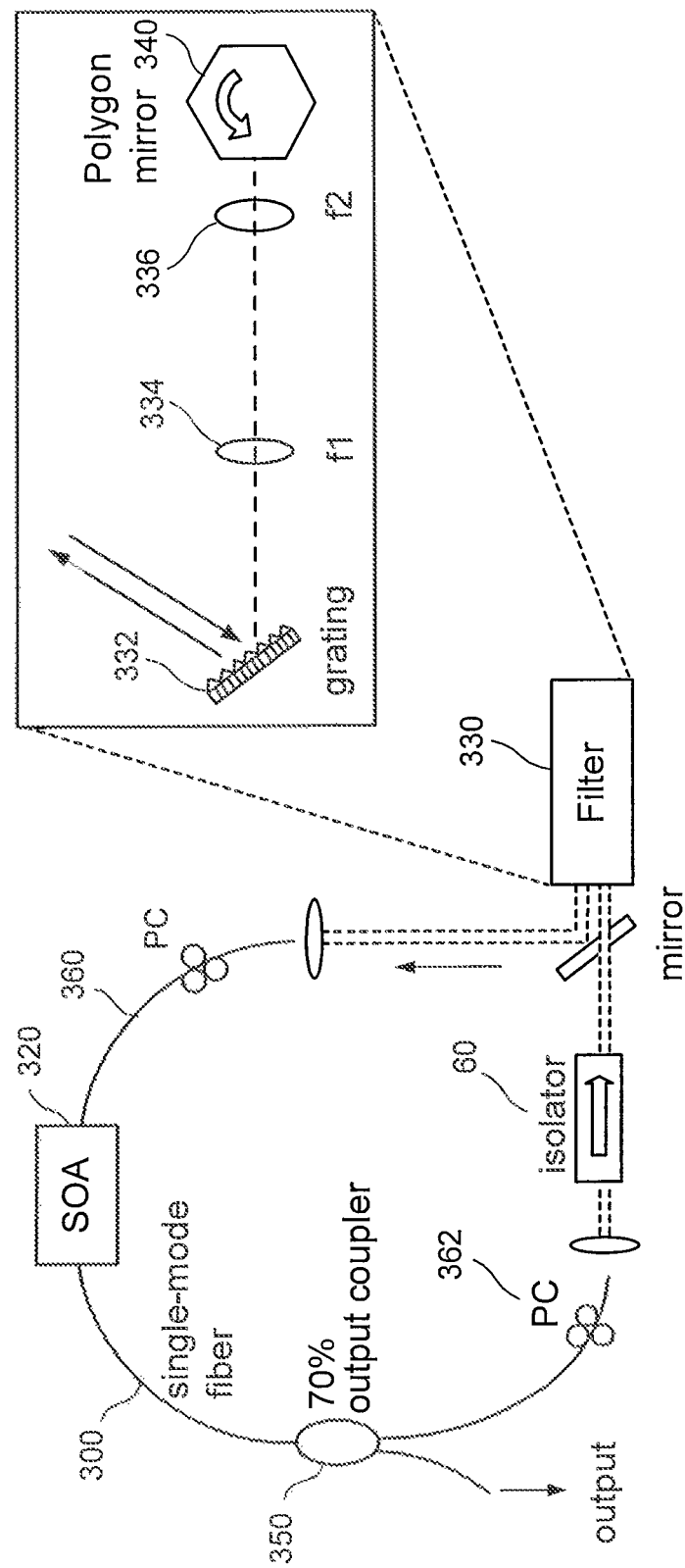
FIG. 7(a) is a schematic diagram of an exemplary embodiment of the wavelength-swept laser arrangement according to the present invention.

FIG. 7(a) shows another exemplary embodiment of a swept laser source arrangement according to the present invention, e.g., in the 815-870 nm spectral range. The swept laser source arrangement can include a fiber-optic unidirectional ring cavity 300 with a free-space isolator 310. The gain medium 320 may be a commercially-available semiconductor optical amplifier (e.g., SOA-372-850-SM, Superlum Diodes Ltd.). An intracavity spectral filter 330 can be provided which may comprise a diffractive grating (e.g., 830 grooves/mm) 332, two achromatic lenses 334, 336 in the 4f configuration, and a 72-facet polygon mirror 340 (Lincoln lasers, Inc.). The polygon can be rotated at about 600 revolutions per second to produce unidirectional sweeps from short to long wavelengths at a repetition rate of 43.2 kHz.

The free-space collimated beam in the cavity may have a size of about 1 mm FWHM (full width at half maximum). The beam incident angle to the grating normal can be 67 deg. The focal lengths of the two lenses 334, 336 in the telescope can be 75 ($f_1$) and 40 ($f_2$) mm, respectively. It is possible to predict a free-spectral range of 55 nm and FWHM filter bandwidth of 0.17 nm. The laser output can be obtained via a 70% port of a fiber-optic coupler 350. Two polarization controllers 360, 362 can be used to maximize the output power and tuning range.

Figure 7C:
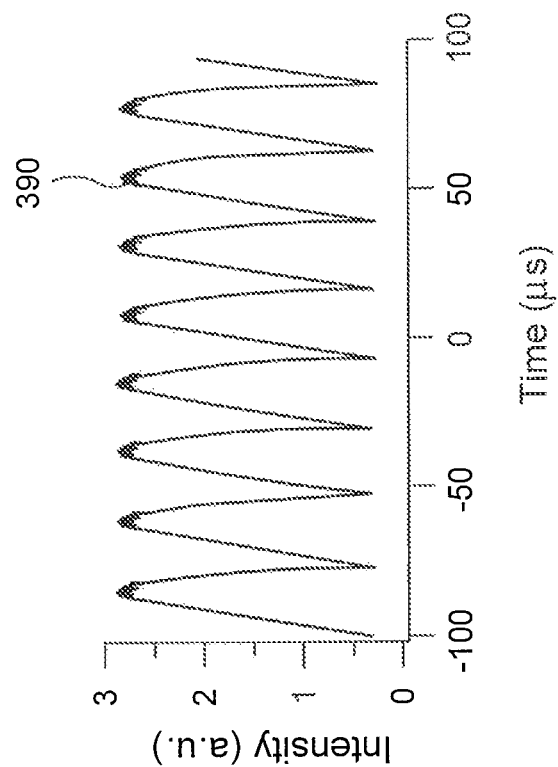
FIG. 7(c) is a graph of a oscilloscope trace generated using the exemplary embodiment of FIG. 7(a)
Figure 7B:
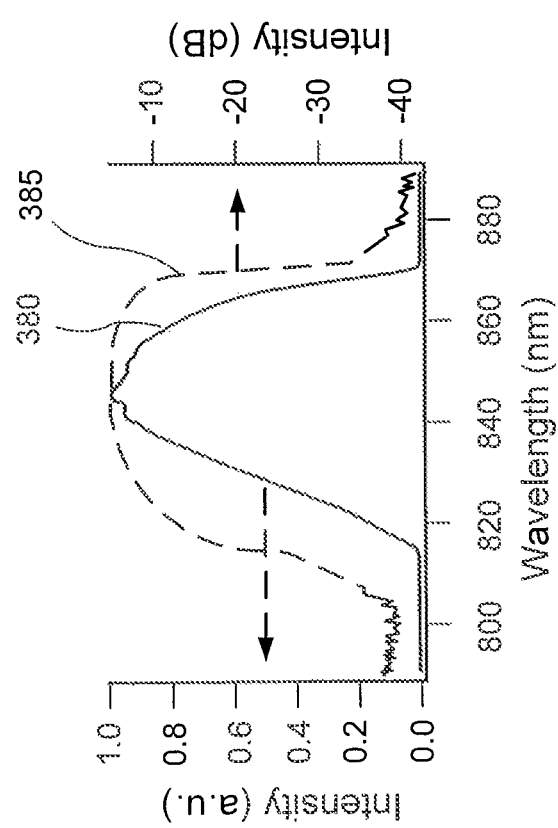
FIG. 7(b) is a graph of a peak-hold output spectrum of the signals generated using the exemplary embodiment of FIG. 7(a)

For example, it is possible to measure the spectral and temporal characteristics of the laser output at a sweep rate of about 43.2 kHz. The SOA may be driven with an injection current of about 110 mA. FIG. 7(b) shows an exemplary output spectrum 380, 385 measured with an exemplary optical spectrum analyzer in a peak-hold mode at a resolution bandwidth of 0.1 nm. The total tuning range is 55 nm from 815 to 870 nm with a FWHM bandwidth of 38 nm. A stability of the output power is provided in the single-shot oscilloscope trace 390 as shown in FIG. 7(c) provided at a about 43.2 kHz sweep rate and 7 mW averaged power. The peak power variation across tuning cycles may be less than 1%. The instantaneous laser emission can contain multiple longitudinal modes.

An exemplary measurement of the coherence length (as shown in FIG. 3(b)) can indicate that the FWHM line width may be approximately 0.17 nm corresponding to the filter bandwidth. The intensity noise characteristic of the laser output may further be characterized by using an electrical spectrum analyzer (e.g., Model, Agilent) and low-gain Silicon detector. The measured relative intensity noise can range from about −125 dB/Hz to −135 dB/Hz decreasing with the frequency in the frequency range of about 2 MHz to 10 MHz. The noise peaks due to longitudinal mode beating can appear at 91 MHz. The time-average output power may be about 6.9 mW.

The large output coupling ratio of the exemplary embodiment of the laser source arrangement, e.g., about 70%, can ensure that the peak power at the SOA does not exceed about 20 mW, e.g., the specified optical damage threshold of the SOA. When this condition is not satisfied, a sudden catastrophic or slowly progressing damage may occur at the output facet of SOA chip. Increasing the optical damage threshold of the 800-nm SOA chips, e.g., by new chip designs, can improve the tuning range as well as the long-term reliability. The output may contain a broadband amplified spontaneous emission that can occupy ~8% (about 0.56 mW) of the total average power.

Exemplary Imaging System

An exemplary embodiment of the OFDI system according to the present invention can be provided using the exemplary wavelength-swept laser arrangement. The configuration of the exemplary system can be similar to the system shown in FIG. 1(b). The laser output can be split into two paths in an interferometer by a 30/70 coupler. In one path (e.g., 30% port, termed "sample arm") may illuminate a biological sample via a two-axis galvanometer scanner (e.g., Model, Cambridge Technologies). The other path, "reference arm," generally provides a reference beam. The signal beam returning from the sample by backscattering is combined with the reference beam at, e.g., a 50/50 coupler, thus producing interference.

The interference signal may be detected with a dual-balanced silicon receiver (e.g., DC-80 MHz, 1807-FS, New Focus). The receiver output is low-pass filtered (35 MHz) and digitized at a sampling rate of 100 MS/s with a 14-bit data acquisition board (e.g., DAQ, NI-5122, National Instruments). A small portion (10%) of the reference beam can be tapped and detected through a grating filter to provide triggers to the DAQ board. During each wavelength sweep or A-line scan, a large number, e.g., 2048 samples can be acquired. The sampled data may initially be stored in an on-board memory or on another storage device.

Upon collecting a desired number of A-line scans, the data set may be transferred to a host personal computer, either to the memory/storage arrangement for on-line processing and/or display or to the hard disk for post processing. When only a single frame is acquired at a time, the exemplary system is capable of processing and displaying the image frame in real time at a frame refresh rate of about 5 Hz. For larger data sets, an exemplary 256 MB on-board memory provides for acquisition of up to 65,536 A-line scans consecutively for about 1.3 sec. This corresponds to about 128 image frames, each consisting of 512 A-lines. Post data processing techniques can include reference subtraction, apodization, interpolation into a linear k-space, and dispersion compensation prior to Fourier transforms.

To characterize and optimize the exemplary embodiment of the system, process and arrangement according to the present invention, it is possible to use an axial point spread function (or A-line) by using a partial mirror as the sample (−50 dB reflectivity). FIG. 8(a) shows a graph 400 of the sensitivity of the exemplary system measured as a function of the reference optical power. The reference power can be varied by using a variable neutral density (ND) filter in the reference arm. Throughout this measurement, for example, the path length difference between the sample and reference arms may be about 0.6 mm, and the optical power returning from the attenuated sample mirror can be 3.3 nW at each port of the 50/50 coupler. The sensitivity values may be determined by adding the sample attenuation (e.g., about 50 dB) to the measured signal-to-noise ratios (SNR). The reference power can be measured at one of the ports of the 50/50 coupler, corresponding to the time-average reference power at each photodiode. At reference powers between about 30 µW and 200 µW, a maximum sensitivity of ~96 dB may be obtained.

The sensitivity in the unit of decibel may be expressed as: $S_{dB} = S_0 - 10 \log_{10}(1 + a/P_r + P_r/b) - \Delta$, where $S_0$ denotes the shot-noise limited sensitivity, $P_r$ is the reference power level, a and b correspond to the reference power levels at which the thermal and intensity noise, respectively, become equal to that of the shot noise in magnitude, and $\Delta$ can be a fitting parameter associated with other factors contributing to the loss of sensitivity. Taking into account amplified spontaneous emission, $S_0$ may be about 107 dB. For example, a=17 µW from the detector noise level (e.g., 3.3 pA/√Hz) and conversion efficiency (e.g., 1 A/W). Based on the relative intensity noise of the laser (e.g., −130 dB/Hz) and an 18-dB common-noise suppression efficiency of the balanced receiver, b=280 µW. For example, the best fit to the experimental data 410 of FIG. 8(*b*) can be obtained with $\Delta$=8 dB. FIG. 8(*b*) shows a graph of the sensitivity 420 measured as a function of depth. This exemplary value may be largely attributed to the simplified model assuming a flat reference spectrum, a polarization mismatch between the sample and the reference light, and the apodization step in data processing, each possibly contributing to a loss of sensitivity by a couple of dB's.

Due to a finite coherence length of the laser source, the sensitivity can decrease as the interferometric delay increases. It is possible to measure axial point spread functions at various depth locations of the sample mirror by changing the delay in the reference arm while maintaining the reference power at about 100 µW per photodiode, as shown in the graph of FIG. 8(*b*). For example, each axial profile can be calibrated by measuring the noise floor obtained by blocking the sample arm, and then matching the noise floor to a 50 dB level. In this manner, the modest frequency or depth dependence (~2 dB) of the noise floor can be reduced or eliminated. Thus, the sensitivity can drop by about 6 dB at a depth of about 1.9 mm. From a Gaussian fit (dashed line), the instantaneous laser line width may be about 0.17 nm. The FWHM of the axial profile, or the axial resolution in air, can be about 8 µm in the depth from zero to B mm. This corresponds to an axial resolution of ~6 µm in tissue imaging (e.g., refractive index, n 1.35).

As an example, to confirm and demonstrate the capabilities of the exemplary embodiment of the system, process and arrangement according to the present invention for high-speed high-resolution biological imaging, images of *Xenopus laevis* tadpoles may be obtained in vivo by scanning the sample beam (B-mode scan). The sample beam can have a confocal parameter of about 250 µm and a FWHM beam size of approximately 7 µm at the focus in air (n=1). The optical power on the sample may be about 2.4 mW. During the imaging procedure, the tadpole (stage 46) can be under anesthesia in a water bath by a drop of about 0.02% 3-aminobenzoic acid ethyl ester (MS-222).

FIG. 9 shows a sequence of images 450 obtained as the beam is scanned in one dimension repeatedly over the ventricle in the heart. The image sequence was acquired at a frame rate of 84.4 Hz (512 A-lines per frame) in the duration of 1.2 s, but is displayed at a reduced rate of 24 frames per second. Each frame, cropped from the original (500×1024 pixels), has 400×200 pixels and spans a dimension of 3.3 mm (horizontal) by 1.1 mm (depth, n=1.35). The motion of the ventricle including trabeculae can be seen. The ability to image the beating heart with high spatial and temporal resolution may be useful for investigating normal and abnormal cardiac developments in vivo. Combined with contrast agents such ICG and gold nano particles developed in the 800-nm region, the exemplary embodiment of the OFDI system, process and arrangement according to the present invention can enable high-speed functional or molecular imaging.

Exemplary Laser Current Modulation

An exemplary preferred light source arrangement for OFDI imaging generally has a flat output spectrum. To obtain such desired spectral profile, it is possible to modulate the gain or loss of a gain medium or a filter inside or outside a laser cavity. The filter may be a broadband variable attenuator, and its transmission may be controlled synchronously with laser tuning. The exemplary filter may be a passive spectral filter with a desired transmission spectrum. The gain medium can preferably be a semiconductor optical amplifier, and its gain may be varied by modulating the injection current to the amplifier synchronously with filter tuning. FIGS. 10(*a*) and 10(*b*) illustrate graphs of exemplary output tuning traces 480, 490 without and with the use of an exemplary embodiment of a modulation method according to the present invention, respectively. This exemplary method can also be effective to maximize or at least increase the output power and tuning range for a given optical damage threshold of the semiconductor gain chip.

Exemplary Flow Measurement

The ability to detect and quantify the blood flow in the eye retina and choroid can have impacts in several clinical applications such as for an evaluation of age-related macular degeneration. Several methods of extracting the flow information from the phase of the OFDI signals are known in the art. These exemplary conventional methods, however, require a significant beam overlap between two consecutive A-line scans-over sampling, thus causing undesirable compromise between the phase accuracy and image acquisition speed. Using the exemplary embodiment of the system, process and arrangement according to the present invention, instead of comparing the phase values of two A-line scans, it is possible to extract multiple phase values corresponding to different time points or wavelengths within a single A-line and compare the values with reference phase values. This exemplary procedure provides for a measurement of the flow velocity at multiple time points during a single A-line scan, permitting a faster beam scan and image acquisition speed. Such procedure can be used at decreased phase or velocity measurement accuracy, which is likely to be acceptable in many applications.

Figure 11:
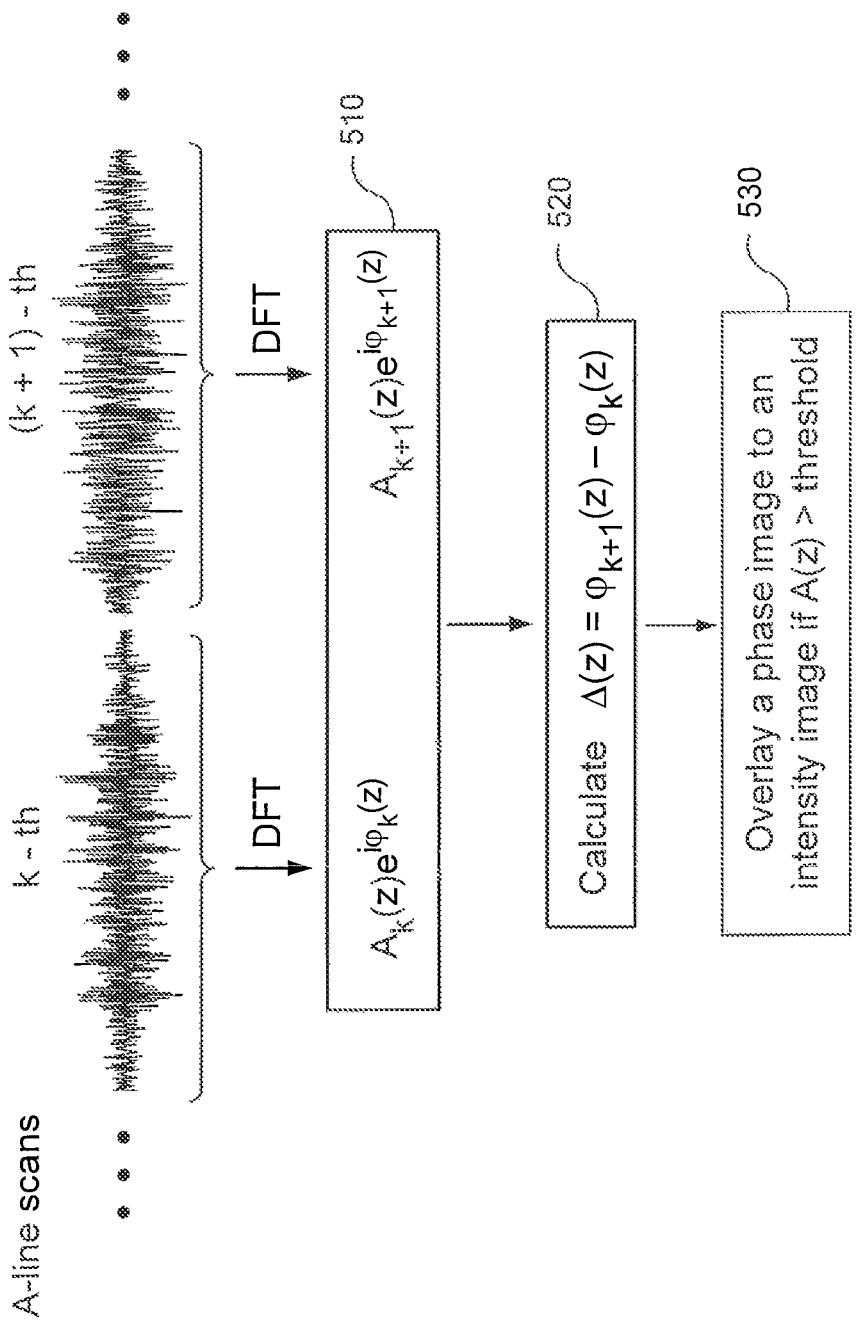
FIG. 11 is a flow diagram of a conventional method to obtain Doppler OFDI signals.

FIG. 11 illustrates a flow diagram of a conventional method to extract the phase and velocity information from an entire dataset obtained during each wavelength scan. As shown in FIG. 10, A-line scans, k-th through (k+1)-th are provided. In step 510, DFT from each of such scans is received, and utilized in the formulas $A_k(z)e^{i\varphi_k(z)}$ and $A_k(z)e^{i\varphi_{k+1}(z)}$, respectively. Then, using the determined results in step 510, the following determination is made in step 520: $\Delta(z) = \varphi_{k+1}(z) - \varphi_k(z)$. Then, in step 530, a phase image is overlayed to an intensity image if A(z) is larger than a particular threshold. Here, $A_m(z)$ denotes the signal amplitude associated with the sample reflectance at a depth z at the m-th A-line scan, $\varphi_m(z)$ denotes the signal phase associated with a depth z at the m-th A-line scan, and Δ(z) represents a difference between the phases.

Figure 12:
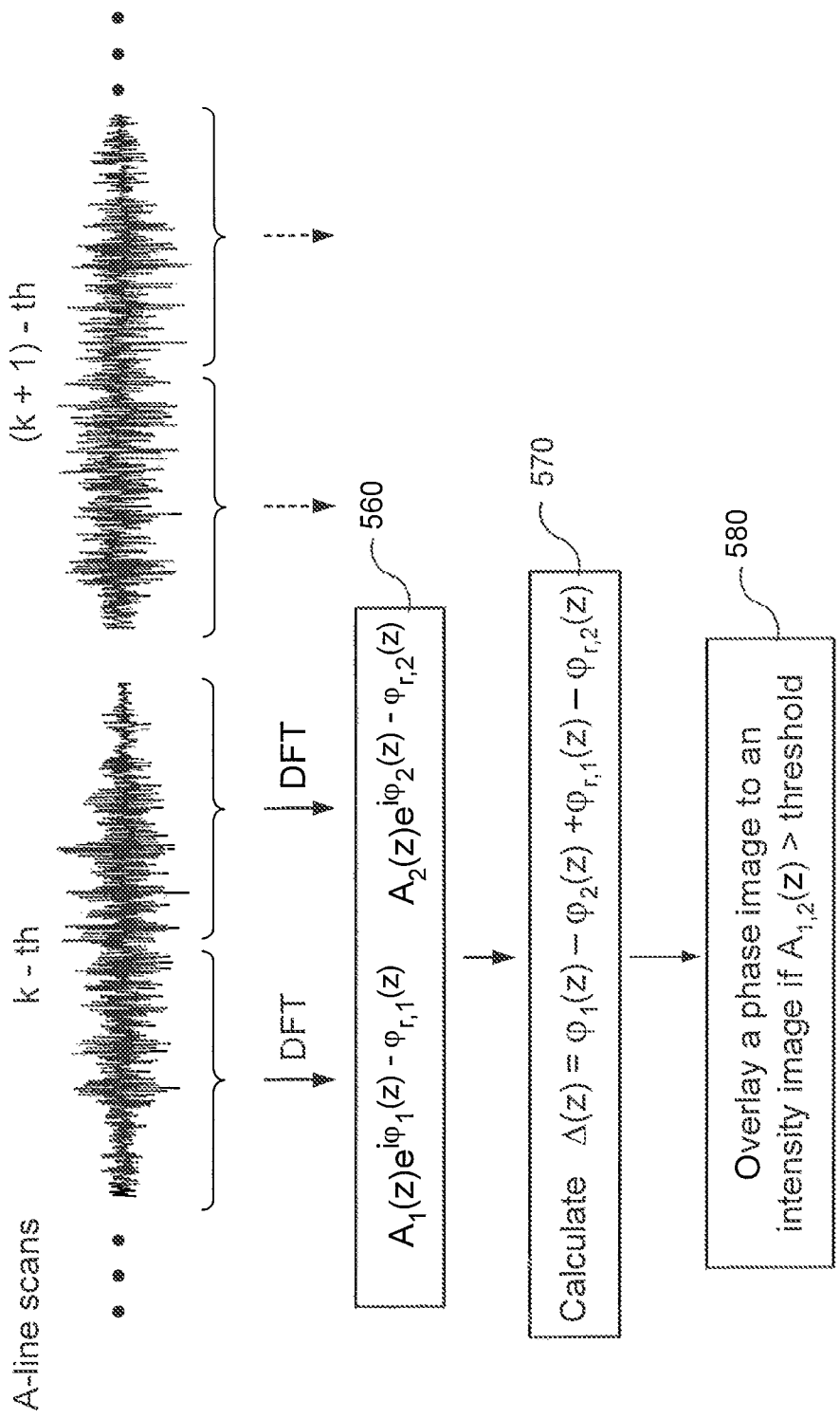
FIG. 12 is a flow diagram of an exemplary embodiment of a process to obtain Doppler OFDI signals by processing a portion of an interference fringe according to the present invention.

FIG. 12 illustrates a flow diagram of the exemplary embodiment of the process according to the present invention which can be used to obtain the phase and flow information by processing a half of the interference fringe data. For example, similarly to the conventional method shown in FIG. 11, A-line scans, k-th through (k+1)-th are provided. Then, in step 560, DFT from each of such scans is received, and utilized in the following formulas, respectively: $A_1(z)e^{i\varphi_1(z)-\varphi_{r,1}(z)}$, $A_2(z)e^{i\varphi_2(z)-\varphi_{r,2}(z)}$, etc. Using the results obtained from step 560, the following determination is made in step 570: $\Delta(z)=\varphi_1(z)-\varphi_2(z)+\varphi_{r,1}(z)-\varphi_{r,2}(z)$. Here, $A_1(z)$ and $A_2(z)$ denote the signal amplitudes obtained from the two different portions of the interference signal acquired in each A-line scan, $\varphi_1(z)$ and $\varphi_2(z)$ denote the signal phases obtained from the two different portions of the interference signal, and $\varphi_{r,1}(z)$ and $\varphi_{r,2}(z)$ denote reference phases that may be constants, phases obtained from an auxiliary interferometric signal, or phases associated with a different depth. By subtracting the reference phases from the signal phases, phase noise associated with sampling timing fluctuations and motion artifacts can be greatly reduced. Further, in step 580, a phase image is overlayed to an intensity image if A(z) is larger than a particular threshold. This exemplary process can also be applicable to beam-scanning phase microscopy.

Figures 13A, 13B:
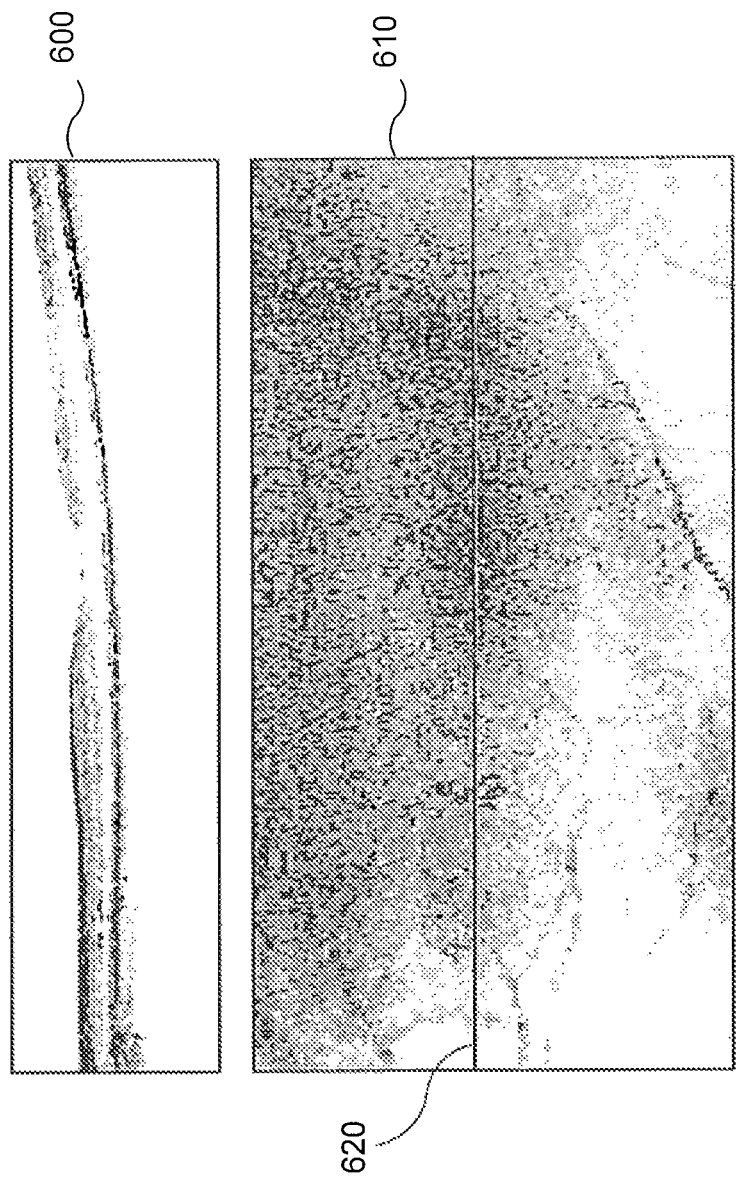
FIG. 13(a) is an exemplary single image of the retina which includes the fovea and optic disk obtained from a healthy volunteer consecutively acquired at a large number of frames.
FIG. 13(b) is an exemplary integrated fundus image of the retina generated from multiple cross-sectional images covering an area by integrating the intensity in each depth profile.

FIGS. 13(*a*) and 13(*b*) show exemplary images image of the retina obtained from a healthy volunteer. For example, FIG. 13(*a*) illustrates a single exemplary image from a large number of frames consecutively acquired using the exemplary embodiment of the system, process and arrangement according to the present invention. The image frame consists of about 1000 axial lines, and the exemplary image shows the fovea and optic disk of the patient. FIG. 13(*b*) shows an exemplary Integrated fundus image produced from multiple cross-sectional images covering an area by integrating the intensity in each depth profile to represent a single point in the fundus image using the exemplary embodiment of the system, process and arrangement according to the present invention.

As shown in these figures, the retinal OFDI imaging was performed at 800-900 nm in vivo on a 41-year-old Caucasian male subject. The exemplary embodiment of the OFDI system, process and arrangement according to the present invention acquired 23 k A-lines continuously over 1-2 seconds as the focused sample beam was scanned over an area including the macular and optic nerve head region in the retina. Each image frame was constructed from 1,000 A-line scans with an inverse grayscale table mapping to the reflectivity range. The anatomical layers in the retina are clearly visualized and correlate well with previously published OCT images and histological findings.

The foregoing merely illustrates the principles of the invention. Various modifications and alterations to the described embodiments will be apparent to those skilled in the art in view of the teachings herein. Indeed, the arrangements, systems and methods according to the exemplary embodiments of the present invention can be used with any OCT system, OFDI system, SD-OCT system or other imaging systems, and for example with those described in International Patent Application PCT/US2004/029148, filed Sep. 8, 2004, U.S. patent application Ser. No. 11/266,779, filed Nov. 2, 2005, and U.S. patent application Ser. No. 10/501,276, filed Jul. 9, 2004, the disclosures of which are incorporated by reference herein in their entireties. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. An apparatus comprising:
   at least one light source configured to provide a light radiation;
   a splitter configured to separate the light radiation into at least one first electro-magnetic radiation directed to an anatomical sample and at least one second electro-magnetic radiation directed to a reference, wherein the anatomical sample includes at least one section, and wherein a wavelength of the light radiation provided by the at least one light source varies over time, and the wavelength is shorter than approximately 1150 nm;
   at least one interferometer configured to interfere at least one third radiation associated with the at least one first radiation and at least one fourth radiation associated with the at least one second radiation to generate an interference signal;
   at least one detector configured to detect the interference signal; and
   at least one computer configured to generate at least one image corresponding to at least one portion of the anatomical sample using data associated with the interference signal.

2. The apparatus according to claim 1, wherein a period of a variation of the wavelength of the at least one first electro-magnetic radiation by the at least one light source is shorter than 1 millisecond.

3. The apparatus according to claim 1, wherein the at least one section includes at least one of a retina, a choroid, an optic nerve, or a fovea.

4. The apparatus according to claim 1, wherein the wavelength is shorter than approximately 950 nm.

5. The apparatus according to claim 1, wherein the wavelength is varied with the at least one light source by at least 10 nm over a period of a variation of the wavelength of the at least one first electro-magnetic radiation.

6. The apparatus according to claim 1, further comprising at least one scanner which is configured to scan the at least one first electro-magnetic radiation laterally across the anatomical sample.

7. The apparatus according to claim 1, wherein the anatomical sample has an anatomical structure and the at least one image is associated with the anatomical structure of the anatomical sample.

8. The apparatus according to claim 7, wherein the at least one image is further associated with at least one of a blood or a lymphatic flow in the anatomical sample.

9. The apparatus according to claim 1, wherein the at least one computer is configured and specifically programmed to (i) obtain at least one signal associated with at least one phase of at least one frequency component of the interference signal over less than an entire sweep of the wavelength, and (ii) compare the at least one phase to at least first information.

10. The apparatus according to claim 9, wherein the first information is at least one of (i) associated with a further signal obtained from a sweep of the wavelength that is different from the sweep of the wavelength of the at least one signal, (ii) a constant, or (iii) associated with at least one phase of at least one further frequency component of the interference signal over less than an entire sweep of the wavelength, and wherein the at least one frequency component and the at least one further frequency component are different from one another.

11. The apparatus according to claim 9, further comprising an optical configuration configured to receive one or more of the at least one first electro-magnetic radiation and the at least one second electro-magnetic radiation, and providing at least one fifth electro-magnetic radiation associated with the at least one first electro-magnetic radiation or the at least one second electro-magnetic radiation, wherein the at least one detector is further configured to detect a further interference signal between the at least one fifth radiation and the at least one fourth radiation, and wherein the at least one detector is further configured to obtain at least one reference signal associated with a further phase of at least one first frequency component of the further interference signal over less than an entire sweep of the wavelength.

12. The apparatus according to claim 11, wherein the first information is the further phase.

13. The apparatus according to claim 1, wherein the at least one computer is further configured and programmed to generate a two-dimensional fundus-type reflectivity profile of the anatomical sample.

14. The apparatus according to claim 1, wherein the at least one computer is further configured and programmed to generate a two-dimensional fundus-type image of the anatomical sample based the at least one signal.

15. The apparatus according to claim 1, wherein the wavelength of the radiation provided by the at least one light source that varies over time is swept in a controllable manner.

16. The apparatus according to claim 1, wherein the detector includes at least one single detector which detects the interference signal over multiple different wavelengths that change over time.

17. A method comprising:
causing a transmission of a light radiation;
causing a separation of the light radiation into at least one first electro-magnetic radiation directed to be provided to an anatomical sample and at least one second electro-magnetic radiation directed to a reference, wherein the anatomical sample includes at least one section, and wherein a wavelength of the radiation varies over time, and the wavelength is shorter than approximately 1150 nm;
causing an interference of at least one third radiation associated with the at least one first radiation and at least one fourth radiation associated with the at least one second radiation to generate an interference signal;
detecting the interference signal; and
generating at least one image corresponding to at least one portion of the anatomical sample using data associated with the interference signal.

18. A software arrangement provided on a non-transitory computer-accessible medium and executable by a computer, the computer-accessible medium comprising:
a first set of instructions which, when executed by the computer, controls at least one first electro-magnetic radiation to be directed to be provided to an anatomical sample and at least one second electro-magnetic radiation to be directed to a reference, wherein the anatomical sample includes at least one section, and wherein a wavelength of the radiation varies over time, and the wavelength is shorter than approximately 1150 nm;
a second set of instructions which, when executed by the computer, causes a detection of an interference between at least one third radiation associated with the at least one first radiation and at least one fourth radiation associated with the at least one second radiation using a detector to generate an interference signal; and
a second set of instructions which, when executed by the computer, causes the computer to generate at least one digital image corresponding to at least one portion of the anatomical sample using data associated with the interference signal.

19. The apparatus according to claim 18, wherein the detector includes at least one single detector which detects the interference signal over multiple different wavelengths that change over time.

20. An apparatus comprising:
at least one computer configured to receive first data for a three-dimensional image of at least one portion of a sample which includes at least one section,
wherein the first data is associated with an optical interferometric signal generated from light signals obtained from the anatomical sample and a reference, wherein the optical interferometric signal is based on a radiation whose a wavelength provided from a light source varies over time,
wherein the at least one computer is further configured to convert a region that is less than an entire portion of the first data to second digital data to generate a digital two-dimensional image which is associated with the at least one portion of the anatomical sample,
wherein the at least one computer is still further configured to automatically select the region based on at least one characteristic of the anatomical sample, and
wherein the entire portion is associated with an internal structure within the anatomical sample.

21. An apparatus comprising:
at least one light source configured to provide a light radiation;
a splitter configured to separate the light radiation into at least one first electro-magnetic radiation directed to an anatomical sample and at least one second electro-magnetic radiation directed to a reference, wherein a wavelength of the radiation provided by the at least one light source varies over time, and wherein the anatomical sample includes at least one section; and
at least one interferometer configured to interfere at least one third radiation associated with the at least one first radiation and at least one fourth radiation associated with the at least one second radiation to generate an interference signal;
at least one detector configured to detect the interference signal, wherein the at least one detector is configured to obtain at least one signal associated with at least one phase of at least one frequency component of the interference signal over less than an entire sweep of the wavelength; and
a computer configured to compare the at least one phase to at least one first information.

22. The apparatus according to claim 21, wherein the wavelength of the radiation provided by the at least one light source that varies over time is swept in a controllable manner.

* * * * *